US007169982B2

(12) United States Patent
Klucinec et al.

(10) Patent No.: US 7,169,982 B2
(45) Date of Patent: Jan. 30, 2007

(54) STARCH

(75) Inventors: Jeffrey D. Klucinec, Ames, IA (US);
Peter L. Keeling, Ames, IA (US);
Padma Commuri, Ames, IA (US);
Ming-Tang Chang, Ames, IA (US)

(73) Assignee: Basf Plant Science GmbH, Ludwigshafen (DE)

( * ) Notice: Subject to any disclaimer, the term of this patent is extended or adjusted under 35 U.S.C. 154(b) by 319 days.

(21) Appl. No.: 10/272,291

(22) Filed: Oct. 17, 2002

(65) Prior Publication Data
US 2003/0150023 A1    Aug. 7, 2003

Related U.S. Application Data

(60) Provisional application No. 60/329,525, filed on Oct. 17, 2001.

(51) Int. Cl.
*C12N 15/29* (2006.01)
*C12N 15/52* (2006.01)
*C12N 15/82* (2006.01)
*A01H 5/00* (2006.01)

(52) U.S. Cl. .................. 800/320.1; 800/270; 800/275; 800/284; 800/298; 536/23.1; 536/23.2; 536/23.6

(58) Field of Classification Search ................ 800/270, 800/278, 284, 285, 286, 298, 320–320.3, 800/275; 536/23.1, 23.2, 23.6
See application file for complete search history.

(56) References Cited

U.S. PATENT DOCUMENTS 5,300,145 A    4/1994    Fergason et al.

FOREIGN PATENT DOCUMENTS

EP    0 529 894 A1    3/1993

OTHER PUBLICATIONS

Graybosch R. A. et al. Trends in Food Science & Technology, 1998; vol. 9, pp. 135-142.*
Okagaki R. et al. Genetics, 1991, vol. 128; pp. 425-431.*
Hsieh J. et al. GenBank Accession Gi: 1255713, 1996.*
Amano E., Environmental Health Perspectives, 1981; vol. 37, pp. 35-41.*
Graybosch R., Trends in Food Science, 1998; vol. 9, pp. 135-142.*
Okagaki R. et al. Genetics, 1991,vol. 128; pp. 425-431.*
Klein, et al., The Feasibility of Investigating "Genetic Fine Structure" in Higher Plants, (1957), The American Naturalist, pp. 331-332.
Yeh, et al., Characterization of Starch from Maize Endosperm Mutants,(1980), The Pennsylvania Agricultural Experiment Station, pp. 222-230.
Kramer, et al., Quantitative Effects of Certain Genes on the Anylose Content of Corn Endosperm Starch, Agronomy Journal, pp. 409-411.

Kennedy, Extracellular polysaccharides of Rhizobium: identification of monosaccharides from strain CB756, (1978), Carbohydrate Research, pp. 217-221.
Shannon, et al., Genetics and Physiology of Starch Development, (1984), Starch, pp. 25-85.
Boyer, et al., Interaction of the anylose-extender and waxy mutants of maize, (1976), The Journal of Heredity, pp. 209-214.
Sprague, et al., The Development of Waxy Corn for Industrial Use, (1947), Iowa State College Journal of Science, pp. 205-213.
Sprague, et al., Some Effects of the Waxy Gene in Corn on Properties of the Endosperm Starch, (1943), Journal of the American Society of Agronomy, pp. 817-822.
Frost, et al., Waxy Endosperm in Argentine Maize, (1928), The Journal of Heredity, pp. 110-111.
Matveev, et al., The relationship between thermodynamic and structural properties of low and high amylose maize starches, (2001), Carbohydrate Polymers, pp. 151-160.
Wang, et al., Amylopectin and Intermediate Materials in Starches from Mutant Genotypes of the Oh43 Inbred Line, (1993), American Association of Cereal Chemists, Inc., pp. 521-525.
Brimhall, et al., A New Waxy Allel in Corn and its Effect on the Properties of the Endosperm Starch, (1945), Journal of the American Society of Agronomy, pp. 937-944.
ABSTRACT, Time-Lapse Motion Picture Technique Applied to the Study of Geological Processes, (1959), Science, vol. 130, pp. 793-794.
Sano, Differential regulation of waxy gene expression in rice endosperm, (1984), Theor Appl Genet, 68, pp. 467-473.
Sano, Genetic Studies of Speciation in Cultivated Rice.5. Inter- and Intraspecific Differentiation in the Waxy Gene Expression of Rice, (1986), Euphytica, 35, pp. 1-9.
Villareal, et al., Comparative Levels of Waxy Gene Product of Endosperm Starch Granules of Different Rice Ecotypes, (1989), starch/starke, 41, Nr. 10, S. pp. 369-371.
Bergman, et al., An Improved Method for Using a Microsatellite in the Rice Waxy Gene to Determine Anylose Class, (2001), Cereal Chem. 78(3), pp. 257-260.

(Continued)

*Primary Examiner*—Russell P. Kallis
(74) *Attorney, Agent, or Firm*—Patricia A. McDaniels

(57) ABSTRACT

This invention relates to a method of producing a starch with unique functionality in plants through mutableness, and/or using biotechnology, and/or breeding practices. Further the invention relates to the starch from maize plants and/or other plants which produce starch storing organs which contain low amylose starch which has an amylose content between 1.5% and 15% and preferably between 1.5% and 10% and most preferably 1.5 and 8%. The invention includes starch extracted from such grain due to at least one mutation induced by ethyl methanesulfonate. Additionally, the invention uses a biotechnology approach involving controlling the activity of the granule bound starch synthase enzyme in starch storing organ. The invention includes the use of the starch for its cooking, paste, and gel properties.

10 Claims, 14 Drawing Sheets

OTHER PUBLICATIONS

Juliano, et al., Properties of Waxy and Isogenic Nonwaxy Rices Differing in Starch Gelatinization Temperature, J. Agr. Food Chem., (1969), pp. 1364-1369.

Sanchez, et al., Nonwaxy Rice for Tapuy (Rice Wine) Production, (1988) American Association of Cereal Chemists, Inc., pp. 240-243.

Clarke, et al., The relationship between the rate of starch synthesis, the adenosine 5'-diphosphoglucose concentration and the amylose content of starch in developing pea embryos, (1999), Planta, 209, pp. 324-329.

Denyer, et al., The isolation and characterization of novel low-amylose mutants of *Pisum sativum* L., (1995), Plant, Cell and Environment, 18, pp. 1019-1026.

Edwards, et al., Discrete Forms of Amylose are Synthesized by Isoforms of GBSSI in Pea, (2002), The Plant Cell, vol. 14, pp. 1767-1785.

Miller, et al., Starch Characteristics of Selected Grain Sorghums as Related to Human Foods, (1970), Journal of Food Science, vol. 35, pp. 666-668.

Horan, et al., A Study of Sorghum and Sorghum Starches, (1946), Midwest Research Institute, pp. 492-503.

ABSTRACT, Publication No. C-1999-0804-06R, Correlation Between Cooked Rice Texture and Rapid Visco Analyser Measurements, Cereal Chemistry.

ABSTRACT, Publication No. C-2001-0807-02R, Categorizing Rice Cultivars Based on Cluster Analysis of Amylose Content, Protein Content and Sensory Attributes, Cereal Chemistry.

Lai, et al., Molecular Characteristics Influencing Retrogradation Kinetics of Rice Amylopectins, (2000) American Association of Cereal Chemists, Inc., pp. 272-278.

Shimada, et al., Antisense regulation of the rice waxy gene expression using a PCR-amplified fragment of the rice genome reduces the amylose content in grain starch, (1993), Theor Appl Genet, 86, pp. 665-672.

Wang, et al., The amylose content in rice endosperm is related to the post-transcriptional regulation of the waxy gene, (1995), The Plant Journal, 7(4), pp. 613-622.

Isshiki, et al., A naturally occurring functional allele of the rice waxy locus has a GT to TT mutation at the 5' splice site of the first intron, (1998), The Plant Journal, 15(1), pp. 133-138.

Wang, et al., Structures of Four Waxy Rice Starches in Relation to Thermal, Pasting, and Textural Properties, (2002), Cereal Chem., 79(2), pp. 252-256.

Kumar, et al., Inheritance of amylose content in rice (*Oryza sativa* L.), (1998), Euphytica, 38, pp. 261-269.

Daftary, et al., Changes in Lipid Compositions in Wheat during Storage Deterioration, (1965), J. Agr. Food Chem., vol. 13, No. 5, p. 442.

Villareal, et al., Amylopectin Staling of Cooked Milled Rices and Properties of Amylopectin and Amylose, (1997), Ceral Chem., 74(2), pp. 163-167.

Bett-Garber, et al., Categorizing Rice Cultivars Based on Cluster Analysis of Amylose Content, Protein Content and Sensory Attributes, (2001), Cereal Chem., vol. 78, No. 5, pp. 551-558.

Van Der Leij, et al., Complementation of the amyulose-free starch mutant of potato (*Solanum tuberosum*.) by the gene encoding granule-bound starch synthase, (1991), Theor. Appl. Genet., 82, pp. 289-295.

Salehuzzaman, et al., Expression of a cassava granule-bound starch synthase gene in the amylose-free potato only partially restores amylose content, (1999), Plant, Cell and Environment, 22, pp. 1311-1318.

Lloyd, et al., Simultaneous antisense inhibition of two starch-synthase isoforms in potato tubers leads to accumulation of grossly modified amylopectin, (1999), Biochem. J., 338, pp. 515-521.

Kuipers, et al., Formation and Deposition of Amylose in the Potato Tuber Starch Granule are Affected by the Reduction of Granule-bound Starch Synthase Gene Expression, (1994), The Plant Cell, vol. 6, pp. 43-52.

Visser, et al., Inhibition of the expression of the gene for granule-bound starch synthase in potato by antisense constructs, (1991), Mol. Gen. Genet., 225, pp. 289-296.

Hovenkamp-Hermelink, et al., Isolation of an amylose-free starch mutant of the potato (*Solanum tuberosum* L.), (1987), Theor. Appl. Genet., 75, pp. 217-221.

Flipse, et al., The dosage effect of the wildtype GBSS allele is linear for GBSS activity but not for amylose content: absence of amylose has a distinct influence on the physico-chemical properties of starch, (1996), Theor. Appl. Genet., 92, pp. 121-127.

Vasanthan, et al., Starch from hull-less barley: II. Thermal, rheological and acid hydrolysis characteristics, (2001), Food Chemistry 74, pp. 407-415.

Vasanthan, et al., Starch from hull-less barley: I. Granule morphology, composition and amylopectin structure, (2001), Food Chemistry, 74, pp. 395-405.

ABSTRACT, Yasui, et al., Online ISSN: 1521-379X, (2002) Starch-Starke, vol. 54, Issue 5, 2002, pp. 179-184.

ABSTRACT, Czuchajowska, et al., Publication No. C-1998-0807-05R, (1998), Cereal Chem. 75(5), pp. 747-754.

Fredriksson, et al., Characterisation of Starch from Inner and Peripheral Parts of Normal and Waxy Barley Kernels, (1999), Journal of Cereal Science, 30, pp. 165-171.

Song, et al., Characterization of barley starches of waxy, normal, and high amylose varieties, (2000), Carbohydrate Polymers, pp. 365-377.

Tang, et al., Some Physiocochemical Properties of Small-, Medium-, and Large-Granule Starches in Fractions of Waxy Barley Grain, (2000), Cereal Chem., 77(1), pp. 27-31.

Oda, et al., A Bread Wheat Mutant with Low Amylose Content Induced by Ethyl Methanesulphonate, (1992), Japan. J. Breed., 42, pp. 151-154.

Sasaki, et al., Effect of Amylose Content on Gelatinization, Retrogradation, and Pasting Properties of Starches from Waxy and Nonwaxy Wheat and Their F1 Seeds, (2000), Cereal Chem. 77(1), pp. 58-63.

Miura, et al., Dosage effects of the three Wx genes on amylose synthesis in wheat endosperm, (1996), Theor. Appl. Genet., 93, 1066-1070.

Miura, et al., Amylose synthesis capacity of the three Wx genes of wheat cv. Chinese Spring, (1999), Euphytica, 108, pp. 91-95.

Fujita, et al., A 56-kDa protein is a novel granule-bound starch synthase existing in the pericarps, aleurone layers, and embryos of immature seed in diploid wheat (*Triticum monococcum* L.), (1998), Planta, 207, 125-132.

Lee, et al., Influence of Amylose Content on Properties of Wheat Starch and Breadmaking Quality of Starch and Gluten Blends, (2001) Cereal Chem., 78(6), pp. 701-706.

Kiribuchi-Otobe, et al., Wheat Mutant with Waxy Starch Showing Stable Hot Paste Viscosity, (1998), Cereal Chem. 75(5), pp. 671-672.

Nakamura, et al., Production of waxy (anylose-free) wheats, (1995), Gen Genet., 248, pp. 253-259.

Ainsworth, et al., Expression, organisation and structure of the genes encoding the waxy protein (granule-bound starch synthase) in wheat, (1993), Plant Molecular Biology, 22, pp. 67-82.

Sasaki, et al., Effect of Amylose Content on Gelatinization, Retrogradation, and Pasting Properties of Starches from Waxy and Nonwaxy Wheat and Their F1 Seeds, (2000), Cereal Chem., 77(1), pp. 58-63.

Demeke, et al., Biochemical Characterization of the Wheat Waxy A protein and Its Effect on Starch Properties, (1999), Cereal Chem., 76(5), pp. 694-698.

Vrinten, et al., Wheat Granule-Bound Starch Synthase I and II are Encoded by Separate Genes that are Expressed in Different Tissues, (2000), Plant Physiology, vol. 122, pp. 255-263.

Fujita, et al., The isolation and characterization of a waxy mutant of diploid wheat (*Triticum monococcum* L.), (2001), Plant Science, 160, pp. 595-602.

Marcoz-Ragot, et al., Allelic variants of granule-bound starch synthase proteins in European breat wheat varieties, (2000), Plant Breeding, 119, pp. 305-309.

Stoddard, Genetics of wheat starch B-granule content, (2000), Euphytica, 112, pp. 23-31.

Li, et al., The Localization and Expression of the Class II Starch Synthases of Wheat[1], (1999), Plant Physiology, vol. 120, pp. 1147-1155.

Yanagisawa, et al., An alanine to threonine change in the Wx-D1 protein reduces GBSS I activity in waxy mutant wheat, (2001), Euphytica, 121, pp. 209-214.

Hovenkamp, et al., Theor. Appl. Genet. (1987) 75, 217-221.

Salehuzzaman, et al., Plant, Cell and Environment (1999) 22, 1311-1318.

Okagaki, et al., Genetics (1991) 128, 425-431.

Kulpers, et al., The Plant Cell (1994) 6, 43-52.

Graybosch, Trends in Food Science and Technology (1998) 9, 135-142.

* cited by examiner

Figure 11
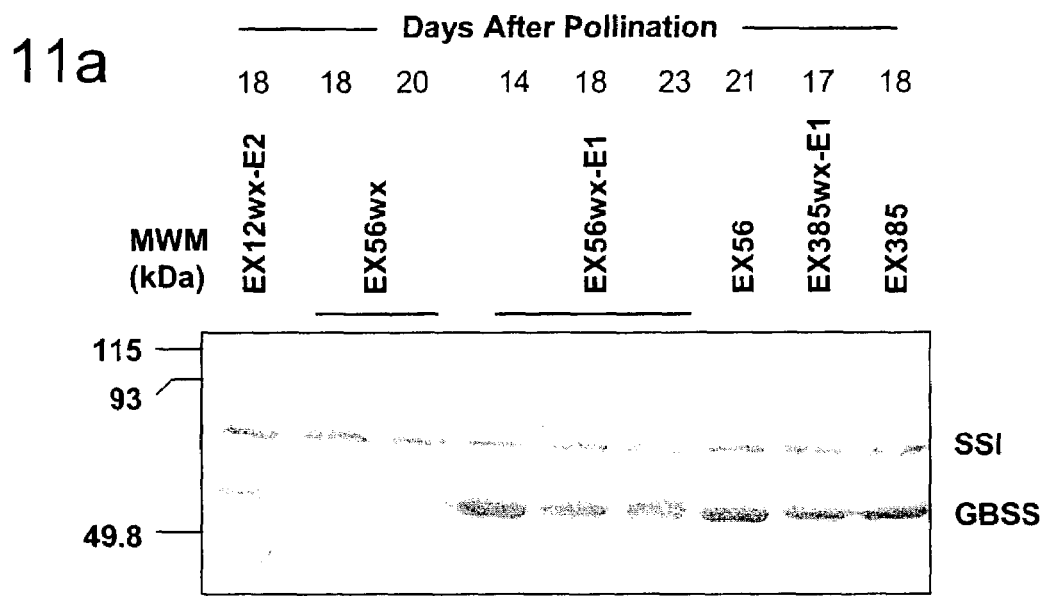
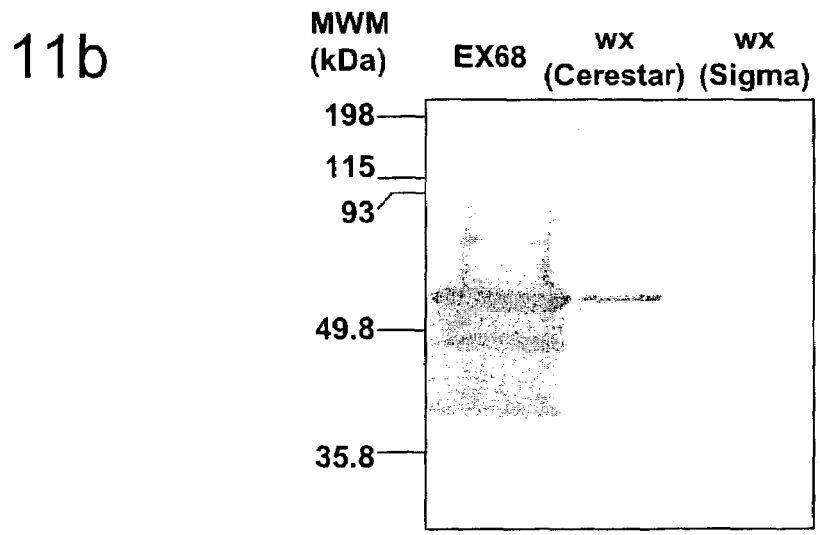

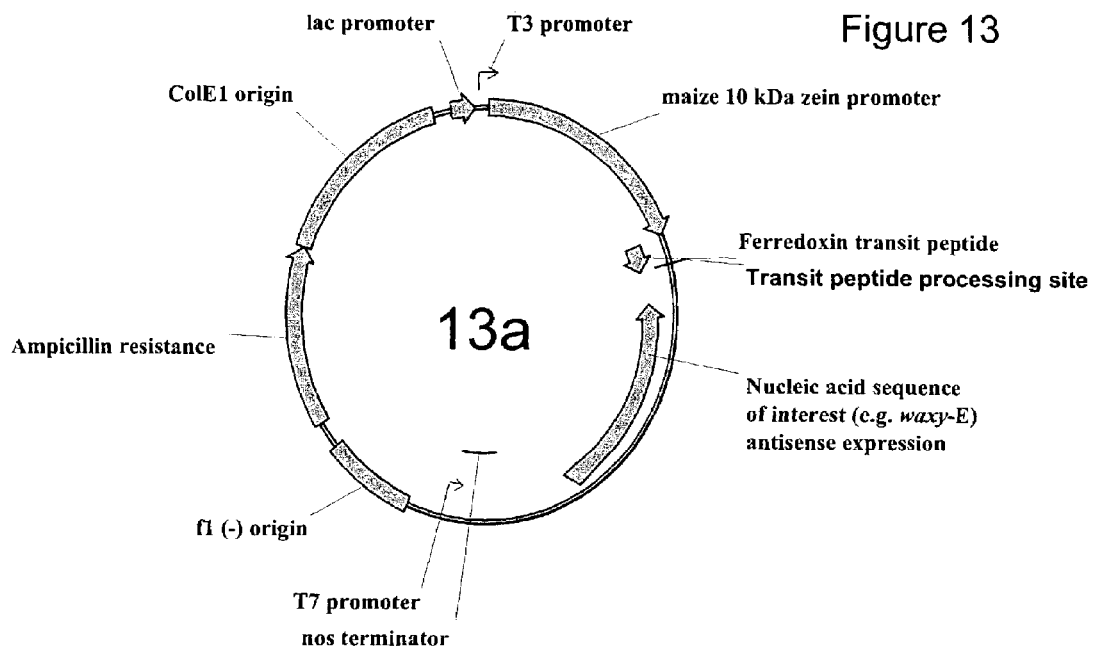
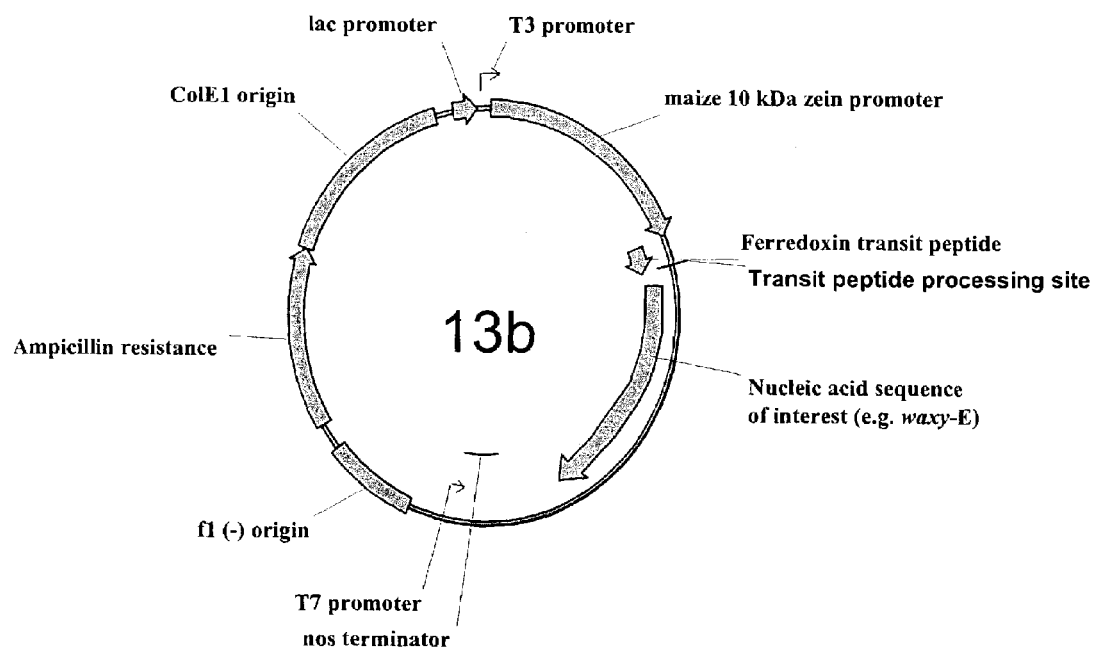
Figure 13

| Promoter | Transit | Coding regions for | Terminator |
| Intron* | peptide | modified GBSS enzyme | |
| | coding | (*waxy*-E locus) | |
| | region* | | |

*optional components

SEQUENCE LISTING

<160> NUMBER OF SEQ ID NOS: 8

<210> SEQ ID NO 1
<211> LENGTH: 2263
<212> TYPE: DNA
<213> ORGANISM: Zea mays
<220> FEATURE:
<223> OTHER INFORMATION: Wild type sequence EX385

<400> SEQUENCE: 1

```
cgtcacatcc atccatcgac cgatcgatcg ccacagccaa caccacccgc cgaggcgacg      60
cgacagccgc caggaggaag gaataaactc actgccagcc agtgaagggg gagaagtgta     120
```

-continued

```
ctgctccgtc gaccagtgcg cgcaccgccc ggcagggctg ctcatctcgt cgacgaccag      180
tggattaatc ggcatggcgg ctctggccac gtcgcagctc gtcgcaacgc gcgccggcct      240
gggcgtcccg gacgcgtcca cgttccgccg cggcgccgcg cagggcctga ggggggcccg      300
ggcgtcggcg gcggcggaca cgctcagcat gcggaccagc gcgcgcgcgg cgcccaggca      360
ccagcagcag gcgcgccgcg ggggcaggtt cccgtcgctc gtcgtgtgcg ccagcgccgg      420
catgaacgtc gtcttcgtcg cgccgagat ggcgccgtgg agcaagaccg gcggcctcgg       480
cgacgtcctc ggcggcctgc cgccggccat ggccgcgaac gggcaccgtg tcatggtcgt      540
ctctccccgc tacgaccagt acaaggacgc ctgggacacc agcgtcgtgt ccgagatcaa      600
gatgggagac gggtacgaga cggtcaggtt cttccactgc tacaagcgcg agtggaccg       660 cgtgttcgtt gaccacccac tgttcctgga gagggtttgg ggaaagaccg aggagaagat      720
ctacgggcct gtcgctggaa cggactacag ggacaaccag ctgcggttca gcctgctatg      780
ccaggcagca cttgaagctc caaggatcct gagcctcaac aacaacccat acttctccgg      840
accatacggg gaggacgtcg tgttcgtctg caacgactgg cacaccggcc ctctctcgtg      900
ctacctcaag agcaactacc agtcccacgg catctacagg gacgcaaaga ccgctttctg      960
catccacaac atctcctacc agggccggtt cgccttctcc gactaccgg agctgaacct      1020 cccggagaga ttcaagtcgt ccttcgattt catcgacggc tacgagaagc ccgtggaagg     1080
ccggaagatc aactggatga aggccgggat cctcgaggcc gacagggtcc tcaccgtcag     1140
cccctactac gccgaggagc tcatctccgg catcgccagg gctgcgagc tcgacaacat     1200 catgcgcctc accggcatca ccggcatcgt caacggcatg gacgtcagcg agtgggaccc     1260
cagcagggac aagtacatcg ccgtgaagta cgacgtgtcg acggccgtgg aggccaaggc     1320
gctgaacaag gaggcgctgc aggcggaggt cgggctcccg gtggaccgga acatcccgct     1380
ggtggcgttc atcggcaggc tggaagagca gaagggcccc gacgtcatgg cggccgccat     1440
cccgcagctc atggagatgg tggaggacgt gcagatcgtt ctgctgggca cgggcaagaa     1500
gaagttcgag cgcatgctca tgagcgccga ggagaagttc ccaggcaagg tgcgcgccgt     1560
ggtcaagttc aacgcggcgc tggcgcacca tcatggcc ggcgccgacg tgctcgccgt      1620
caccagccgc ttcgagcccct gcggcctcat ccagctgcag gggatgcgat acggaacgcc     1680
ctgcgcctgc gcgtccaccg gtggactcgt cgacaccatc atcgaaggca agaccgggtt     1740
ccacatgggc cgcctcagcg tcgactgtaa cgtcgtggag ccggcggacg tcaagaaggt     1800
ggccaccaca ttgcagcgcg ccatcaaggt ggtcggcacg ccggcgtacg aggagatggt     1860
gaggaactgc atgatccagg atctctcctg gaagggccct gccaagaact gggagaacgt     1920
gctgctcagc ctcggggtcg ccggcggcga gccagggtc gaaggcgagg agatcgcgcc      1980
gctcgccaag gagaacgtgg ccgcgccctg aagagttcgg cctgcaggc ccctgatctc      2040 gcgcgtggtg caaagatgtt gggacatctt cttatatatg ctgtttcgtt tatgtgatat     2100
ggacaagtat gtgtagctgc ttgcttgtgc tagtgtaatg tagtgtagtg gtggccagtg     2160
gcacaaccta ataagcgcat gaactaattg cttgcgtgtg tagttaagta ccgatcggta     2220
attttatatt gcgagtaaat aaatggacct gtagtggtgg agt                       2263
```

<210> SEQ ID NO 2
<211> LENGTH: 2263
<212> TYPE: DNA
<213> ORGANISM: Zea mays
<220> FEATURE:

-continued

<221> NAME/KEY: mutation
<222> LOCATION: (1643)
<223> OTHER INFORMATION: The mutation is at position 1643 in the
      sequence,1450 bp after the start codon.
<220> FEATURE:
<221> NAME/KEY: mutation
<222> LOCATION: (1643)
<223> OTHER INFORMATION: The change is a "G" in the wild type (EX385) to
      an "A" in the mutant

<400> SEQUENCE: 2

| | |
|---|---|
| cgtcacatcc atccatcgac cgatcgatcg ccacagccaa caccacccgc cgaggcgacg | 60 |
| cgacagccgc caggaggaag gaataaactc actgccagcc agtgaagggg gagaagtgta | 120 |
| ctgctccgtc gaccagtgcg cgcaccgccc ggcagggctg ctcatctcgt cgacgaccag | 180 |
| tggattaatc ggcatggcgg ctctggccac gtcgcagctc gtcgcaacgc gcgccggcct | 240 |
| gggcgtcccg gacgcgtcca cgttccgccg cggcgccgcg cagggcctga gggggcccg | 300 |
| ggcgtcggcg gcggcggaca cgctcagcat gcggaccagc gcgcgcgcgg cgcccaggca | 360 |
| ccagcagcag gcgcgccgcg ggggcaggtt cccgtcgctc gtcgtgtgcg ccagcgccgg | 420 |
| catgaacgtc gtcttcgtcg gcgccagat ggcgccgtgg agcaagaccg gcggcctcgg | 480 |
| cgacgtcctc ggcggcctgc cgccggccat ggccgcgaac gggcaccgtg tcatggtcgt | 540 |
| ctctccccgc tacgaccagt acaaggacgc ctgggacacc agcgtcgtgt ccagagatcaa | 600 |
| gatgggagac gggtacgaga cggtcaggtt cttccactgc tacaagcgcg gagtggaccg | 660 |
| cgtgttcgtt gaccacccac tgttcctgga gagggtttgg ggaaagaccg aggagaagat | 720 |
| ctacgggcct gtcgctggaa cggactacag ggacaaccag ctgcggttca gcctgctatg | 780 |
| ccaggcagca cttgaagctc caaggatcct gagcctcaac aacaacccat acttctccgg | 840 |
| accatacggg gaggacgtcg tgttcgtctg caacgactgg cacaccggcc ctctctcgtg | 900 |
| ctacctcaag agcaactacc agtcccacg catctacagg gacgcaaaga ccgctttctg | 960 |
| catccacaac atctcctacc agggccggtt cgccttctcc gactacccgg agctgaacct | 1020 |
| cccggagaga ttcaagtcgt ccttcgattt catcgacggc tacgaaagc ccgtggaagg | 1080 |
| ccggaagatc aactggatga aggccgggat cctcgaggcc gacagggtcc tcaccgtcag | 1140 |
| cccctactac gccgaggagc tcatctccgg catcgccagg ggctgcgagc tcgacaacat | 1200 |
| catgcgcctc accggcatca ccggcatcgt caacggcatg gacgtcagcg agtgggaccc | 1260 |
| cagcagggac aagtacatcg ccgtgaagta cgacgtgtcg acggccgtgg aggccaaggc | 1320 |
| gctgaacaag gaggcgctgc aggcggaggt cgggctcccg gtggaccgga acatcccgct | 1380 |
| ggtggcgttc atcggcaggc tggaagagca aagggcccc gacgtcatgg cggccgccat | 1440 |
| cccgcagctc atggagatgg tggaggacgt gcagatcgtt ctgctgggca cgggcaagaa | 1500 |
| gaagttcgag cgcatgctca tgagcgccga ggagaagttc ccaggcaagg tgcgcgccgt | 1560 |
| ggtcaagttc aacgcggcgc tggcgcacca tcatggcc ggcgccgacg tgctcgccgt | 1620 |
| caccagccgc ttcgagccct gcagcctcat ccagctgcag gggatgcgat acggaacgcc | 1680 |
| ctgcgcctgc gcgtccaccg gtggactcgt cgacaccatc atcgaaggca agaccggggtt | 1740 |
| ccacatgggc cgcctcagcg tcgactgtaa cgtcgtggag ccggcggacg tcaagaaggt | 1800 |
| ggccaccaca ttgcagcgcg ccatcaaggt ggtcggcacg ccggcgtacg aggagatggt | 1860 |
| gaggaactgc atgatccagg atctctcctg gaagggccct gccaagaact gggagaacgt | 1920 |
| gctgctcagc ctcgggggtcg ccggcggcga gccaggggtc gaaggcgagg agatcgcgcc | 1980 |
| gctcgccaag gagaacgtgg ccgcgccctg aagagttcgg cctgcagggc ccctgatctc | 2040 |

-continued

```
gcgcgtggtg caaagatgtt gggacatctt cttatatatg ctgtttcgtt tatgtgatat    2100
ggacaagtat gtgtagctgc ttgcttgtgc tagtgtaatg tagtgtagtg gtggccagtg    2160
gcacaaccta ataagcgcat gaactaattg cttgcgtgtg tagttaagta ccgatcggta    2220
attttatatt gcgagtaaat aaatggacct gtagtggtgg agt                       2263
```

<210> SEQ ID NO 3
<211> LENGTH: 600
<212> TYPE: PRT
<213> ORGANISM: Zea mays
<220> FEATURE:
<223> OTHER INFORMATION: Wild type EX385 sequence

<400> SEQUENCE: 3

```
Met Ala Ala Leu Ala Thr Ser Gln Leu Val Ala Thr Arg Ala Gly Leu
  1               5                  10                  15

Gly Val Pro Asp Ala Ser Thr Phe Arg Arg Gly Ala Ala Gln Gly Leu
                 20                  25                  30

Arg Gly Ala Arg Ala Ser Ala Ala Ala Asp Thr Leu Ser Met Arg Thr
         35                  40                  45

Ser Ala Arg Ala Ala Pro Arg His Gln Gln Gln Ala Arg Arg Gly Gly
     50                  55                  60

Arg Phe Pro Ser Leu Val Val Cys Ala Ser Ala Gly Met Asn Val Val
 65                  70                  75                  80

Phe Val Gly Ala Glu Met Ala Pro Trp Ser Lys Thr Gly Gly Leu Gly
                 85                  90                  95

Asp Val Leu Gly Gly Leu Pro Pro Ala Met Ala Ala Asn Gly His Arg
                100                 105                 110

Val Met Val Val Ser Pro Arg Tyr Asp Gln Tyr Lys Asp Ala Trp Asp
         115                 120                 125

Thr Ser Val Val Ser Glu Ile Lys Met Gly Asp Gly Tyr Glu Thr Val
     130                 135                 140

Arg Phe Phe His Cys Tyr Lys Arg Gly Val Asp Arg Val Phe Val Asp
145                 150                 155                 160

His Pro Leu Phe Leu Glu Arg Val Trp Gly Lys Thr Glu Glu Lys Ile
                165                 170                 175

Tyr Gly Pro Val Ala Gly Thr Asp Tyr Arg Asp Asn Gln Leu Arg Phe
                180                 185                 190

Ser Leu Leu Cys Gln Ala Ala Leu Glu Ala Pro Arg Ile Leu Ser Leu
         195                 200                 205

Asn Asn Asn Pro Tyr Phe Ser Gly Pro Tyr Gly Glu Asp Val Val Phe
     210                 215                 220

Val Cys Asn Asp Trp His Thr Gly Pro Leu Ser Cys Tyr Leu Lys Ser
225                 230                 235                 240

Asn Tyr Gln Ser His Gly Ile Tyr Arg Asp Ala Lys Thr Ala Phe Cys
                245                 250                 255

Ile His Asn Ile Ser Tyr Gln Gly Arg Phe Ala Phe Ser Asp Tyr Pro
                260                 265                 270

Glu Leu Asn Leu Pro Glu Arg Phe Lys Ser Ser Phe Asp Phe Ile Asp
         275                 280                 285

Gly Tyr Glu Lys Pro Val Glu Gly Arg Lys Ile Asn Trp Met Lys Ala
     290                 295                 300

Gly Ile Leu Glu Ala Asp Arg Val Leu Thr Val Ser Pro Tyr Tyr Ala
305                 310                 315                 320
```

```
Glu Glu Leu Ile Ser Gly Ile Ala Arg Gly Cys Leu Asp Asn Ile
            325                 330                 335

Met Arg Leu Thr Gly Ile Thr Gly Ile Val Asn Gly Met Asp Val Ser
            340                 345                 350

Glu Trp Asp Pro Ser Arg Asp Lys Tyr Ile Ala Val Lys Tyr Asp Val
            355                 360                 365

Ser Thr Ala Val Glu Ala Lys Ala Leu Asn Lys Glu Ala Leu Gln Ala
    370                 375                 380

Glu Val Gly Leu Pro Val Asp Arg Asn Ile Pro Leu Val Ala Phe Ile
385                 390                 395                 400

Gly Arg Leu Glu Glu Gln Lys Gly Pro Asp Val Met Ala Ala Ile
                405                 410                 415

Pro Gln Leu Met Glu Met Val Glu Asp Val Gln Ile Val Leu Leu Gly
                420                 425                 430

Thr Gly Lys Lys Lys Phe Glu Arg Met Leu Met Ser Ala Glu Glu Lys
            435                 440                 445

Phe Pro Gly Lys Val Arg Ala Val Val Lys Phe Asn Ala Ala Leu Ala
    450                 455                 460

His His Ile Met Ala Gly Ala Asp Val Leu Ala Val Thr Ser Arg Phe
465                 470                 475                 480

Glu Pro Cys Gly Leu Ile Gln Leu Gln Gly Met Arg Tyr Gly Thr Pro
                485                 490                 495

Cys Ala Cys Ala Ser Thr Gly Gly Leu Val Asp Thr Ile Ile Glu Gly
                500                 505                 510

Lys Thr Gly Phe His Met Gly Arg Leu Ser Val Asp Cys Asn Val Val
            515                 520                 525

Glu Pro Ala Asp Val Lys Lys Val Ala Thr Thr Leu Gln Arg Ala Ile
    530                 535                 540

Lys Val Val Gly Thr Pro Ala Tyr Glu Glu Met Val Arg Asn Cys Met
545                 550                 555                 560

Ile Gln Asp Leu Ser Trp Lys Gly Pro Ala Lys Asn Trp Glu Asn Val
                565                 570                 575

Leu Leu Ser Leu Gly Val Ala Gly Gly Glu Pro Gly Val Glu Gly Glu
            580                 585                 590

Glu Ile Ala Pro Leu Ala Lys Glu
            595                 600

<210> SEQ ID NO 4
<211> LENGTH: 600
<212> TYPE: PRT
<213> ORGANISM: Zea mays
<220> FEATURE:
<221> NAME/KEY: VARIANT
<222> LOCATION: (484)
<223> OTHER INFORMATION: The glycine (wild type) was mutated to a
      serine at residue 484.

<400> SEQUENCE: 4

Met Ala Ala Leu Ala Thr Ser Gln Leu Val Ala Thr Arg Ala Gly Leu
1               5                   10                  15

Gly Val Pro Asp Ala Ser Thr Phe Arg Arg Gly Ala Ala Gln Gly Leu
                20                  25                  30

Arg Gly Ala Arg Ala Ser Ala Ala Ala Asp Thr Leu Ser Met Arg Thr
            35                  40                  45

Ser Ala Arg Ala Ala Pro Arg His Gln Gln Gln Ala Arg Arg Gly Gly
    50                  55                  60
```

```
Arg Phe Pro Ser Leu Val Val Cys Ala Ser Ala Gly Met Asn Val Val
 65                  70                  75                  80

Phe Val Gly Ala Glu Met Ala Pro Trp Ser Lys Thr Gly Gly Leu Gly
                 85                  90                  95

Asp Val Leu Gly Gly Leu Pro Pro Ala Met Ala Ala Asn Gly His Arg
            100                 105                 110

Val Met Val Ser Pro Arg Tyr Asp Gln Tyr Lys Asp Ala Trp Asp
            115                 120                 125

Thr Ser Val Val Ser Glu Ile Lys Met Gly Asp Gly Tyr Glu Thr Val
    130                 135                 140

Arg Phe Phe His Cys Tyr Lys Arg Gly Val Asp Arg Val Phe Val Asp
145                 150                 155                 160

His Pro Leu Phe Leu Glu Arg Val Trp Gly Lys Thr Glu Glu Lys Ile
                165                 170                 175

Tyr Gly Pro Val Ala Gly Thr Asp Tyr Arg Asp Asn Gln Leu Arg Phe
            180                 185                 190

Ser Leu Leu Cys Gln Ala Ala Leu Glu Ala Pro Arg Ile Leu Ser Leu
        195                 200                 205

Asn Asn Asn Pro Tyr Phe Ser Gly Pro Tyr Gly Glu Asp Val Val Phe
    210                 215                 220

Val Cys Asn Asp Trp His Thr Gly Pro Leu Ser Cys Tyr Leu Lys Ser
225                 230                 235                 240

Asn Tyr Gln Ser His Gly Ile Tyr Arg Asp Ala Lys Thr Ala Phe Cys
                245                 250                 255

Ile His Asn Ile Ser Tyr Gln Gly Arg Phe Ala Phe Ser Asp Tyr Pro
            260                 265                 270

Glu Leu Asn Leu Pro Glu Arg Phe Lys Ser Ser Phe Asp Phe Ile Asp
        275                 280                 285

Gly Tyr Glu Lys Pro Val Glu Gly Arg Lys Ile Asn Trp Met Lys Ala
    290                 295                 300

Gly Ile Leu Glu Ala Asp Arg Val Leu Thr Val Ser Pro Tyr Tyr Ala
305                 310                 315                 320

Glu Glu Leu Ile Ser Gly Ile Ala Arg Gly Cys Glu Leu Asp Asn Ile
                325                 330                 335

Met Arg Leu Thr Gly Ile Thr Gly Ile Val Asn Gly Met Asp Val Ser
            340                 345                 350

Glu Trp Asp Pro Ser Arg Asp Lys Tyr Ile Ala Val Lys Tyr Asp Val
        355                 360                 365

Ser Thr Ala Val Glu Ala Lys Ala Leu Asn Lys Glu Ala Leu Gln Ala
    370                 375                 380

Glu Val Gly Leu Pro Val Asp Arg Asn Ile Pro Leu Val Ala Phe Ile
385                 390                 395                 400

Gly Arg Leu Glu Glu Gln Lys Gly Pro Asp Val Met Ala Ala Ala Ile
                405                 410                 415

Pro Gln Leu Met Glu Met Val Glu Asp Val Gln Ile Val Leu Leu Gly
            420                 425                 430

Thr Gly Lys Lys Lys Phe Glu Arg Met Leu Met Ser Ala Glu Glu Lys
        435                 440                 445

Phe Pro Gly Lys Val Arg Ala Val Val Lys Phe Asn Ala Ala Leu Ala
    450                 455                 460

His His Ile Met Ala Gly Ala Asp Val Leu Ala Val Thr Ser Arg Phe
465                 470                 475                 480

Glu Pro Cys Ser Leu Ile Gln Leu Gln Gly Met Arg Tyr Gly Thr Pro
```

```
                       485                 490                 495
Cys Ala Cys Ala Ser Thr Gly Gly Leu Val Asp Thr Ile Ile Glu Gly
            500                 505                 510

Lys Thr Gly Phe His Met Gly Arg Leu Ser Val Asp Cys Asn Val Val
            515                 520                 525

Glu Pro Ala Asp Val Lys Lys Val Ala Thr Thr Leu Gln Arg Ala Ile
            530                 535                 540

Lys Val Val Gly Thr Pro Ala Tyr Glu Glu Met Val Arg Asn Cys Met
545                 550                 555                 560

Ile Gln Asp Leu Ser Trp Lys Gly Pro Ala Lys Asn Trp Glu Asn Val
            565                 570                 575

Leu Leu Ser Leu Gly Val Ala Gly Gly Glu Pro Gly Val Glu Gly Glu
            580                 585                 590

Glu Ile Ala Pro Leu Ala Lys Glu
            595                 600

<210> SEQ ID NO 5
<211> LENGTH: 4800
<212> TYPE: DNA
<213> ORGANISM: Zea mays
<220> FEATURE:
<221> NAME/KEY: transit_peptide
<222> LOCATION: (1233)..(1448)
<220> FEATURE:
<221> NAME/KEY: intron
<222> LOCATION: (1554)..(1684)
<223> OTHER INFORMATION: number 2
<220> FEATURE:
<221> NAME/KEY: intron
<222> LOCATION: (1766)..(1859)
<223> OTHER INFORMATION: number 3
<220> FEATURE:
<221> NAME/KEY: intron
<222> LOCATION: (1959)..(2054)
<223> OTHER INFORMATION: number 4
<220> FEATURE:
<221> NAME/KEY: intron
<222> LOCATION: (2145)..(2225)
<223> OTHER INFORMATION: number 5
<220> FEATURE:
<221> NAME/KEY: intron
<222> LOCATION: (2290)..(2412)
<223> OTHER INFORMATION: number 6
<220> FEATURE:
<221> NAME/KEY: intron
<222> LOCATION: (2514)..(2650)
<223> OTHER INFORMATION: number 7
<220> FEATURE:
<221> NAME/KEY: intron
<222> LOCATION: (2761)..(2857)
<223> OTHER INFORMATION: number 8
<220> FEATURE:
<221> NAME/KEY: intron
<222> LOCATION: (3102)..(3211)
<223> OTHER INFORMATION: number 9
<220> FEATURE:
<221> NAME/KEY: intron
<222> LOCATION: (3395)..(3489)
<223> OTHER INFORMATION: number 10
<220> FEATURE:
<221> NAME/KEY: intron
<222> LOCATION: (3682)..(3792)
<223> OTHER INFORMATION: number 11
<220> FEATURE:
<221> NAME/KEY: intron
<222> LOCATION: (3880)..(3976)
<223> OTHER INFORMATION: number 12
<220> FEATURE:
<221> NAME/KEY: intron
<222> LOCATION: (4106)..(4226)
<223> OTHER INFORMATION: number 13
```

<400> SEQUENCE: 5

```
cagcgaccta ttacacagcc cgctcgggcc cgcgacgtcg ggacacatct tcttccccct      60
tttggtgaag ctctgctcgc agctgtccgg ctccttggac gttcgtgtgg cagattcatc     120
tgttgtctcg tctcctgtgc ttcctgggta gcttgtgtag tggagctgac atggtctgag     180
caggcttaaa atttgctcgt agacgaggag taccagcaca gcacgttgcg gatttctctg     240
cctgtgaagt gcaacgtcta ggattgtcac acgccttggt cgcgtcgcgt cgcgtcgcgt     300
cgatgcggtg gtgagcagag cagcaacagc tgggcggccc aacgttggct tccgtgtctt     360
cgtcgtacgt acgcgcgcgc cggggacacg cagcagagag cggagagcga gccgtgcacg     420
gggaggtggt gtggaagtgg agccgcgcgc ccggccgccc gcgcccggtg ggcaacccaa     480
aagtacccac gacaagcgaa ggcgccaaag cgatccaagc tccggaacgc aacagcatgc     540
gtcgcgtcgg agagccagcc acaagcagcc gagaaccgaa ccggtgggcg acgcgtcatg     600
ggacggacgc gggcgacgct tccaaacggg ccacgtacgc cggcgtgtgc gtgcgtgcag     660
acgacaagcc aaggcgaggc agcccccgat cgggaaagcg ttttgggcgc gagcgctggc     720
gtgcgggtca gtcgctggtg cgcagtgccg gggggaacgg gtatcgtggg gggcgcgggc     780
ggaggagagc gtggcgaggg ccgagagcag cgcgcggccg ggtcacgcaa cgcgccccac     840
gtactgccct ccccctccgc gcgcgctaga aataccgagg cctggaccgg ggggggccc      900
cgtcacatcc atccatcgac cgatcgatcg ccacagccaa caccaccgc cgaggcgacg      960
cgacagccgc caggaggaag gaataaactc actgccagcc agtgaagggg gagaagtgta    1020
ctgctccgtc gaccagtgcg cgcaccgccc ggcagggctg ctcatctcgt cgacgaccag    1080
gttctgttcc gttccgatcc gatccgatcc tgtccttgag tttcgtccag atcctggcgc    1140
gtatctgcgt gtttgatgat ccaggttctt cgaacctaaa tctgtccgtg cacacgtctt    1200
ttctctctct cctacgcagt ggattaatcg gcatggcggc tctggccacg tcgcagctcg    1260
tcgcaacgcg cgccggcctg ggcgtcccgg acgcgtccac gttccgccgc ggcgccgcgc    1320
agggcctgag gggggcccgg gcgtcggcgg cggcggacac gctcagcatg cggaccagcg    1380
cgcgcgcggc gcccaggcac cagcagcagg cgcgccgcgg gggcaggttc ccgtcgctcg    1440
tcgtgtgcgc cagcgccggc atgaacgtcg tcttcgtcgg cgccgagatg cgccgtgga    1500
gcaagaccgg cggcctcggc gacgtcctcg gcggcctgcc gccggccatg gccgtaagcg    1560
cgcgcaccga gacatgcatc cgttggatcg cgtcttcttc gtgctcttgc cgcgtgcatg    1620
atgcatgtgt ttcctcctgg cttgtgttcg tgtatgtgac gtgtttgttc gggcatgcat    1680
gcaggcgaac gggcaccgtg tcatggtcgt ctctccccgc tacgaccagt acaaggacgc    1740
ctgggacacc agcgtcgtgt ccgaggtacg gccaccgaga ccagattcag atcacagtca    1800
cacacaccgt catatgaacc tttctctgct ctgatgcctg caactgcaaa tgcatgcaga    1860
tcaagatggg agacgggtac gagacggtca ggttcttcca ctgctacaag cgcggagtgg    1920
accgcgtgtt cgttgaccac ccactgttcc tggagagggt gagacgagat ctgatcactc    1980
gatacgcaat taccacccca ttgtaagcag ttacagtgag cttttttttcc ccccggcctg    2040
gtcgctggtt tcaggtttgg ggaaagaccg aggagaagat ctacgggcct gtcgctggaa    2100
cggactacag ggacaaccag ctgcggttca gcctgctatg ccaggtcagg atggcttggt    2160
actacaactt catatcatct gtatgcagca gtatacactg atgagaaatg catgctgttc    2220
tgcaggcagc acttgaagct ccaaggatcc tgagcctcaa caacaaccca tacttctccg    2280
```

-continued

| | | | | |
|---|---|---|---|---|
| gaccatacgg | taagagttgc | agtcttcgta | tatatatctg | ttgagctcga gaatcttcac | 2340 |
| aggaagcggc | ccatcagacg | gactgtcatt | ttacactgac | tactgctgct gctcttcgtc | 2400 |
| catccataca | aggggaggac | gtcgtgttcg | tctgcaacga | ctggcacacc ggccctctct | 2460 |
| cgtgctacct | caagagcaac | taccagtccc | acggcatcta | cagggacgca aaggttgcct | 2520 |
| tctctgaact | gaacaacgcc | gttttcgttc | tccatgctcg | tatatacctc gtctggtagt | 2580 |
| ggtggtgctt | ctctgagaaa | ctaactgaaa | ctgactgcat | gtctgtctga ccatcttcac | 2640 |
| gtactaccag | accgctttct | gcatccacaa | catctcctac | cagggccggt tcgccttctc | 2700 |
| cgactacccg | gagctgaacc | tcccggagag | attcaagtcg | tccttcgatt tcatcgacgg | 2760 |
| gtctgttttc | ctgcgtgcat | gtgaacattc | atgaatggta | acccacaact gttcgcgtcc | 2820 |
| tgctggttca | ttatctgacc | tgattgcatt | attgcagcta | cgagaagccc gtggaaggcc | 2880 |
| ggaagatcaa | ctggatgaag | gccgggatcc | tcgaggccga | cagggtcctc accgtcagcc | 2940 |
| cctactacgc | cgaggagctc | atctccggca | tcgccagggg | ctgcgagctc gacaacatca | 3000 |
| tgcgcctcac | cggcatcacc | ggcatcgtca | acggcatgga | cgtcagcgag tgggacccca | 3060 |
| gcagggacaa | gtacatcgcc | gtgaagtacg | acgtgtcgac | ggtgagctgg ctagctctga | 3120 |
| ttctgctgcc | tggtcctcct | gctcatcatg | ctggttcggt | actgacgcgg caagtgtacg | 3180 |
| tacgtgcgtg | cgacggtggt | gtccggttca | ggccgtggag | gccaaggcgc tgaacaagga | 3240 |
| ggcgctgcag | gcggaggtcg | ggctcccggt | ggaccggaac | atcccgctgg tggcgttcat | 3300 |
| cggcaggctg | gaagagcaga | agggcccccga | cgtcatggcg | gccgccatcc cgcagctcat | 3360 |
| ggagatggtg | gaggacgtgc | agatcgttct | gctggtacgt | gtgcgccggc cgccacccgg | 3420 |
| ctactacatg | cgtgtatcgt | tcgttctact | ggaacatgcg | tgtgagcaac gcgatggata | 3480 |
| atgctgcagg | gcacgggcaa | gaagaagttc | gagcgcatgc | tcatgagcgc cgaggagaag | 3540 |
| ttcccaggca | aggtgcgcgc | cgtggtcaag | ttcaacgcgg | cgctggcgca ccacatcatg | 3600 |
| gccggcgccg | acgtgctcgc | cgtcaccagc | cgcttcgagc | cctgcggcct catccagctg | 3660 |
| caggggatgc | gatacggaac | ggtacgagag | aaaaaaaaaa | tcctgaatcc tgacgagagg | 3720 |
| gacagagaca | gattatgaat | gcttcatcga | tttgaattga | ttgatcgatg tctcccgctg | 3780 |
| cgactcttgc | agccctgcgc | ctgcgcgtcc | accggtggac | tcgtcgacac catcatcgaa | 3840 |
| ggcaagaccg | ggttccacat | gggccgcctc | agcgtcgacg | taagcctagc tctgccatgt | 3900 |
| tctttcttct | ttctttctgt | atgtatgtat | gaatcagcac | cgccgttctt gtttcgtcgt | 3960 |
| cgtcctctct | tcccagtgta | acgtcgtgga | gccggcggac | gtcaagaagg tggccaccac | 4020 |
| attgcagcgc | gccatcaagg | tggtcggcac | gccggcgtac | gaggagatgg tgaggaactg | 4080 |
| catgatccag | gatctctcct | ggaaggtacg | tacgcccgcc | ccgccccgcc ccgccagagc | 4140 |
| agagcgccaa | gatcgaccga | tcgaccgacc | acacgtacgc | gcctcgctcc tgtcgctgac | 4200 |
| cgtggtttaa | tttgcgaaat | gcgcaggggcc | ctgccaagaa | ctgggagaac gtgctgctca | 4260 |
| gcctcggggt | cgccggcggc | gagccagggg | tcgaaggcga | ggagatcgcg ccgctcgcca | 4320 |
| aggagaacgt | ggccgcgccc | tgaagagttc | ggcctgcagg | gcccctgatc tcgcgcgtgg | 4380 |
| tgcaaagatg | ttgggacatc | ttcttatata | tgctgtttcg | tttatgtgat atggacaagt | 4440 |
| atgtgtagct | gcttgcttgt | gctagtgtaa | tgtagtgtag | tggtggccag tggcacaacc | 4500 |
| taataagcgc | atgaactaat | tgcttgcgtg | tgtagttaag | taccgatcgg taattttata | 4560 |
| ttgcgagtaa | ataaatggac | ctgtagtggt | ggagtaaata | atccctgctg ttcggtgttc | 4620 |
| ttatcgctcc | tcgtatagat | attatataga | gtacattttt | ctctctctga atcctacgtt | 4680 |

-continued

```
tgtgaaattt ctatatcatt actgtaaaat ttctgcgttc caaagagac catagcctat    4740 ctttggccct gtttgtttcg gcttctggca gcttctggcc accaaaagct gctgcggact   4800
```

<210> SEQ ID NO 6
<211> LENGTH: 605
<212> TYPE: PRT
<213> ORGANISM: Zea mays
<220> FEATURE:
<223> OTHER INFORMATION: Granule bound starch synthase (maize) reference
      sequence
<220> FEATURE:
<223> OTHER INFORMATION: Accession number X03935

<400> SEQUENCE: 6

```
Met Ala Ala Leu Ala Thr Ser Gln Leu Val Ala Thr Arg Ala Gly Leu
 1               5                  10                  15

Gly Val Pro Asp Ala Ser Thr Phe Arg Arg Gly Ala Ala Gln Gly Leu
                20                  25                  30

Arg Gly Ala Arg Ala Ser Ala Ala Ala Asp Thr Leu Ser Met Arg Thr
            35                  40                  45

Ser Ala Arg Ala Ala Pro Arg His Gln Gln Ala Arg Arg Gly Gly
        50                  55                  60

Arg Phe Pro Ser Leu Val Val Cys Ala Ser Ala Gly Met Asn Val Val
 65                  70                  75                  80

Phe Val Gly Ala Glu Met Ala Pro Trp Ser Lys Thr Gly Gly Leu Gly
                85                  90                  95

Asp Val Leu Gly Gly Leu Pro Pro Ala Met Ala Ala Asn Gly His Arg
            100                 105                 110

Val Met Val Val Ser Pro Arg Tyr Asp Gln Tyr Lys Asp Ala Trp Asp
        115                 120                 125

Thr Ser Val Val Ser Glu Ile Lys Met Gly Asp Gly Tyr Glu Thr Val
    130                 135                 140

Arg Phe Phe His Cys Tyr Lys Arg Gly Val Asp Arg Val Phe Val Asp
145                 150                 155                 160

His Pro Leu Phe Leu Glu Arg Val Trp Gly Lys Thr Glu Glu Lys Ile
                165                 170                 175

Tyr Gly Pro Val Ala Gly Thr Asp Tyr Arg Asp Asn Gln Leu Arg Phe
            180                 185                 190

Ser Leu Leu Cys Gln Ala Ala Leu Glu Ala Pro Arg Ile Leu Ser Leu
        195                 200                 205

Asn Asn Asn Pro Tyr Phe Ser Gly Pro Tyr Gly Glu Asp Val Val Phe
    210                 215                 220

Val Cys Asn Asp Trp His Thr Gly Pro Leu Ser Cys Tyr Leu Lys Ser
225                 230                 235                 240

Asn Tyr Gln Ser His Gly Ile Tyr Arg Asp Ala Lys Thr Ala Phe Cys
                245                 250                 255

Ile His Asn Ile Ser Tyr Gln Gly Arg Phe Ala Phe Ser Asp Tyr Pro
            260                 265                 270

Glu Leu Asn Leu Pro Glu Arg Phe Lys Ser Ser Phe Asp Phe Ile Asp
        275                 280                 285

Gly Tyr Glu Lys Pro Val Glu Gly Arg Lys Ile Asn Trp Met Lys Ala
    290                 295                 300

Gly Ile Leu Glu Ala Asp Arg Val Leu Thr Val Ser Pro Tyr Tyr Ala
305                 310                 315                 320

Glu Glu Leu Ile Ser Gly Ile Ala Arg Gly Cys Glu Leu Asp Asn Ile
```

```
                    325                 330                 335
Met Arg Leu Thr Gly Ile Thr Gly Ile Val Asn Gly Met Asp Val Ser
            340                 345                 350

Glu Trp Asp Pro Ser Arg Asp Lys Tyr Ile Ala Val Lys Tyr Asp Val
            355                 360                 365

Ser Thr Ala Val Glu Ala Lys Ala Leu Asn Lys Glu Ala Leu Gln Ala
        370                 375                 380

Glu Val Gly Leu Pro Val Asp Arg Asn Ile Pro Leu Val Ala Phe Ile
385                 390                 395                 400

Gly Arg Leu Glu Glu Gln Lys Gly Pro Asp Val Met Ala Ala Ala Ile
                405                 410                 415

Pro Gln Leu Met Glu Met Val Glu Asp Val Gln Ile Val Leu Leu Gly
            420                 425                 430

Thr Gly Lys Lys Lys Phe Glu Arg Met Leu Met Ser Ala Glu Glu Lys
        435                 440                 445

Phe Pro Gly Lys Val Arg Ala Val Val Lys Phe Asn Ala Ala Leu Ala
    450                 455                 460

His His Ile Met Ala Gly Ala Asp Val Leu Ala Val Thr Ser Arg Phe
465                 470                 475                 480

Glu Pro Cys Gly Leu Ile Gln Leu Gln Gly Met Arg Tyr Gly Thr Pro
                485                 490                 495

Cys Ala Cys Ala Ser Thr Gly Gly Leu Val Asp Thr Ile Ile Glu Gly
            500                 505                 510

Lys Thr Gly Phe His Met Gly Arg Leu Ser Val Asp Cys Asn Val Val
        515                 520                 525

Glu Pro Ala Asp Val Lys Lys Val Ala Thr Thr Leu Gln Arg Ala Ile
    530                 535                 540

Lys Val Val Gly Thr Pro Ala Tyr Glu Glu Met Val Arg Asn Cys Met
545                 550                 555                 560

Ile Gln Asp Leu Ser Trp Lys Gly Pro Ala Lys Asn Trp Glu Asn Val
                565                 570                 575

Leu Leu Ser Leu Gly Val Ala Gly Gly Glu Pro Gly Val Glu Gly Glu
            580                 585                 590

Glu Ile Ala Pro Leu Ala Lys Glu Asn Val Ala Ala Pro
        595                 600                 605

<210> SEQ ID NO 7
<211> LENGTH: 477
<212> TYPE: PRT
<213> ORGANISM: Zea mays
<220> FEATURE:
<223> OTHER INFORMATION: Starch Synthase IIb-2 (N-terminally truncated
      SSIIb)

<400> SEQUENCE: 7

Met Asn Val Val Val Ala Ser Glu Cys Ala Pro Phe Cys Lys Thr
1               5                  10                  15

Gly Gly Leu Gly Asp Val Val Gly Ala Leu Pro Lys Ala Leu Ala Arg
            20                  25                  30

Arg Gly His Arg Val Met Val Val Ile Pro Arg Tyr Gly Glu Tyr Ala
        35                  40                  45

Glu Ala Arg Asp Leu Gly Val Arg Arg Tyr Lys Val Ala Gly Gln
    50                  55                  60

Asp Ser Glu Val Thr Tyr Phe His Ser Tyr Ile Asp Gly Val Asp Phe
65                  70                  75                  80
```

```
Val Phe Val Glu Ala Pro Pro Phe Arg His Arg His Asn Asn Ile Tyr
                85                  90                  95

Gly Gly Glu Arg Leu Asp Ile Leu Lys Arg Met Ile Leu Phe Cys Lys
            100                 105                 110

Ala Ala Val Glu Val Pro Trp Tyr Ala Pro Cys Gly Gly Thr Val Tyr
            115                 120                 125

Gly Asp Gly Asn Leu Val Phe Ile Ala Asn Asp Trp His Thr Ala Leu
130                 135                 140

Leu Pro Val Tyr Leu Lys Ala Tyr Tyr Arg Asp Asn Gly Leu Met Gln
145                 150                 155                 160

Tyr Ala Arg Ser Val Leu Val Ile His Asn Ile Ala His Gln Gly Arg
                165                 170                 175

Gly Pro Val Asp Asp Phe Val Asn Phe Asp Leu Pro Glu His Tyr Ile
            180                 185                 190

Asp His Phe Lys Leu Tyr Asp Asn Ile Gly Gly Asp His Ser Asn Val
            195                 200                 205

Phe Ala Ala Gly Leu Lys Thr Ala Asp Arg Val Val Thr Val Ser Asn
210                 215                 220

Gly Tyr Met Trp Glu Leu Lys Thr Ser Glu Gly Gly Trp Gly Leu His
225                 230                 235                 240

Asp Ile Ile Asn Gln Asn Asp Trp Lys Leu Gln Gly Ile Val Asn Gly
                245                 250                 255

Ile Asp Met Ser Glu Trp Asn Pro Ala Val Asp Val His Leu His Ser
            260                 265                 270

Asp Asp Tyr Thr Asn Tyr Thr Phe Glu Thr Leu Asp Thr Gly Lys Arg
            275                 280                 285

Asp Asp Val Pro Leu Ile Gly Phe Ile Gly Arg Leu Asp His Gln Lys
290                 295                 300

Gly Val Asp Ile Ile Ala Asp Ala Ile His Trp Ile Ala Gly Gln Asp
305                 310                 315                 320

Val Gln Leu Val Met Leu Gly Thr Gly Arg Ala Asp Leu Glu Asp Met
                325                 330                 335

Leu Arg Arg Phe Glu Ser Glu His Ser Asp Lys Val Arg Ala Trp Val
            340                 345                 350

Gly Phe Ser Val Pro Leu Ala His Arg Ile Thr Ala Gly Ala Asp Ile
            355                 360                 365

Leu Leu Met Pro Ser Arg Phe Glu Pro Cys Gly Leu Asn Gln Leu Tyr
370                 375                 380

Ala Met Ala Tyr Gly Thr Val Pro Val Val His Ala Val Gly Gly Leu
385                 390                 395                 400

Arg Asp Thr Val Ala Pro Phe Asp Pro Phe Asn Asp Thr Gly Leu Gly
                405                 410                 415

Trp Thr Phe Asp Arg Ala Glu Ala Asn Arg Met Ile Asp Ala Leu Ser
            420                 425                 430

His Cys Leu Thr Thr Tyr Arg Asn Tyr Lys Glu Ser Trp Arg Ala Cys
            435                 440                 445

Arg Ala Arg Gly Met Ala Glu Asp Leu Ser Trp Asp His Ala Ala Val
450                 455                 460

Leu Tyr Glu Asp Val Leu Val Lys Ala Lys Tyr Gln Trp
465                 470                 475

<210> SEQ ID NO 8
<211> LENGTH: 641
<212> TYPE: PRT
```

```
<213> ORGANISM: Zea mays
<220> FEATURE:
<223> OTHER INFORMATION: Starch Synthase IIa (SSIIa)

<400> SEQUENCE: 8

Met Ala Glu Ala Glu Ala Gly Gly Lys Asp Ala Pro Glu Arg Ser
 1               5                  10                  15

Gly Asp Ala Ala Arg Leu Pro Arg Ala Arg Asn Ala Val Ser Lys
                20                  25                  30

Arg Arg Asp Pro Leu Gln Pro Val Gly Arg Tyr Gly Ser Ala Thr Gly
        35                  40                  45

Asn Thr Ala Arg Thr Gly Ala Ala Ser Cys Gln Asn Ala Ala Leu Ala
    50                  55                  60

Asp Val Glu Ile Lys Ser Ile Val Ala Ala Pro Pro Thr Ser Ile Val
65                  70                  75                  80

Lys Phe Pro Ala Pro Gly Tyr Arg Met Ile Leu Pro Ser Gly Asp Ile
                85                  90                  95

Ala Pro Glu Thr Val Leu Pro Ala Pro Lys Pro Leu His Glu Ser Pro
                100                 105                 110

Ala Val Asp Gly Asp Ser Asn Gly Ile Ala Pro Pro Thr Val Glu Pro
                115                 120                 125

Leu Val Gln Glu Ala Thr Trp Asp Phe Lys Lys Tyr Ile Gly Phe Asp
130                 135                 140

Glu Pro Asp Glu Ala Lys Asp Asp Ser Arg Val Gly Ala Asp Asp Ala
145                 150                 155                 160

Gly Ser Phe Glu His Tyr Gly Asp Asn Asp Ser Gly Pro Leu Ala Gly
                165                 170                 175

Glu Asn Val Met Asn Val Ile Val Val Ala Ala Glu Cys Ser Pro Trp
                180                 185                 190

Cys Lys Thr Gly Gly Leu Gly Asp Val Val Gly Ala Leu Pro Lys Ala
                195                 200                 205

Leu Ala Arg Arg Gly His Arg Val Met Val Val Pro Arg Tyr Gly
210                 215                 220

Asp Tyr Val Glu Ala Phe Asp Met Gly Ile Arg Lys Tyr Tyr Lys Ala
225                 230                 235                 240

Ala Gly Gln Asp Leu Glu Val Asn Tyr Phe His Ala Phe Ile Asp Gly
                245                 250                 255

Val Asp Phe Val Phe Ile Asp Ala Pro Leu Phe Arg His Arg Gln Asp
                260                 265                 270

Asp Ile Tyr Gly Gly Ser Arg Gln Glu Ile Met Lys Arg Met Ile Leu
                275                 280                 285

Gly Val Cys Tyr Gly Asp Gly Asn Leu Val Phe Ile Ala Asn Asp Trp
                290                 295                 300

His Thr Ala Leu Leu Pro Val Tyr Leu Lys Ala Tyr Arg Asp His
305                 310                 315                 320

Gly Leu Met Gln Tyr Thr Arg Ser Val Leu Val Ile His Asn Ile Ala
                325                 330                 335

His Gln Gly Arg Gly Pro Val Asp Glu Phe Pro Tyr Met Asp Leu Pro
                340                 345                 350

Glu His Tyr Leu Gln His Phe Glu Leu Tyr Asp Pro Val Gly Gly Glu
                355                 360                 365

His Ala Asn Ile Phe Ala Ala Gly Leu Lys Met Ala Asp Arg Val Val
                370                 375                 380

Thr Val Ser Arg Gly Tyr Leu Trp Glu Leu Lys Thr Val Glu Gly Gly
```

-continued

```
385                 390                 395                 400
Trp Gly Leu His Asp Ile Ile Arg Ser Asn Asp Trp Lys Ile Asn Gly
                405                 410                 415
Ile Val Asn Gly Ile Asp His Gln Glu Trp Asn Pro Lys Val Asp Val
                420                 425                 430
His Leu Arg Ser Asp Gly Tyr Thr Asn Tyr Ser Leu Glu Thr Leu Asp
                435                 440                 445
Ala Gly Lys Arg Gln Cys Lys Ala Ala Leu Gln Arg Glu Leu Gly Leu
    450                 455                 460
Glu Val Arg Asp Asp Val Pro Leu Leu Gly Phe Ile Gly Arg Leu Asp
465                 470                 475                 480
Gly Gln Lys Gly Val Asp Ile Ile Gly Asp Ala Met Pro Trp Ile Ala
                485                 490                 495
Gly Gln Asp Val Gln Leu Val Met Leu Gly Thr Gly Arg Ala Asp Leu
                500                 505                 510
Glu Arg Met Leu Gln His Leu Glu Arg Glu His Pro Asn Lys Val Arg
                515                 520                 525
Gly Trp Val Gly Phe Ser Val Pro Met Ala His Arg Ile Thr Ala Gly
    530                 535                 540
Ala Asp Val Leu Val Met Pro Ser Arg Phe Glu Pro Cys Gly Leu Asn
545                 550                 555                 560
Gln Leu Tyr Ala Met Ala Tyr Gly Thr Val Pro Val Val His Ala Val
                565                 570                 575
Ala Gly Leu Gly Trp Thr Phe Asp Arg Ala Glu Ala Asn Lys Leu Ile
                580                 585                 590
Glu Ala Leu Arg His Cys Leu Asp Thr Tyr Arg Lys Tyr Gly Glu Ser
    595                 600                 605
Trp Lys Ser Leu Gln Ala Arg Gly Met Ser Gln Asp Leu Ser Trp Asp
    610                 615                 620
His Ala Ala Glu Leu Tyr Glu Asp Val Leu Val Lys Ala Lys Tyr Gln
625                 630                 635                 640
Trp
```

STARCH

The present application is based on and claims benefit of U.S. Prvisional Application No. 60/329,525, filed Oct. 17, 2001, the entire contents of which is incorporated herein by reference.

The present invention relates to a starch defined herein as elastic starch. The presently disclosed starch has been made possible by engineering the waxy locus of starch producing plants, or the gene-product of the waxy locus (i.e., the GBSS protein) which synthesizes amylose. The starch of the present invention therefore may be viewed as a reduced amylose starch or a special type of waxy starch with new elastic properties. The starch of the present invention is referred to herein as waxy-E or wx-E starch, to emphasize this elastic property not previously available with known waxy starch. In particular, the starch of the present invention has special properties of high viscosity and valuable paste and gel properties not previously found in natural (i.e., wild-type) starches or waxy starches of plants of similar species. The special properties of the starches of the present invention are believed to be the product of the unique combination of reduced amylose content of the starch of the present invention, as compared to starch of a wild-type plant of the same species, and a similar amylopectin structure of the starch of the present invention, as compared to starch of a wild-type plant of the same species. While these special properties have been characterized herein using a Rapid Visco Analyzer, one of ordinary skill in the art will appreciate that other means are available to characterize the physical properties which may be used to describe the presently disclosed starch. The starch of the present invention may be obtained from plants and/or plant parts through mutableness or by plant transformation or other approaches known in the art to reduce the amylose content of plants without affecting amylopectin structure and without reducing amylose content as significantly as is found in waxy-starches which have little or no amylose. Further, the invention relates to a method of increasing the elasticity of a formulation by utilizing a waxy-E starch of the present invention.

Chemically, starch can be described as a mixture of two homoglucose polymers: amylose and amylopectin. Amylose is a generally linear $\alpha$-1,4 glucan which sometimes is lightly-branched with $\alpha$-1,6-glycosidic linkages. Amylopectin is normally larger than amylose and is highly-branched with $\alpha$-1,6-glycosidic linkages. The balance of amylose and amylopectin in normal starches isolated from storage tissues like potato tubers or cereal grain is normally between 20 to 30 percent amylose and the remainder 70 to 80 percent is described as amylopectin on a dry starch weight basis.

Plants displaying altered starch storing organ phenotypes have been important in advancing our understanding of how starch is produced in plants. For example, numerous phenotypes have been reported for maize (Glover and Mertz, 1987, Corn, in Agronomy. American Society of Agronomy, Madison; Coe et al, 1988, The genetic of corn, in Corn and Corn Improvement, 3rd edition, G. F. Sprague and J. W. Dudley, eds. American Society of Agronomy, Madison) and several phenotypes (e.g., waxy, amylose extender, dull, shrunken, sugary-2, and sugary) have been described extensively with regard to their effects on carbohydrate composition and response to genetic background, allelic dosage, or interaction with other mutations (example references: Creech, 1965, Genetics 52:1175–1186; Holder et al, 1974, Crop Science 14:643–646; Garwood and Vanderslice, 1982, Crop Science 22:367–371; Garwood et al, 1976, Cereal Chemistry 53:355–364). Many studies of starch storing organ phenotypes have focused on the molecular structure of synthesized polysaccharides and the concentration and type of soluble carbohydrates found in the starch storing organ during early-to-mid development. In particular, examination of maize starch storing organs with differing phenotypes have been instrumental in characterizing carbohydrate metabolism in cereal grain and determining which enzymes have a role in regulating starch biosynthesis (for review see Boyer, 1985, Phytochemistry 24:15–18; Shannon and Garwood, 1984, Starch: Chemistry and Technology; R. L. Whistler, J. N. BeMiller, and E. F. Paschall, eds; Academic Press, Orlando).

Across all plants, one starch storing organ phenotype produces a starch which contains a low quantity of amylose. This phenotype is called "waxy" starches for historical reasons: in maize the phenotype of the intact seed has a waxy phenotypic appearance. Plants producing waxy starch are often referred to as waxy plants or waxy mutants; the gene is commonly referred to as the waxy gene. Granule bound starch synthase [GBSS-ADPglucose:1,4-$\alpha$-D-glucan-4-$\alpha$-D-glucosyltransferase (E.C. 2.4.1.21)] enzyme activity is strongly correlated with the product of the waxy gene (Shure et al, 1983, Cell 35: 225–233). The synthesis of amylose in a number of species such as maize, rice and potato has been shown to depend on the expression of this gene (Tsai, 1974, Biochemical Genetics 11: 83–96; Hovenkamp-Hermelink et al, 1987, Theoretical and Applied Genetics 75: 217–221). Visser et al described the molecular cloning and partial characterization of the gene for granule-bound starch synthase from potato (1989, Journal of Plant Science 64:185–192). Visser et al (1991, Molecular and General Genetics 225:289–296) have also described the inhibition of the expression of the gene for GBSS in potato by antisense constructs. Further, starch synthases (EC 2.4.1.11 and EC 2.4.1.21) elongate starch molecules (Delrue et al, 1992, Bacteriology 174:3612–3620; Denyer et al, 1999a, Biochemical Journal 340:183–191; Denyer et al, 1999b, Biochemical Journal 342:647–653) and are thought to act on both amylose and amylopectin. Starch synthase [SS-ADPglucose:1,4-$\alpha$-D-glucan-4-$\alpha$-D-glucosyltransferase (EC 2.4.1.11)] activity can be found associated both with the granule and in the stroma of the plastid. The capacity for starch association of the bound starch synthase enzyme is well known. Various enzymes involved in starch biosynthesis are now known to have differing propensities for binding as described by Mu-Forster et al (1996, Plant Physiology 111: 821–829). The other SS enzymes have become known as soluble starch synthases, following the pioneering work of Frydman and Cardini (Frydman and Cardini, 1964, Biochemical and Biophysical Research Communications 17:407–411). Recently, the appropriateness of the term "soluble" has become questionable in light of discoveries that these enzymes are associated with the granule as well as being present in the soluble phase (Denyer et al, 1993, Plant Journal 4:191–198; Denyer et al, 1995, Planta 97:57–62; Mu-Forster et al, 1996, Plant Physiology 111: 821–829). It is generally believed that the biosynthesis of amylopectin involves the interaction of soluble starch synthases and starch branching enzymes. Different isoforms of soluble starch synthase have been identified and cloned in pea (Denyer and Smith, 1992, Planta 186: 609–617; Dry et al, 1992, Plant Journal, 2: 193–202), potato (Edwards et al, 1995, Plant Physiology 112: 89–97; Marshall et al, 1996, Plant Cell 8: 1121–1135) and in rice (Baba et al, 1993, Plant Physiology 103:565–573), while barley appears to contain multiple isoforms, some of which are associated with starch branching enzyme (Tyynela and Schulman, 1994, Physiologica Plantarum 89: 835–841). In maize, two soluble forms of SS, known as isoforms I and II, have been identified (Macdonald and Preiss, 1983, Plant Physiology 73: 175–178; Boyer and Preiss, 1978, Carbohydrate Research 61:321–334; Pollock and Preiss, 1980, Archives of Biochemistry and Biophysics 204:578–588; Macdonald and Preiss, 1985 Plant Physiology 78: 849–852; Dang and Boyer, 1988, Phytochemistry 27: 1255–1259; Mu et al, 1994, Plant Journal 6:151–159), but neither of these has been cloned. SSI activity of maize endosperm was found to be correlated with a 76-kDa polypeptide found in both soluble and granule-associated fractions (Mu et al, 1994, Plant Journal 6:151–159). The polypeptide identity of SSII remains unknown.

Waxy maize starch which contains essentially no amylose has been known for many years (Shannon and Garwood, 1984; Starch: Chemistry and Technology; R. L. Whistler, J. N. BeMiller, and E. F. Paschall, eds; Academic Press, Orlando; pp 50–56). There are examples of such waxy starches in peas, maize, rice, potato, sorghum, wheat, barley and other plants.

For many plants including wheat, peas, corn, and potatoes among others, a principal purpose for their domestication and cultivation is for starch production. The utilization of the starch may be in the form of the intact starch storing organ itself (e.g. a baked potato) or as a preparation of a substantially complete starch storing organ (e.g. flour or meal or sliced potatoes). Alternatively, the starch may be isolated from starch storing organs for incorporation into foodstuffs (e.g. pie fillings, puddings, soups, sauces, gravies, coatings, candies and/or confectionary products, and/or yoghurts and other dairy products) and/or industrially-derived products (e.g. paper sizing aids, textile sizing aids, and/or suspension aids). Starch is produced in plants as granules: microscopic structures with spherical, elliptical, or polyhedral shapes which contain individual starch molecules.

Examination of the color that starch stains with the addition of iodine is one of the simplest methods of identifying waxy starches. When stained with iodine, normal starch will stain blue or purple. A waxy starch will be red or brown or brownish-red in color when stained with iodine because the amylose component is severely reduced such that there is little, or essentially no amylose present. Waxy starches have been consistently described as (a) nearly 100% amylopectin or (b) isolated from plant starch storage organs which lack a GBSS enzyme in the endosperm or (c) from plant starch storage organs which have originated from a plant which produces a starch which is nearly 100% amylopectin or (d) from plant starch storage organs which have originated from a plant which lacks a GBSS enzyme in the endosperm or (e) having some or all of these qualities or (f) having unknown or undocumented quality (U.S. Pat. Nos. 4,428,972; 4,615,888; 4,767,849; 4,789,557; 4,789,738; 4,801,470; 6,143,963).

Some waxy starches might stain blue or purple and may appear to contain some amylose as a result of changes in amylopectin structure. For example, in maize long-chain amylopectin is produced due to the decrease in starch branching enzyme activity as a result of the amylose-extender mutation in the starch biosynthetic pathway (Boyer et al, 1976, Journal of Heredity 67:209–214). Waxy amylose-extender starch, starch which is produced in plants having both waxy and amylose-extender mutations, may have an apparent amylose content of 15% to 26% (Shannon and Garwood, 1984; Starch: Chemistry and Technology; R. L. Whistler, J. N. BeMiller, and E. F. Paschall, eds; Academic Press, Orlando; p 65). The differences in the structure of waxy starch and waxy amylose-extender starch, and the effects of the amylose-extender mutation on starch in general, are clearly observed in the distribution of their component chains (Jane et al, 1999, Cereal Chemistry 76:629–637). This and other alterations of the starch biosynthetic pathway have an effect on amylopectin structure and starch cooking, gelling, pasting, and in general, starch rheological properties.

Thus, starch granules which have a blue coloration contain long chains. The long chains may either be real amylose or a component of the amylopectin of the starch as a result of an alteration in the starch biosynthetic pathway (e.g. the amylose-extender mutation in maize), resulting in an apparent amylose content by some methods and no amylose by others (Klucinec and Thompson, 1998, Cereal Chemistry 75:887–896). Additionally, amylopectin and waxy starch may appear to have an amylose content of 5% itself by quantitative iodine staining methods. This amylose may be attributed to the low iodine-binding capacity of the amylopectin and may be falsely attributed to amylose when the iodine binding capacity of the amylopectin is not taken into consideration during measurements (Knutson and Grove, 1994, Cereal Chemistry 71: 469–471).

Much time and effort has been spent to produce waxy starch which stains red by virtue of the fact that in this form it has very little amylose. Waxy starch and normal starch differ in the way they change during a cooking process. Heating starch in water or an aqueous solution results in changes in the starch granules (Whistler and Daniel, 1985, Carbohydrates, in Food Chemistry, O. R. Fennema, ed., Marcel Dekker, Inc., New York, pp. 114–115). During heating, granules swell end the organized structures maintaining the granule structure dissociate, permitting further swelling. With additional heating and applied shear forces, granules will eventually collapse to form an unorganized paste of starch molecules. This process of starch granule swelling and dissociation, known as gelatinization, is known to those familiar with the art (Atwell et al, 1988, Cereal Foods World 33(3):306–311; Tester and Morrison, 1990, Cereal Chemistry 67:551–557). Upon cooling, starch begins to reorganize into structures resembling those which originally held the starch granules together, however the complete highly-organized structure of the granule is never reestablished. This process of reorganization, known as retrogradation, is well-known to those familiar with the art (Atwell et al, 1988, Cereal Foods World 33(3):306–311). Retrogradation often involves changes in the physical properties of the starch paste, including a decrease I pate clarity and gelation of the paste. Normal starches are generally recognized for its ability to gel within hours (Ring, 1985, Starch/Stärke 37;80–83), while wary starches are generally recognized for their ability to require weeks to gel if they gel at all (Yuan and Thompson, 1998, Cereal Chemistry 75:117–123; Biliaderis, 1992, Characterization of starch networks by small strain dynamic oscillatory rheometry, in Developments in Carbohydrate Chemistry, R. J. Alexander an H. F. Zobel, eds., American Association of Cereal Chemists, St. Paul, p 103). Normal starches are generally recognized for forming opaque pastes and gels, while waxy starches arc generally recognized for remaining transparent after processing (Craig et. al, 1989, Cereal Chemistry 66:173–182). Waxy starches are considered useful as water binders, viscosity builders, and texturizers in food as well as industrial applications (Reddy and Seib, 2000, Journal of Cereal Science 31:25–39). Waxy starches also have better freeze-thaw stability and clarity compared to normal starches once cooked (Whistler and BeMiller, 1997, Carbohydrate chemistry for Food Scientists, Eagan Press, St. Paul, p. 146; Reddy and Sept. 2000, Journal of Cereal Science 31:25–39). Waxy starches are also less resistant to shear, acid, and high temperatures than are normal starches, and extended cooking of waxy starches result in stringy, cohesive pastes (Whistler and BeMiller, 1997, Carbohydrate chemistry for Food Scientists, Eagan Press, St Paul, p. 142; Reddy and Seib, 2000, Journal of Cereal Science 31:25–39). These characteristics of waxy starch are believed to be a result of the molecular characteristics of the starch, specifically the absence of amylose (Whistler and Daniel, 1985, Carbohydrates, in Food Chemistry, O. R. Fennema, ed., Marcel Dekker, Inc., New York, p. 113), tough the precise behavior of the starch also depends on the concentration of the starch and the conditions under which it is processed and subsequently stored. Finally, it is generally recognized that it is common for waxy starch to be chemically modified by substitution, crosslinking, or both to improve its stability to temperature, shear and acid as well as minimize its undesirable paste qualitites (Whistler and Daniel, 1985, Carbohydrates, in Food Chemistry, O. R. Fennema, ed., Marcel Dekker, Inc., New York, pp. 118–120). Such practices are common to those familiar with the art (Zheng, G. H, et ad, 1999, Cereal Chemistrty 76:182–188; Reddy ad Seib, 2000, Journal of Cereal Science 31:25–39).

By eliminating other key starch biosynthesis enzymes, other alterations of the starch biosynthetic pathway can result in useful starches. Several patents exist on the creation and use of such starches (U.S. Pat. Nos. 4,428,972; 4,615,888 4,767,849; 4,789,557; 4,789,738; 4,801,470; 5,009,911; and 5,482,560). More recently, several patents and published applications have described the production and utilization of heterozygous combinations of mutations in the starch biosynthetic pathway to obtain commercially useful starches (W09535026, U.S. Pat. Nos. 5,356,655; 5,502,270; and 5,516,939). The production of many of these starches involves the use of double or triple mutant plants. In these cases in which waxy starch is involved the inventors have stated that "plants homozygous recessive for the waxy gene lack a granule bound starch synthase enzyme and produce nearly 100% amylopectin" (U.S. Pat. Nos. 5,356,655; 5,502,270). Due to the number of mutations required to sufficiently alter the starch (at least 2 or 3 within a single plant) many of these starches are difficult and costly to produce commercially, so many of these starches from plants with mutations in the starch biosynthetic pathway are uncompetitive with chemically modified starches. Further, these combinations of 2 or more mutations, whether they are combined homozygously or heterozygously in the plant endosperm, rely on the alteration of the structure of amylopectin from normal or waxy starch.

Waxy potato starches have been shown to contain an amylose content as low as 0% and as high as 7.9% (Salehuzzaman et al, 1999, Plant, Cell, and Environment 22:1311–1318, van der Leij et al, 1991, Theoretical and Applied Genetics 82:289–295). However, the amylose content of all of these starches is regarded as zero (van der Leij et al, 1991, Theoretical and Applied Genetics 82:289–295). Hovenkamp-Kermelink et al (1987, Theoretical and Applied Genetics 75:217–221) produced a waxy mutant of potato by screening microtubers produced from plants exposed to X-ray radiation. The starch from two micotubers was found to have an amylose content of approximately 5%, but a second generation of tubers produced from additional microtubers from the same irradiated plants resulted in starch with a normal amylose content. Examination of an additional set of tubers resulted in three tubers, two of which stained a solid reddish-brown characteristic of the waxy mutation (Neuffler et al, 1997, Mutants of Maize, Cold Spring Harbor Laboratory Press, Plainview, N.Y., p. 298) and a third which stained a mixture of reddish brown and blue indicating a heterogeneous mixture of waxy starch and amylose-containing starch of unknown quality within the potato tuber. The waxy potatoes did not produce a GBSS enzyme. No distinction was made between these starches with an amylose content below 3.5%. Van der Leij et al (1991, Theoretical and Applied Genetics 75:217–221) observed that potato starches could have an amylose content of between 3% and 7.9% and the tubers would stain red with iodine stain, a primary characteristic of waxy starches. No distinctions were made between these starches having an amylose content between 3% and 7.9%.

Studies have produced antisense transgenic potatoes having amylose contents between 3.0% and 8% (van der Leij et al, 1991, Theoretical and Applied Genetics 82:289–295; Visser et al, 1991, Molecular and General Genetics 225:289–296; Kuipers et al, 1994, Plant Cell 6:43–52) in further attempts to understand the function and activity of GBSS. The amylose contents of these starches were shown to be a result of tubers with both blue and red-brown staining portions (Visser et al, 1991, Molecular and General Genetics 225:289–296), indicating heterogeneous mixtures of waxy starch and amylose-containing starch of unknown quality. Kuipers et al (1994, Plant Cell 6:43–52) also observed heterogeneity on a granule level, with starch granules having blue cores and surrounded by a red-brown colored shell of starch, with the size of the blue core increasing in size with an increase in the amylose content of the starch. Further, the elastic properties and gelling abilities of pastes, and the gel properties of gels produced from these starches low amylose starches are unknown. Studies have attempted to restore the production of amylose in waxy potato plants by transforming the plants with genes for GBSS enzymes produced by other plants. Salehuzzaman et al (1999, Plant Cell and Environment 22:1311–1318) partially restored amylose to amylose free mutants of potato to between 3.5% and 13% amylose by transformation with the cassava GBSS enzyme with different amyloplast transit peptides. For starches between 3.5% and 13% amylose, the starches produced were heterogeneous mixtures of amylose-containing starch and red-brown staining waxy starch: the starch granules had blue cores surrounded by a red-brown colored shell of starch, with the size of the blue core increasing in size with increases in the amylose content of the starch (Salehuzzaman et al, 1999, Plant Cell and Environment 22:1311–1318). Salehuzzaman et al (1999, Plant Cell and Environment 22:1311–1318) additionally observed that a paste of a potato starch with an apparent amylose content of 13% developed an elastic modulus during cooling while a paste of a waxy potato starch did not; the elastic behavior of the heterogeneous starches with lower amylose contents were not reported. Waxy potatoes transformed with GBSS isoforms from pea resulted in potatoes with amylose contents of between 0.8% and 1%, and like the other low amylose potatoes and pea starch, heterogeneity was observed within the granules: granules stained with iodine stain revealed amylose in concentric rings or having blue-staining granule cores (Edwards et al, 2002, The Plant Cell 14:1767–1785). The presence of the amylose produced by pea GBSS was claimed to have an effect on the cooking properties of the starch (Edwards et al, 2002, The Plant Cell 14:1767–1785), however the differences observed between the starches are within the error associated with this type of instrumental measurement. Flipse et al (1996, Theoretical and Applied Genetics 92:121–127) extracted starch from plants produced from crosses between a waxy potato and a normal potato; the potato tubers had varying levels of GBSS activity and no linear correlation was observed between GBSS activity and amylose content. Starches with amylose contents of 2.50%, 16.94%, 18.96%, and 20.32% were examined for their swelling properties and the rheological properties of swollen starch granules. No clear differences of the effect of amylose were observed in the swelling and rheological properties of the granules. The only conclusion that could be made was that the presence of amylose (above 16.94%) had an influence on the physical behavior of the granules.

Thus, in potato, reduction in the amylose content of the starch has resulted in the production of heterogeneous mixtures of amylose containing starch and waxy starch, with heterogeneity among a population of starch granules and within individual starch granules. Further, no distinctions in the physical properties of waxy starches with amylose contents between 0% end 7.9% have been made. Thus, from the existing literature it may be inferred that or potato starch, amylose contents of less then 7.9% confer no unique rheological or pasting properties to these starches outside of those properties observed for either waxy potato or normal potato starch. Further, the elastic properties and gelling abilities of pastes, and the gel properties of gels produced from starches below 13% amylose are unknown, and those tests which have been conducted indicate that the physical properties are within the error associated the physical properties of waxy potato starch or a potato starch with a normal amylose content.

Like the transgenic potato starches, pea mutants producing starch with amylose contents lower than normal pea starch produced granule with blue cores and a red-brown periphery (Denyer et al, 1995, Plant Cell and Environment 18:1019–1026), indicating that they were heterogeneous mixtues of amylose-containing starch and waxy starch. Cooking, paste, and gel behavior was not reported for these starches.

Extensive work initially in Japan has identified waxy wheat starches. The range of amylose content of these waxy mutants was narrow, being approximately 0.5% difference between the highest level and the lowest level reported. In all cases the starch was reported as staining red with iodine and the amylose content was reported as zero or near zero percent. A waxy wheat starch was also created using mutableness of a double-null wheat known as "Ike" to generate a non-null wheat (WO09815621) which stained red when tested with iodine stain. A null allele does not produce a certain protein at that allele on a certain chromosome, and a null mutant does not produce a certain protein at any of the chomosomes. This is in contrast to a non-null mutant which does produce the protein. Further work with transgenic lines has found that disruption of the waxy gene using antisense technology can produce lines lacking in amylose. In all cases these lines were screened for iodine-coloration and red-brown staining starches were found and selected-out of the transformants.

Miura and Sugawara (1996, Theoretical and Applied Genetics 93:1066–1070) have shown that substitution of genes producing functional GBSS enzyme with the null alleles can result in starches with a 22 to 23% amylose content rather than the 25.5% amylose content of the normal control. Likewise, Miura et al (1999, Euphytica 108:91–95) have shown that elimination of the functionality in 2 of the 3 GBSS enzyme isoforms in wheat endosperm results in a wheat starch which has an amylose content of at feast 16% and more often between 20% an 21% of the normal 25% amylose present in the starch. Thus, the presence of one wild type GBSS enzyme is sufficient to produce a starch with an amylose content of at least 16%. Oda ed al (1992, Japanese Journal of Breeding 42:151–154) has shown that low amylose wheat starches having an amylose content between 14.1 and 16.7% can be created through ethyl methanesulphonate (EMS) mutableness of the seeds. Sasaki et al (2000, Cereal Chemistry 77:58–63) produced wheat starches with amylose contents of about 7.5% and 13.5% by crossing normal wheat with waxy wheat. Peak viscosities of all starches differed by less then 20% of the peak viscosity of the waxy wheat starch, with the low amylose starches having a higher peak viscosity than both normal end waxy wheat starch. The gelatinization temperatures and enthalpy were highest for waxy wheats and decreased in the order waxy>13.5% amylose wheat>7.5% amylose wheat>normal wheat starch. The retrogradation temperatures and enthalpy were insignificantly different for waxy wheat, normal wheat, or any of the low amylose wheat starches. From retrogradation data, the inference that these low amylose wheat starches exhibit unique rheological properties could not be made. Further, the elastic properties and gelling abilities of pastes, and the gel properties of gels produced from any of these low amylose starches are unknown. Additionally, in this case since the low amylose trait is not fixed in one wheat line, but instead is the product of tow lines with widely differing amylose contents, the resultant low amylose seed if grown will not produce seeds with one type of low amylose starch but instead will produce a mixture of seeds containing starch having a range amylose contents varying widely between those of the original waxy and normal parents. These starches made from crosses of normal plants and waxy plants are not the subject of the present invention.

Kiribuchi-Otobe et al (1998, Cereal Chemistry 75:671–672) found that starch granules extracted from a wheat strain derived from mutagenized Tanikei A6099 had an apparent amylose content of 1.6% and stained dark brown with dark cores compared to red-staining waxy wheat starch (0.4% apparent amylose). This same wheat was claimed to have an amylose content of 0.8% to 2.5% in U.S. Pat. No. 6,165,535 to presumably account for the approximately 1% error associated with the amylose content assay. Kiribuchi-Otobe et al (1998, Cereal Chemistry 75:671–672) found that this mutant wheat starch had an initial high-temperature viscosity stability relative to a waxy wheat starch (0.4% amylose). However, the viscosity of the starch paste decreased dramatically, to the same viscosity as the waxy wheat, during continued cooking and remained at the same viscosity as waxy wheat after cooking. The mutagenized Tanikei A6099 wheat is known to produce a mutant GBSS enzyme (Yanagisawa et al, 2001, Euphytica 121:209–214), but the effect of the mutation on the activity of the enzyme is not known (Yanagisawa et al, 2001, Euphytica 121: 209–214). Additionally, it is unknown whether the starch contains true amylose, which normally would result in a blue coloration with iodine stain rather than a dark brown stain for this mutant starch, or contains a modified amylopectin structure. The act of mutagenesis itself may have created other mutations in the plant genome which could have additional effects on biosynthesis and thus the cooking properties of the starch (e.g. the amylose-extender mutation in maize), and the structure of amylopectin is also clearly known to have a significant impact on the paste and gel properties of a starch (Jane at al, 1999, Cereal Chemistry 76:629–637). These other enzymes are known to those working in the area of starch biosyntheis, biochemistry, and chemistry. Further, it has been suggested that GBSS may influence the structure of amylopectin a well (Martin and Smith. 1995, The Plant Cell 7:971–985), and a mutation in GBSS could conceivably result in an enzyme which preferentially produces an altered amylopectin rather than synthesize amylose. Thus, alteration of the amylopectin structure of the starch may also affect starch cooking and theological properties. Kiribuchi-Otobe and colleagues (U.S. Pat. No. 6,165,535; Kribuchi-Otobe et al, 1998, Cereal Chemistry75:671–672;Yanagisawa et al, 2001, Euphytia 121:209–214) have not shown that their plants produce an active GBSS nor have they shown that their starch contains amylose and/or produces a normal wheat amylopectin. Further, the elastic properties and gelling abilities of pastes, and the gel properties of gels produced from this low amylose wheat starch are unknown.

Thus, in wheat lines, reduction in the amylose content of the starch has resulted in the production of heterogeneous mixtures of brown-staining starch of unknown amylose and amylopectin quality relative to normal wheat starch. Further, no distinctions in the rheological properties of starches with amylose contents between 1.6% and 15% have been made. Thus, from the existing literature the rheological properties of starches with amylose contents between 1.6% and 15% from hybrid wheat plants are unknown. Some evidence suggests that wheat starches having 7.5% or 13.5% amylose may have some unique cooking properties, but production of these starches was a result of hybridization and recombinations of genetics which cannot be carried uniformly into future generations of material. Further, the elastic properties and gelling abilities of pastes, and the gel properties of gels produced from wheat starches below 1.6% and 15% amylose are unknown.

Low amylose sorghum starches have been shown to contain up to approximately 5% apparent amylose, though these low amylose sorghum starches are commonly referred to as waxy sorghum starches. Horan and Heider (1946, Cereal Chemistry 23:492–503) indicated that some waxy sorghum starches had an amylose content as high as 5%, however they admitted that the method they utilized to determine the amylose contents was primarily used to differentiate waxy from normal sorghum starch and was a rapid method subject to large errors. Miller and Burns (1970, Journal of Food Science 35:666–668) also found waxy sorghums to contain up to approximately 5% amylose, and no distinction was made between this 5% amylose starch and the waxy sorghum starches with amylose contents below 1%. Thus, it may be inferred that for sorghum a small quantity of amylose apparently confers no special cooking or rheological qualities to these starches.

Waxy starches and low amylose rice starches have been shown to contain between 0% and 3% amylose, though collectively these starches are referred to as waxy rice starches (Reyes et al, 1965, Journal of Agricultural and Food Chemistry 13:438–442; Juliano et al, 1969, Journal of Agricultural and Food Chemistry 17:1364–1369; Sanchez et al, 1988, Cereal Chemistry 65:240–243). With these waxy rice starches, it has been assumed that the differing cooking and paste properties of these starches are due to differences in the structure of the amylopectin of the starch rather than the amylose content of the starch (Wang and Wang, 2002, Cereal Chemistry 79:252–256). Thus, it may be inferred from the literature that for rice reduced levels of amylose compared to normal starches confers no special cooking or other rheological qualities to these starches. The effects of amylose and other molecular and compositional characteristics of rice starches on rice (Champagne et al, 1999, Cereal Chemistry 76:764–771; Bett-Garber et al, 2001, Cereal Chemistry 78:551–558) or rice starch properties remain unclear (Lai et al, 2000, Cereal Chemistry 77:272–278).

Low amylose rice starches have been shown to have amylose contents between 7% and 15% (Kumar and Khush, 1988, Euphytica 38:261–269). Shimada et al (1993, Theoretical and Applied Genetics 86:665–672) produced several antisense rice plants with starch having an amylose contents between 6% and 13%. The iodine staining qualities of these starch granules were not reported. Further, any cooking properties of the starches, the elastic properties and gelling abilities of pastes, and the gel properties of gels produced from these low amylose rice starches produced by transgenic rice plants are unknown.

Sano (1984, Theoretical and Applied Genetics 68:467–473) and Sano et al (1986, Euphytica 35:1–9) investigated the effects of two alleles on the gene expression at the waxy locus in rice. The $Wx^b$ allele was shown to relate to ineffective production of GBSS enzyme and amylose, while the $Wx^a$ allele was shown to produce larger quantities of GBSS enzyme and amylose. Villareal et al (1989, Starch 41:369–371) also showed that the $Wx^a$ allele was less effective in the production of amylose than the $Wx^b$ allele based on analysis of 40 rice varieties. Additionally, Isshiki et al (1998, Plant Journal 15: 133–138) observed that for two wild-type rice alleles, $Wx^a$ and $Wx^b$, $Wx^b$ had a GBSS activity ten-fold lower than $Wx^a$ at the protein and mRNA levels. The decrease in the activity of $Wx^b$ compared to $Wx^a$ was the result of a point mutation within the genetic sequence for the normal rice enzyme ($Wx^a$ allele). The $Wx^b$ allele resulted in the synthesis of a 3.4 kilobase pair mRNA transcript compared to a 2.3 kilobase pair mRNA transcript for $Wx^a$ as a result of the inclusion of an intron into the mRNA sequence as a result of the point mutation. Starch produced from rice plants was related to the ability of the plant to excise the intron from the mRNA sequence. Plants which expressed high levels of mature mRNA (without intron 1) and no pre-mRNA (containing intron 1) produced the highest levels of GBSS protein and the highest levels of amylose (20.0 to 27.8% amylose). With more balanced expression of mature and pre-mRNA, lower levels of GBSS protein and amylose were observed (6.7 to 16.0% amylose). When all of the mRNA contained intron 1, and no mature mRNA was observed, no GBSS protein was observed and no amylose was detected (Wang et al, 1995, Plant Journal 7:613–622). This pattern relating amylose content to mature mRNA with properly-excised intron 1 could be applied across 31 different rice cultivars (Wang et al, 1995, Plant Journal 7:613–622). Thus based on the work of Shimada et al (1993, Theoretical and Applied Genetics 86:665–672), Isshiki et al (1998, Plant Journal 15: 133–138), and Wang et al (1995, Plant Journal 7:613–622), low amylose rice appears to be the result of a decrease in the amount of normal GBSS through a mutation which results in problems with mRNA processing rather than due to a mutation in the mature mRNA sequence. Further, no clear relationships exist between rice and rice starch properties and amylose content.

Waxy corn starches are considered to stain red by iodine stain according to the Maize Genome Database [supported by the United States Department of Agriculture, Agricultural Research Service (USDA-ARS), the National Science Foundation (NSF), and the University of Missouri]. Numerous dominant mutant alleles producing an active GBSS protein (Table 1) and recessive mutant alleles producing waxy starch (Table 2) exist. In maize, it is well known that increasing the dosage of the wx mutation in the endosperm of the seeds decreases the amylose content of the starch, but seeds with 2 doses of the wx mutation (out of a possible 3 in the triploid endosperm) produce a starch with an apparent amylose content near 18% in the mature seed compared to 23–25% amylose in the starch isolated from normal seed (Sprague et al, 1943, Journal of the American Society of Agronomy 35, 817–822; Boyer et al, 1976, Journal of Heredity 67:209–214).

TABLE 1

Dominant mutant alleles of Waxy (Wx)

| | | | |
|---|---|---|---|
| Wx1-m8-r10 | Wx1-m8r1 | Wx1-m8r2 | Wx1-m9-r3 |
| Wx1-m9-r4 | Wx1-m9r1 | Wx1-Mo17 | Wx1-Mt42 |
| Wx1-N28(Ht) | Wx1-NC258 | Wx1-NC268 | Wx1-NC296 |
| Wx1-NC298 | Wx1-NC300 | Wx1-NC304 | Wx1-Oh07B |
| Wx1-Oh40B | Wx1-Oh43 | Wx1-Os420 | Wx1-P39 |
| Wx1-Pa91 | Wx1-R177 | Wx1-R213 | Wx1-R4 |
| Wx1-RobA | Wx1-SA24 | Wx1-SC213 | Wx1-SC76 |
| Wx1-SG1533 | Wx1-T218 | Wx1-T232 | Wx1-T8 |
| Wx1-Tx303 | Wx1-Tx601 | Wx1-U267Y | Wx1-Va102 |
| Wx1-Va22 | Wx1-Va35 | Wx1-Va59 | Wx1-Va99 |
| Wx1-W117Ht | Wx1-W153R | Wx1-W182B | Wx1-W22 |
| Wx1-W22Cs | Wx1-W23 | Wx1-W64A | Wx1-WF9 |
| Wx1-Wf9 | Wx1 | Wx1-38-11 | Wx1-A |
| Wx1-A12 | Wx1-A188 | Wx1-A554 | Wx1-A619 |
| Wx1-A632 | Wx1-A634 | Wx1-A635 | Wx1-A641 |
| Wx1-B14A | Wx1-B164 | Wx1-C49A | Wx1-B2 (Missouri) |
| Wx1-B52 | Wx1-B68 | Wx1-B73 | Wx1-B37 |
| Wx1-B77 | Wx1-B84 | Wx1-B95 | Wx1-B76 |
| Wx1-C103 | Wx1-C11 | Wx1-C123 | Wx1-B97 |
| Wx1-Cl187-2 | Wx1-Ky228 | Wx1-CM37 | Wx1-CM105 (Canada) |
| Wx1-CO159 | Wx1-D940Y | Wx1-DE811 | Wx1-CMV3 |
| Wx1-EP1 | Wx1-F2 | Wx1-F2834T | Wx1-E2558W |
| Wx1-GT112 | Wx1-GT119 | Wx1-H95 | Wx1-F44 |
| Wx1-HP301 | Wx1-HY | Wx1-Hy | Wx1-H99 |
| Wx1-I205 | Wx1-I29 | Wx1-IA2132 | Wx1-I137TN |
| Wx1-IDS91 | Wx1-IL677A | Wx1-K55 | Wx1-IDS28 |
| Wx1-Ki14 | Wx1-Ky21 | Wx1-Ky226 | Wx1-K64 |
| Wx1-L317 | | | |

TABLE 2

Recessive mutant alleles of waxy (wx)

| | | | |
|---|---|---|---|
| wx1-m7::Ac7 | wx1-m7::inactive | wx1-m8::Spm-I8 | wx1-m8311B::Ds |
| wx1-m844::En1 | wx1-m86246x | wx1-m9::Ac | wx1-m9::Ds |
| wx1-m9::Ds-cy | wx1-mCs10::Ds | wx1-mCS13::Ds | wx1-mCS14::Ds |
| wx1-mCS15::Ds | wx1-mCS16::Ds | wx1-mCS17::Ds | wx1-mCS18::Ds |
| wx1-mCS19::Ds | wx1-mCS20::Ds | wx1-mCS22::Ds | wx1-mCS23::Ds |
| wx1-mCS24::Ds | wx1-mCS7::Ds | wx1-mCS8::Ds | wx1-mCS9::Ds |
| wx1-Mo17 | wx1-Mum1 | wx1-Mum10 | wx1-Mum11 |
| wx1-Mum2 | wx1-Mum3 | wx1-Mum4 | wx1-Mum5::Mu |
| wx1-Mum6 | wx1-Mum7 | wx1-Mum8 | wx1-Mum9 |
| wx1-Mus16 | wx1-Mus181 | wx1-Mus215 | wx1-N1050A |
| wx1-N1240A | wx1-P60 | wx1-R | wx1-S15 |
| wx1-S5 | wx1-S9 | wx1-Stonor | wx1 |
| wx1-11 | wx1-12 | wx1-21 | wx1-84-4 |
| wx1-90 | wx1-a | wx1-Alexander | wx1-B |
| wx1-B1 | wx1-F | wx1-B3-S1 | wx1-B2::TouristA |
| wx1-B3r | wx1-B4::Ds2 | wx1-B5 | wx1-B6 |
| wx1-B7 | wx1-B73 | wx1-B8 | wx1-BL2 |
| wx1-BL3 | wx1-C | wx1-c | wx1-C1 |
| wx1-C2 | wx1-C3 | wx1-C31 | wx1-C34 |
| wx1-C4 | wx1-CY | wx1-B3::Ac | wx1-Ds6(U66842) |
| wx1-G | wx1-H | wx1-H21 | wx1-I |
| wx1-J | wx1-M | wx1-L | wx1-K::Hopscotch |

TABLE 2-continued

Recessive mutant alleles of waxy (wx)

| | | | |
|---|---|---|---|
| wx1-m1::Ds | wx1-m32::Bg | wx1-m6R | wx1-m5:8313delta14 |
| wx1-m6-o1 | wx1-m6::Ds | wx1-m6NR | wx1-m5:8313::Ds |

In the early 1940's, a waxy mutant (wx$^a$) was discovered in two exotic Argentinian small-seeded flint corn varieties which contained a starch which had an amylose content of 2.4% (Brimhall et al, 1945, Journal of the American Society of Agronomy 37:937–944). The starch stained a pale violet color (Brimhall et al, 1945, Journal of the American Society of Agronomy 37:937:944). Additionally, the amylose content of the starch increased from 0% (waxy) to 0.65% to 1.3% to 2.4% (full wx$^a$) with increasing dose of the trait when the plant bearing the starch was crossed with a waxy plant (Brimhall et al, 1945, Journal of the American Society of Agronomy. 37:937–944; Sprague and Jenkins, 1948, Iowa State College Journal of Science 22: 205–213). Echt and Schwartz (1981, Maize Genetics Cooperation Newsletter 55:8–9) described the wx-a allele as resulting in a 95% reduction in the amount of GBSS protein produced and a starch with a low amylose content. Examination of cooked starch showed that the viscosity of the paste decreased in the order waxy>waxy×wx$^a$>wx$^a$×waxy>wx$^a$, where waxy is the female in the sample waxy×wx$^a$, and wx$^a$ is the female in the sample wx$^a$×waxy. In a comparison between wx$^a$ and normal starch, the viscosity of cooked starch increased in the order normal<normal×wx$^a$<wx$^a$×normal<wx$^a$. Thus in these experiments examining the viscosity of cooked pastes, wx$^a$ starch was shown to have a lower viscosity than waxy starch and to have a higher viscosity than normal starch. The elastic properties and gelling abilities of pastes, and the gel properties of gels produced from this low amylose starch are unknown. Further, the specific mutation resulting in this trait is unknown.

Low amylose barley starches have been shown to contain up to approximately 5% apparent amylose, though these starches are commonly referred to as waxy barley starches (Tester and Morrison, 1992, Cereal Chemistry 69:654–658). However, this apparent amylose is due to a mixture of starch granules in the starch storing organ of the barley plant. The amylose content of the granules typically ranges from an undetectable level up to approximately 0%, with the granules having the highest amylose content existing closest to the surface of the seed (Andersson et al, 1999, Journal of Cereal Science 30:165–171). Recent work with waxy barley starch teaches that starches with amylose contents up to 6.44% amylose, (Li et al, 2001, Food Chemistry 74:407–415). Of these barley starches with less than 6.44% amylose, the starch with no amylose developed viscosity most rapidly, and those with a higher amylose content were delayed in peak viscosity development. Additionally, all of the waxy barley starches began to develop viscosity at a similar point in the cooking process (time and temperature). No further rheological analysis was conducted on these starches.

The size and morphology of starch granules and starch molecules produced by a plant of a specific species are characteristic of that species (Jane et al, 1994, Starch/Stärke 46:121–129). Since the physical properties of a starch are due to the overall physical composition and structure of starch granules, exact relationships between one physical attribute of a starch to the precise cooking behavior of the starch are difficult to predict. These differences in granules are also accompanied by species-specific qualities of the lipids contained within the starch granules (Morrison, 1988, Journal of Cereal Science 8:1–15; Tester and Morrison, 1992, Cereal Chemistry 69:654–658), the species-specific structure of the amylopectin (Jane et al, 1999, Cereal Chemistry 76:629–637), and the species-specific size and structure of the amylose (Takeda et al, 1987, Carbohydrate Research 165:139–145; Hizukuri et al, 1981, Carbohydrate Research 94:205–213; Takeda et al, 1989, Cereal Chemistry 66:22–25; Takeda et al, 1986, Carbohydrate Research 148: 299–308; Takeda et al, 1984, Carbohydrate Research 132: 83–92). It is equally well known that starch physical behavior is dependent on all of these properties (Gidley and Bulpin, 1989, Macromolecules 22:341–346; Eliasson and Kim, 1995, Journal of Rheology 39:1519–1534; Klucinec and Thompson, 1998, Cereal Chemistry 75:887–896; Klucinec and Thompson, 1999, Cereal Chemistry 76:282–291; Jane et al, 1999, Cereal Chemistry 76:629–637; Klucinec and Thompson, 2002a, Cereal Chemistry, 79:19–23; Klucinec and Thompson, 2002b, Cereal Chemistry, 79:24–35). This point is illustrated by the desirability of waxy potato starch with an amylose content below 1% over waxy maize starch because of the better heat stable viscosity of the waxy potato starch in some high-temperature baking applications (EP1102547).

Because of the differences in the physical structure and composition of starches from different plant species, it is difficult to predict whether a specific relationship observed between the structure or composition of a starch and its cooking and rheological properties in one plant species will be observed if the structure and composition are reproduced in another plant species. However, across starches isolated from various plant species the effects of the absence of amylose are clear as a result of comparing waxy starches to normal starches: normal starches have the ability to form elastic gels while waxy starches form stable viscous pastes. These properties of normal and of waxy starches have been recognized in the literature. However, the relationship between the presence/absence of lower amounts of amylose on the gelling and rheological qualities of starches is unclear. Further, the interaction between the number of different starch enzymes involved in starch biosynthesis remains unclear. Further, few examples of starch with amylose contents between 1.5% and 15% which are not heterogeneous mixtures of waxy starch and amylose-containing starch exist. Even further, the general value and application of these starches in products has not been recognized: they have not been characterized for their paste and gel properties and how gels of these starches develop from pastes.

Introduction of traits into new plant lines may be accomplished by traditional breeding practices, a process which is initiated by crossing a plant line with the trait with a target plant line without the trait (a converted line). The crossing, however, also produces an entirely new combination of genes within the chromosomes of the resultant plant containing the trait. Thus, the identity and agronomic characteristics of the original plant lines are signficantly altered. Agronomic traits are often multigenic and in many plant species these traits are furher complicated by multiple sets of chromosomes. Reconstruction of the converted plant line to its original genetic state but containing the new trait takes time and a number of crosses, and even after a number of crosses the genetics of the converted line will contain some residual from the original plant line containing the trait. Thus, the new plant is not equivalent to the unconverted parent with the new trait.

Clearly the corn breeding industry is aware of a method of producing mutations in corn and that these mutations have an effect on the processing characteristics of the resultant starch. Chemical mutagens such as ethyl methane sulfonate (EMS) produce a mutation in the genome. A method of EMS pollen mutation was published by Neuffer as early as 1971 (Neuffer, 1971, Maize Genetics Cooperation Newsletter 45:146–149). EMS mutableness may also result in more complex lesions in the plant genome (Okagaki et al, 1991, Genetics 128:425–431). Another method of producing mutations is to use the transposon tagging to form a mutation in a nucleic acid sequence. This method does not form a point mutation. This method was used by Iowa State University to produce a dominant form of amylose-extender in corn. At ISU, researchers made a surprising discovery that is evidenced in U.S. Pat. No. 5,004,864 that through transposon-tagging technology a dominant amylose-extender gene could be created. The Iowa State researchers' dominant gene produces kernels within the 70% apparent amylose region as would be expected. The patent indicates that due to the dominant nature of the gene that in fact the addition of doses of mutant in the kernel do not increase the level of apparent amylose produced by the plant. Both processes share the advantage that the original genetics of the parent are largely retained after incorporation of the new trait. A plant which is essentiall identical to the parent plant is an isogenic line. Isogenic lines are lines with essentially identical genes. Introducing a new trait into a plant using mutableness avoids conventional breeding problems since it does not produce an entirely new combination of genes within the chromosomes of the new plant. Though the result of mutableness is nearly isogenic to the parent line with the exception of the introduced trait, the introduction of new traits by mutableness is not straightforward. Successful introduction of the trait involves screening thousands of mutagenized seed for each plant line; fortunately, some traits can be identified by the phenotype of the starch storing organ (e.g. a seed for maize) and screening can be accelerated.

It is known that the activity and action of enzymes can be altered, not simply eliminated, through mutableness. For example, maize starch synthase (SS) SSIIa (SEQ ID NO:8) and SSIIb-2 (SEQ ID NO:7) have been site specific mutagenized (Imparl-Radosevich et al, 1999, FEBS Letters 457:357–362; Nichols et al, 2000, Biochemistry 39:7820–7825). Mutants with much reduced activity or lower affinity for ADPG were obtained (Tables 4 through 6).

TABLE 4

Kinetics for SSIIb-2[a] and mutants

| Enzyme[b] | ADPGlc kinetics[c] | | | | Primer kinetics[c] | | | |
|---|---|---|---|---|---|---|---|---|
| | Glycogen as primer | | Amylopectin as primer | | Glycogen as primer | | Amylopectin as primer | |
| | $V_{max}$ | $K_m$ | $V_{max}$ | $K_m$ | $V_{max}$ | $K_m$ | $V_{max}$ | $K_m$ |
| SSIIb-2 | 118.99 ± 5.06 | 0.13 ± 0.02 | 74.86 ± 5.46 | 0.16 ± 0.03 | 97.93 ± 2.97 | 0.05 ± 0.01 | 76.06 ± 3.55 | 0.16 ± 0.04 |
| D21N | 4.87 ± 0.25 | 1.48 ± 0.03 | 2.77 ± 0.26 | 1.58 ± 0.11 | 4.31 ± 0.31 | 0.28 ± 0.03 | 3.51 ± 0.69 | 0.51 ± 0.09 |
| D21E | 13.35 ± 1.32 | 0.12 ± 0.02 | 9.30 ± 0.79 | 0.13 ± 0.03 | 14.01 ± 0.61 | 0.21 ± 0.03 | 9.86 ± 0.49 | 0.23 ± 0.04 |
| D139E | 25.25 ± 1.88 | 0.07 ± 0.02 | 22.27 ± 2.97 | 0.09 ± 0.03 | 30.51 ± 1.51 | 0.08 ± 0.01 | 24.85 ± 1.99 | 0.07 ± 0.02 |
| E391D | 17.16 ± 1.89 | 1.18 ± 0.14 | 15.05 ± 1.32 | 1.37 ± 0.14 | 15.05 ± 1.32 | 0.63 ± 0.06 | 7.44 ± 1.03 | 0.68 ± 0.07 |

[a]SSIIb-2 is an N-terminally truncated form of mSSIIb produced in E. coli.
[b]Mutant enzyme designations are based upon the change in the amino acid sequence. The first letter and number corresponds to an amino acid and its location in the sequence of non-mutant enzyme, respectively, and the final letter refers to the amino acid replacing the non-mutant amino acid in the sequence of the mutant enzyme.
[c]$V_{max}$ values are expressed as mol Glucose/min/mg. For ADPGlc kinetics, $K_m$ values are expressed as mM ADPGlc, glycogen concentration was 20 mg/ml, and amylopectin concentration was 5 mg/ml. For primer kinetics, $K_m$ values are expressed as mg/ml primer. For SSIIb-2, D21E, and D139E 1 mM ADPGlc was used, and 5 mM ADPGlc was used for D21N and E391D.

TABLE 5

Starch synthase activity of SSIIa mutants as measured in crude E. coli extract.

| Enzyme[a] | specific activity (nmol/min/mg) | % activity of control |
|---|---|---|
| Wild Type | 399 | 100 |
| R210Q | 420 | 105 |
| R211Q | 90 | 22 |
| R211K | 164 | 41 |
| R211E | 15 | 4 |
| H213A | 41 | 10 |
| H213K | 36 | 9 |
| H213W | 41 | 10 |
| H213N | 92 | 23 |
| R214Q | 97 | 24 |
| R214K | 300 | 75 |
| R214E | 22 | 6 |
| R221Q | 237 | 59 |
| R269Q | 375 | 94 |
| R284Q | 276 | 69 |
| R492Q | 335 | 84 |
| R567Q | 423 | 106 |

[a]Mutant enzyme designations are based upon the change in the amino acid sequence. The first letter and number corresponds to an amino acid and its location in the sequence of non-mutant enzyme, respectively, and the final letter refers to the amino acid replacing the non-mutant amino acid in the sequence of the mutant enzyme.

TABLE 6

Kinetics for Maize SSIIa wild type and mutants[a] K193R, K193Q, K193E and K497Q

| Enzyme | Amylopectin as primer | | | Glycogen as primer | | |
|---|---|---|---|---|---|---|
| | $V_{max}$[b] | $K_m$ for ADPG[c] | $K_m$ for amylopectin[d] | $V_{max}$ | $K_m$ for ADPG | $K_m$ for glycogen |
| wild-type | 49.9 ± 4.06 | 0.11 ± 0.01 | 0.20 ± 0.037 | 34.47 ± 1.70 | 0.12 ± 0.01 | 0.17 ± 0.03 |
| K193R | 18.2 ± 0.91 | 0.15 ± 0.01 | 0.525 ± 0.03 | 42.27 ± 3.01 | 0.15 ± 0.02 | 0.68 ± 0.03 |
| K193Q | 17.4 ± 1.58 | 0.13 ± 0.01 | 0.12 ± 0.008 | 6.20 ± 0.01 | 0.10 ± 0.01 | 0.11 ± 0.02 |
| K193E | 10.53 ± 0.5 | 0.22 ± 0.01 | 0.72 ± 0.052 | 25.45 ± 0.08 | 0.17 ± 0.02 | 0.52 ± 0.05 |
| K497Q | 13.5 ± 0.21 | 5.62 ± 0.23 | 1.27 ± 0.17 | 23.8 ± 2.5 | 6.91 ± 0.33 | 2.83 ± 0.08 |

[a]Mutant enzyme designations are based upon the change in the amino acid sequence. The first letter and number corresponds to an amino acid and its location in the sequence of non-mutant enzyme, respectively, and the final letter refers to the amino acid replacing the non-mutant amino acid in the sequence of the mutant enzyme.
[b]$V_{max}$ values are in μmol/min/mg protein.
[c]$K_m$ for ADP-glucose (ADPG) are expressed in mM ADP-glucose.
[d]$K_m$ for primer (amylopectin and glycogen) are expressed as mg/ml primer.

From such prior mutableness work, it might be expected that mutations could give rise to an alteration in amylose content. However, based on what is known in the literature the invention and finding disclosed and reported herein of a waxy starch with altered rheological properties could not be expected.

Known cloning techniques may be used to provide the DNA constructs to produce an enzyme or protein. Potential donor organisms are screened and identified. Thereafter there can be two approaches: (a) using enzyme purification and antibody/sequence generation or (b) using cDNAs as heterologous probe to identify the genomic DNAs for enzymes in libraries from the organism concerned. Gene transformation, plant regeneration and testing protocols are known to the art. In instances in which the transgene codes for a starch biosynthetic enzyme it is necessary to make nucleic acid sequence constructs for transformation which also contain regulatory sequences that ensure expression during starch formation. These regulatory sequences are present in many grains and in tubers and roots. For example these regulatory sequences are readily available in the maize endosperm as DNA encoding Starch Synthases (SS or GBSS) or Branching Enzymes (BE) or other maize endosperm starch synthesis pathway enzymes. These regulatory sequences from the endosperm ensure protein expression at the correct developmental time (e.g., ADPG pyrophosphorylase).

In the area of polysaccharide enzymes there are reports of vectors for engineering modification in the starch pathway of plants by use of a number of starch synthesis genes in various plant species. That GBSS enzymes make amylose is well known. One specific patent example of the use of a polysaccharide enzyme shows the use of mutants in GBSS enzymes to modify plant starch. Publications such as WO9211376, JP04104791, EP788735, WO09827212, WO028052, which teach vectors containing DNA to control the activity of GBSS biosynthetic enzymes within plant cells are available. Specifically, these publications refer to the changes in potato starch due to the introduction of these enzymes. Other starch synthesis genes and their use have also been reported to change starch though generally these are not directly focused on changing amylose content.

Once the ligated DNA which encodes the hybrid polypeptide is formed, then cloning vectors or plasmids are prepared which are capable of transferring the DNA to a host for expressing the hybrid polypeptides. The recombinant nucleic acid sequence of this invention is inserted into a convenient cloning vector or plasmid. For starch biosynthetic enzymes the preferred host is often a starch granule-producing host. However, bacterial hosts can also be employed. Especially useful are bacterial hosts that have been transformed to contain some or all of the starch-synthesizing genes of a plant. The ordinarily skilled person in the art understands that the plasmid is tailored to the host. For example, in a bacterial host transcriptional regulatory promoters include lac, TAC, trp and the like. Additionally, DNA coding for a transit peptide most likely would not be used and a secretory leader that is upstream from the structural nucleic acid sequence may be used to get the polypeptide into the medium. Alternatively, the product is retained in the host and the host is lysed and the product isolated and purified by starch extraction methods or by binding the material to a starch matrix (or a starch-like matrix such as amylose or amylopectin, glycogen or the like) to extract the product.

The preferred host is a plant and thus the preferred plasmid is adapted to be useful in a plant. The plasmid should contain a promoter, preferably a promoter adapted to target the expression of the protein in the starch-containing tissue of the plant. The promoter may be specific for various tissues such as seeds, roots, tubers and the like; or, it can be a constitutive promoter for nucleic acid sequence expression throughout the tissues of the plant. Well-Known promoters include the 10KD zein (maize) promoter, the CAB promoter, patatin, 35S and 19S cauliflower mosaic virus promoters (very useful in dicots), the polyubiquitin promoter (useful in monocots) and enhancement and modifications thereof known to the art.

The cloning vector may contain coding sequences for a transit peptide to direct the plasmid into the correct location. Coding sequences for other transit peptides can be used. Transit peptides naturally occurring in the host to be used are preferred. The purpose of the transit peptide is to target the peptide to the correct intracellular area.

The donor nucleic acid sequence(s) are incorporated into the genome of the recipient plant by transformation. Any method suitable for the target plant may be employed. Numerous transformation procedures are known from the literature such as agroinfection using *Agrobacterium tumefaciens* or its Ti plasmid, electroporation, microinjection of plant cells and protoplasts, microprojectile transformation pollen tube transformation, and "whiskers" technology (U.S. Pat. Nos. 5,302,523 and 5,464,765) to mention but a few. Reference may be made to the literature for full details of the known methods. The transformed cells may then be regenerated into whole transgenic plants in which the new nuclear material is stably incorporated into the genome. Methods of regenerating plants are known in the art. Both transformed monocot and dicot plants may be obtained in this way, although the latter are usually more easy to regenerate. Once the host is transformed and the proteins expressed therein, the presence of the DNA encoding the payload polypeptide in the host is confirmable. The presence of expressed proteins may be confirmed by Western Blot or ELISA or as a result of a change in the plant or the cell.

The present invention provides for generating unexpected and valuable traits in all recipient plants producing or storing starch. The recipient plant may be: a cereal such as maize (corn), wheat, rice, sorghum or barley; a fruit-producing species such as banana, apple, tomato or pear; root or tuber crops such as cassava, potato, yam or turnip; an oilseed crop such as rapeseed, sunflower, oil palm, coconut, linseed or groundnut; a meal crop such as soya, bean or pea; or any other suitable species. Preferably the recipient plant is of the family Gramineae and most preferably of the species *Zea mays*.

The present invention provides for methods for generating unexpected and beneficial traits in all mutant recipient plants producing or storing starch. The mutant or multiple-mutant recipient plant may be: a cereal such as maize (corn), wheat, rice, sorghum or barley; a fruit-producing species such as banana, apple, tomato or pear; a root crop such as cassava, potato, yam or turnip; an oilseed crop such as rapeseed, sunflower, oil palm, coconut, linseed or groundnut; a meal crop such as soya, bean or pea; or any other suitable species. Preferably the mutant or multiple-mutant recipient plant is of the family Gramineae and most preferably of the species *Zea mays*.

The present invention provides methods for generating beneficial traits in all donor plants producing or storing starch. The donor plant may be: a cereal such as maize (corn), wheat, rice, sorghum or barley; a fruit-producing species such as banana, apple, tomato or pear; a root crop such as cassava, potato, yam or turnip; an oilseed crop such as rapeseed, sunflower, oil palm, coconut, linseed or groundnut; a meal crop such as soya, bean or pea; or any other suitable species. Preferably the donor plant is of the family Gramineae and most preferably of the species *Zea mays*.

The present invention provides methods for generating beneficial traits in all plants by methods of biotechnology and plant transformation. Those with ordinary skill in the art will recognize that there are several ways of affecting amylose content in a plant.

A continuing need to develop starches with improved rheological properties exists. In particular, there is an interest in the development of starches which as pastes have a high viscosity and have substantial elastic character. Such properties would be beneficial in food formulations including pies, puddings, soups, yoghurts, sauces, and other foodstuffs as viscosity builders and suspension aids. Further, such starches could be used for coatings and films in foodstuffs such as batter coatings. Once deposited on a surface, a paste of the elastic starch will have a better tendency than existing starches to cling and adhere to a surface rather than flow with gravity.

The present invention provides a starch storing organ which produces starch which has unique cooking, thickening, and/or gelling properties (herein referred to as an elastic waxy or waxy-E or wx-E starch). The starch storing organs of the present invention are characterized as producing a mutant but active granule-bound starch synthase. The starch of the present invention has a low amylose content. The properties of the starches have value in a variety of uses and applications. The starch granules described herein were isolated from starch storage organs from plants which contain a mutant but active granule-bound starch synthase present in the starch storing organ, have an amylose content between 1.5 and 15%, and most preferably an amylose content between 1.5 and 10% and even more preferably an amylose content between 2% and 8%, and stain blue or purple with iodine stain.

In the present invention mutableness was utilized to develop starch-containing plants which produce a mutant but active granule-bound starch synthase in starch storage organs and which produce starches which have unique cooking, thickening, and gelling properties and which also stain blue with iodine stain and have a low amylose content. Examination of the cooking, thickening, and gelling properties of the starch recovered from mutant plants was utilized to identify starches which had waxy-E character. Genotypes which showed GBSS activity and a low amylose content are also provided herein. These genotypes may be used to screen for new mutant enzymes or for recombinations of starch synthesizing enzymes using other methods.

The present invention provides a starch which has unique cooking, thickening, and gelling properties and which also stains blue with iodine stain and has a low amylose content. The present invention further provides a method of producing the disclosed starch. The present invention provides methods of producing and identifying useful variants of plants which produce a starch with a unique functionality and having a low amylose content as a result of variants of an enzyme. The nucleic acid sequences for any such starch synthesizing enzymes may be used in constructs according to this invention.

The present invention provides for a starch that has unique cooking, thickening, and/or gelling properties.

The present invention provides a method which results in a plant with the characteristic of containing a mutation that results in reduced but detectable amylose synthesis when compared to the wildtype.

The present invention provides a method which results in a plant with the characteristic of containing a mutation that results in reduced but decteable GBSS enzyme activity when compared to the wildtype.

The present invention provides a starch that as a result of mutableness stains blue or bluish-purple with the application of iodine stain and has a low amylose content.

The present invention provides a starch from a commercially-viable plant line.

The present invention provides a method for crossing a plant producing a starch of the present invention with a second plant producing starch of the present invention to produce starch storing organs that produce a starch of the present invention. The resultant propagative structures from said crossing may be grown to produce starch storing organs which contain starch of the present invention.

Alternatively, the present invention provides for crossing a plant producing a starch of the present invention with a waxy plant to produce starch storing organs that produce a starch of the present invention. The resultant propagative structures from the crossing may be grown to produce starch storing organs which contain starch of the present invention.

Additionally, the present invention provides for crossing a plant which has at least one plant which produces starch of the present invention in its genetic history with a plant producing starch of the present invention or any other plant. The resultant propagative structures may be grown in a subsequent season to produce starch producing organs which contain starch of the present invention.

The present invention invention also provides for transformation of plants into plants which produce starch of the present invention.

The present invention provides a starch which after gelatinization or pasting has a higher elastic modulus than pastes of waxy starch and lower than normal starch.

In the preferred embodiment, the starch is from a maize plant.

In other embodiments, the plant is a potato, wheat, rice, or barley plant.

In one embodiment, the starches of the present invention will have at strains below the yield strain an elastic modulus greater than waxy starch, or preferably have an elastic modulus at least 2 times that of waxy starch, or even more preferably an elastic modulus greater than 10 Pa, or even more preferably an elastic modulus greater than 15 Pa, or most preferably an elastic modulus greater than 20 Pa, or further an elastic modulus between 10 and 100 Pa, or even further between 15 and 60 Pa, or further between 20 and 50 Pa when starches of the present invention are cooked as a suspension of 5% starch (dry weight %) in pH 6.5 phosphate buffer using a Rapid Visco Analyzer 4 and using the instrument conditions specified in the Newport Scientific Standard 1 Version 5 (December 1997) heating and stirring program, and when the resultant paste is stored for 24 hours at 25° C. before measurement.

In another embodiment, the starches of the present invention will have at strains below the yield strain an elastic modulus greater than waxy starch, or preferably have an elastic modulus at least 2 times that of waxy starch, or even more preferably an elastic modulus greater than 10 Pa, or even more preferably an elastic modulus greater than 15 Pa, or most preferably an elastic modulus greater than 20 Pa, or further an elastic modulus between 10 and 100 Pa, or even further between 15 and 60 Pa, or further between 20 and 50 Pa when starches of the present invention are cooked as a suspension in pH 6.5 phosphate buffer using a Rapid Visco Analyzer 4 and using the Newport Scientific Standard 1

Version 5 (December 1997) heating and stirring program, when the concentration of the starch is such that a paste of waxy starch at the same concentration has a final viscosity of between 600 and 850 centipoise, and when the resultant paste is stored for 24 hours at 25° C. before measurement.

In a further embodiment, the starches of the present invention when incorporated into a food product will have at strains below the yield strain an elastic modulus greater than the elastic modulus of a product made with an identical amount of a waxy starch, or preferably an elastic modulus at least 2 times that of an identically made and formulated product made with an identical amount of waxy starch, or more preferably an elastic modulus at least 3 times that of a product identically made and formulated with an identical amount of waxy starch.

In an additional embodiment, the starches of the present invention when incorporated into a food product will have at strains below the yield strain a phase angle less than the phase angle of a product identically made and formulated with an identical amount of waxy starch, or preferably have a phase angle at most 75% that of waxy starch, or even more preferably a phase angle less than 15 degrees, or most preferably a phase angle less than 7 degrees.

The present invention provides a starch which after gelatinization or pasting has a higher gel-like character than pastes of waxy starch.

In the preferred embodiment, the starch is from a maize plant.

In other embodiments, the plant is a potato, wheat, rice, or barley plant.

In another embodiment, starches of the present invention will have at strains below the yield strain a lower phase angle than waxy starch, or preferably have a phase angle less than 12 degrees, or even more preferably a phase angle less than 10 degrees, or most preferably a phase angle less than 6 degrees when starches of the present invention are cooked as a suspension of 5% starch (dry weight %) in pH 6.5 phosphate buffer using a Rapid Visco Analyzer 4 and using the instrument conditions specified in the Newport Scientific Standard 1 Version 5 (December 1997) heating and stirring program, and when the resultant paste is stored for 24 hours at 25° C. before measurement.

In another embodiment, starches of the present invention will have at strains below the yield strain a lower phase angle than waxy starch, or preferably have a phase angle less than 12 degrees, or even more preferably a phase angle less than 10 degrees, or most preferably a phase angle less than 6 degrees when starches of the present invention are cooked as a suspension in pH 6.5 phosphate buffer using a Rapid Visco Analyzer 4 and using the Newport Scientific Standard 1 Version 5 (December 1997) heating and stirring program, when the concentration of the starch is such that a paste of waxy starch at the same concentration has a final viscosity of between 600 and 850 centipoise, and when the resultant paste is stored for 24 hours at 25° C. before measurement.

In one embodiment, starches of the present invention will have at strains below the yield strain an increase in G' proportionally less than waxy starch with an increase in oscillatory frequency, or preferably increase less than 3 fold as the frequency is increased from 0.1 to 100 rad/s oscillatory frequency at a testing strain below the yield strain, or even more preferably increase less than 40 Pa as the frequency is increased from 0.1 to 100 rad/s oscillatory frequency at a testing strain below the yield strain, or most preferably increase less than 30 Pa as the frequency is increased from 0.1 to 100 rad/s oscillatory frequency at a testing strain below the yield strain when starches of the present invention are cooked as a suspension of 5% starch (dry weight %) in pH 6.5 phosphate buffer using a Rapid Visco Analyzer 4 and using the instrument conditions specified in the Newport Scientific Standard 1 Version 5 (December 1997) heating and stirring program, and when the resultant paste is stored for 24 hours at 25° C. before measurement.

In another embodiment, starches of the present invention will have at strains below the yield strain an increase in G' proportionally less than waxy starch with an increase in oscillatory frequency, or preferably increase less than 3 fold as the frequency is increased from 0.1 to 100 rad/s oscillatory frequency at a testing strain below the yield strain, or even more preferably increase less than 40 Pa as the frequency is increased from 0.1 to 100 rad/s oscillatory frequency at a testing strain below the yield strain, or most preferably increase less than 30 Pa as the frequency is increased from 0.1 to 100 rad/s oscillatory frequency at a testing strain below the yield strain when starches of the present invention are cooked as a suspension in pH 6.5 phosphate buffer using a Rapid Visco Analyzer 4 and using the Newport Scientific Standard 1 Version 5 (December 1997) heating and stirring program, when the concentration of the starch is such that a paste of waxy starch at the same concentration has a final viscosity of between 600 and 850 centipoise, and when the resultant paste is stored for 24 hours at 25° C. before measurement.

In a further embodiment, the starches of the present invention when incorporated into a food product will at strains below the yield strain have an oscillatory frequency dependence less than food products formulated and made identically with waxy starch and have an oscillatory frequency dependence greater than or equivalent to normal starch.

The present invention provides a starch which after gelatinization or pasting has a low-temperature stability greater than or equivalent to normal starch.

In the preferred embodiment, the starch is from a maize plant.

In other embodiments, the plant is a potato, wheat, rice, or barley plant.

In one embodiment, the starches of the present invention have an equivalent or lower differential scanning calorimetry retrogradation enthalpy than normal starch; or preferably a lower differential scanning calorimetry retrogradation enthalpy than normal starch after gelatinizing the starch by heating it to 140° C. at 10° C. per min, cooling the starch to 4° C., holding the starch for 7 days at 4° C., and then analyzing the retrogradation enthalpy observed after reheating the starch from 5° C. to 140° C. at 10° C. per min; or most preferably a differential scanning calorimetry retrogradation enthalpy between 3.5 J/g and 10 J/g after the starch as a 25% w/w suspension in water has been heated to 140° C. at 10° C. per min, cooled to 4° C., held for 7 days at 4° C., and then analyzed by reheating the starch from 5° C. to 140° C. at 10° C. per min.

In an additional embodiment, the starches of the present invention have a lower differential scanning calorimetry amylose-lipid complex enthalpy than normal starch; or preferably have an average amylose-lipid complex enthalpy less than 1.2 J/g and most preferably less than 1.1 J/g.

In a further embodiment, the starches of the present invention have greater paste stability than normal starch as detected by changes in the rheological properties of pastes prepared with the starches of the present invention between two storage time points.

The present invention provides a starch which has the ability to form gel structures unlike those of waxy or normal starch.

In the preferred embodiment, the starch is from a maize plant.

In other embodiments, the plant is a potato, wheat, rice, or barley plant.

In one embodiment, the gelatinized starches of the present invention have greater ability to form gels in a range of useful starch contents than do waxy starches, or between a range of starch contents between 2 and 80%, and preferably in a range of starch contents between 2% and 40%, and more preferably in a range of starch contents between 2% and 20%, and most preferably in a range of starch contents between 5 and 15%.

In another embodiment, the gelatinized starches of the present invention form easily deformable, highly resilient gel structures rather than firm, brittle gel structures formed by normal starch at the same concentration, or preferably form gels which do fracture as do normal starches when they contain 10% gelatinized starch solids, or more preferably have a resiliency greater than 50% when they contain 10% gelatinized starch solids, or most preferably form gels without a defined fracture point and a firmness below 30 g-s and a resilience of at least 50% when the starches are cooked as a suspension of 10% starch (dry weight %) using a Rapid Visco Analyzer and the instrument conditions specified in the Newport Scientific Method 1 (STD1) Version 5 method for the instrument and the resultant pastes are stored for 7 days at 4° C. with negligible loss in water.

The present invention provides a starch which has cooking viscosity stability higher than waxy starches.

In the preferred embodiment, the starch is from a maize plant.

In other embodiments, the plant is a potato, wheat, rice, or barley plant.

In one embodiment, the starch of the present invention develops viscosity at a slower rate than does waxy starch which is cooked under the same heating and shear conditions, and preferably the time between the pasting time and the peak time is greater than that duration for waxy starch, and more preferably the time between the pasting time and the peak time is greater than 90 seconds, and most preferably the time between the pasting time and the peak time is greater than 75 seconds when starches of the present invention are cooked as a suspension of 5% starch (dry weight %) in pH 6.5 phosphate buffer using a Rapid Visco Analyzer and the instrument conditions specified in the Newport Scientific Standard 1 Version 5 (December 1997) heating and stirring program.

In a further embodiment, the starch of the present invention develops viscosity at a slower rate than does waxy starch which is cooked under the same heating and shear conditions, and preferably the time between the pasting time and the peak time is greater than that duration for waxy starch, and more preferably the time between the pasting time and the peak time is greater than 90 seconds, and most preferably the time between the pasting time and the peak time is greater than 75 seconds when starches of the present invention are cooked as a suspension in pH 6.5 phosphate buffer using a Rapid Visco Analyzer 4 and using the Newport Scientific Standard 1 Version 5 (December 1997) heating and stirring program, when the concentration of the starch is such that a paste of waxy starch at the same concentration has a final viscosity of between 600 and 850 centipoise.

In another embodiment, the starch of the present invention reaches a peak viscosity at a time later than does waxy starch, preferably the peak time is greater than 4 min, and most preferably the peak time is greater than 5 min when starches of the present invention are cooked as a suspension of 5% starch (dry weight %) in pH 6.5 phosphate buffer using a Rapid Visco Analyzer 4 and the instrument conditions specified in the Newport Scientific Standard 1 Version 5 (December 1997) heating and stirring program.

In an additional embodiment, the starch of the present invention reaches a peak viscosity at a time later than does waxy starch, preferably the peak time is greater than 4 min, and most preferably the peak time is greater than 5 min when starches of the present invention are cooked as a suspension of in pH 6.5 phosphate buffer using a Rapid Visco Analyzer 4 and the instrument conditions specified in the Newport Scientific Standard 1 Version 5 (December 1997) heating and stirring program when the concentration of the starch is such that a paste of waxy starch at the same concentration has a final viscosity of between 600 and 850 centipoise.

In another embodiment, the starch of the present invention reaches a peak viscosity at a time later than does waxy starch, most preferably the peak time is greater than 4 min when starches of the present invention are cooked as a suspension of 5% starch (dry weight %) in pH 6.5 phosphate buffer using a Rapid Visco Analyzer and the instrument conditions specified in the Newport Scientific ST-01 Revision 3 heating and stirring program for the instrument.

In yet another embodiment, the starch of the present invention loses viscosity at a slower rate than does waxy starch after reaching a peak viscosity, preferably the breakdown viscosity to peak viscosity (B/P) ratio is less than 35% and most preferably less than 30% when starches of the present invention are cooked as a suspension of 5% starch (dry weight %) in pH 6.5 phosphate buffer using a rapid Visco Analyzer and the instrument conditions specified in the Newport Scientific Standard 1 Version 5 (December 1997) heating and stirring program.

In yet another embodiment, the starch of the present invention loses viscosity at a slower rate than does waxy starch after reaching a peak viscosity, preferably the breakdown viscosity to peak viscosity (B/P) ratio is less than 35% and most preferably less than 30% when starches of the present invention are cooked as a suspension of in pH 6.5 phosphate buffer using a Rapid Visco Analyzer 4 and the instrument conditions specified in the Newport Scientific Standard 1 Version 5 (December 1997) heating and stirring program when the concentration of the starch is such that a paste of waxy starch at the same concentration has a final viscosity of between 600 and 850 centipoise.

In an additional embodiment, the starch of the present invention develops a paste with a higher final viscosity than a paste of waxy starch, preferably the final viscosity is greater than 850 cp and more preferably is greater than 900 cp when starches of the present invention is cooked as a suspension of 5% starch (dry weight %) in pH 6.5 phosphate buffer using a Rapid Visco Analyzer 4 and the instrument conditions specified in the Newport Scientific Standard 1 Version 5 (December 1997) heating and stirring program, and preferably the final viscosity is greater than 650 cp and more preferably is greater than 700 cp when starches of the present invention are cooked as a suspension of 5% starch (dry weight %) in pH 6.5 phosphate buffer using a Rapid Visco Analyzer 4 and the instrument conditions specified in the Newport Scientific ST-01 Revision 3 heating and stirring program for the instrument.

The present invention includes the making of sols and pastes of the starch of the present invention in the presence of dissolved solutes.

The present invention includes the making of gels of the starch of the present invention.

The present invention includes making sols or gels of the starch of the present invention for use in foodstuffs such as pie fillings, puddings, soups, sauces, gravies, coatings, candies and/or confectionary products, and/or yoghurts and other dairy products.

The present invention includes adding the starch of the present invention as an ingredient to foodstuffs such as pie fillings, puddings, soups, sauces, gravies, coatings, candies and/or confectionary products, and/or yoghurts and other dairy products.

The present invention provides a starch which has an amylose content between waxy starch and normal starch.

In the preferred embodiment, the starch is from a maize plant.

In the preferred embodiment, the starches of the present invention have amylose contents between 1.5% and 15% on a weight basis.

In another embodiment, the starches of the present invention have amylose contents between 2% and 15% on a weight basis.

In an additional embodiment, the starches of the present invention have amylose contents between 2.5% and 15% on a weight basis.

In an additional embodiment, the starches of the present invention have amylose contents between 3.5% and 15% on a weight basis.

In a further embodiment, the starches of the present invention have amylose contents between 1.5% and 10% on a weight basis.

In an additional embodiment, the starches of the present invention have amylose contents between 2% and 10% on a weight basis.

In another embodiment, the starches of the present invention have amylose contents between 2.5% and 10% on a weight basis.

In a further embodiment, the starches of the present invention have amylose contents between 3.5% and 10% on a weight basis In another embodiment, the starches of the present invention have amylose contents between 1.5% and 8% on a weight basis.

In a further embodiment, the starches of the present invention have amylose contents between 2% and 8% on a weight basis.

In an additional embodiment, the starches of the present invention have amylose contents between 2.5% and 8% on a weight basis.

In an additional embodiment, the starches of the present invention have amylose contents between 3.5% and 8% on a weight basis.

In a further embodiment, the starch is a potato starch with an amylose content between 3.5 and 12.5 and more preferably between 4% and 12.5%.

In another embodiment, the starch is a wheat starch with an amylose content between 1.5% and 15% and more preferably between 2.5% and 15% and most preferably between 3% and 10%.

In an additional embodiment, the starch is a rice starch with an amylose content between 1.5% and 15% and more preferably between 3% and 15% and most preferably between 3% and 6%.

In another embodiment, the starch is a barley starch with an amylose content between 1.5% and 15% and more preferably between 7% and 15%.

The present invention provides a method of forming a starch of the present invention in the starch storing organs of wheat, barley, rice, sorghum, oats, rye or maize.

In the preferred embodiment, the starch bearing plant is a maize plant.

In other embodiments, the plant is a potato, wheat, rice, or barley plant.

The present invention further provides a starch of the present invention extracted from the starch producing organs of a plant.

In the preferred embodiment, the starch bearing plant is a maize plant.

In other embodiments, the plant is a potato, wheat, rice, or barley plant.

In one embodiment, the starch storing organs are formed on a plant grown from a propagative structure after selection following mutageness.

The present invention provides a method of producing a starch of the present invention in the starch storage organs of a plant comprising the steps of: applying EMS to pollen of plants, forming treated pollen; self-pollinating plants with the treated pollen; selecting plant propagative structures with at least one mutation which appear to produce starch storage organs containing starch of the present invention; planting said plant propagative structures to produce additional plant propagative structures; selecting propagative structures from plants which appear to produce starch storage organs containing starch of the present invention; repeating this cycle of planting and selection to increase propagative structure quantities; optionally, said plants may be backcrossed to ensure purity; extracting starch wherein said starch is a starch of the present invention. This method can include the step of increasing said plant propagative structures.

The present invention provides a method of producing a starch of the present invention in the starch storage organs of a plant comprising the steps of: mutagenizing propagative structures of plants; growing plants from said propagative structures; selecting plant propagative structures with at least one mutation which appear to produce starch storage organs containing starch of the present invention; planting said plant propagative structures to produce additional plant propagative structures; selecting propagative structures which appear to produce starch storage organs containing starch of the present invention; repeating this cycle of planting and selection to increase propagative structure quantities; optionally, said plants may be backcrossed to ensure purity; extracting starch wherein said starch is a starch of the present invention. This method can include the step of increasing said plant propagative structures.

The present invention provides a method of producing a starch of the present invention in the starch storage organs of a plant comprising the steps of: mutagenizing cells of plants; regenerating plants from said cells; selecting plant propagative structures with at least one mutation which appear to produce starch storage organs containing starch of the present invention; planting said plant propagative structures to produce additional plant propagative structures; selecting propagative structures which appear to produce starch storage organs containing starch of the present invention; repeating this cycle of planting and selection to increase propagative structure quantities; optionally, said plants may be backcrossed to ensure purity; extracting starch wherein said starch is a starch of the present invention. This method can include the step of increasing said plant propagative structures.

Additional method steps can be steps of planting said propagative structures to produce plants with the intent to form more propagative structures which will produce starch storing organs containing starch of the present invention on starch bearing plants, or the step of harvesting the propagative structures, or the step of crossing the starch bearing plant with a second plant producing starch of the present invention wherein hybrid propagative structures are formed on at least one of the plants and then the additional step of harvesting the propagative structures.

The present invention's scope also encompasses the step of harvesting the starch storing organs for the extraction of starch.

The present invention can also be described as a method of producing plants which produce starch storing organs which contain starch of the present invention including the steps of inducing at least one mutation in the waxy locus of plants; selecting propagative structures from the plant having at least one mutation; growing plants from the propagative structures; forming propagative structures on the plants; and extracting the starch of the present invention from the starch storing organs.

More particularly the mutation is located in the starch-affecting locus the waxy locus in the plant's genome, and even more particularly, the mutation is a point mutation.

The present invention also includes a product which is a starch of the present invention extracted from the starch producing organs of a plant comprising starch produced by the plant having at least one mutation originally induced into the genetic ancestry of the plant by EMS and at least one of the mutations wherein the starch storing organs of the plant produce a starch of the present invention.

In another embodiment, the starch storing organs are formed by selection following plant transformation designed to reduce the activity of the GBSS enzyme in a normal plant.

The present invention can also be described as a method of producing plants which produce a starch of the present invention including the steps of: inducing an antisense construct for a starch affecting locus of the seed bearing plants; selecting propagative structures from the plant having the antisense construct; growing plants from the propagative structures; forming starch storing organs on the plants; and extracting the starch of the present invention from the starch storing organs.

The present invention also provides the cDNA encoding a granule bound starch synthase which has the sequence SEQ ID NO:2.

In yet another embodiment, the starch storing organs are formed by selection following plant transformation designed to increase the activity of a GBSS-like enzyme in a waxy plant.

The present invention can also be described as a method of producing plants which produce a starch of the present invention including the steps of: inducing a sense construct for a starch affecting locus of the seed bearing plants; selecting propagative structures from the plant having the sense construct; growing plants from the propagative structures; forming starch storing organs on the plants; and extracting the starch of the present invention from the starch storing organs.

The present invention can also be described as a method of producing plants which produce a starch of the present invention including the steps of: inducing an expression construct for a starch affecting locus of starch storing plants having a mutation in amylose formation; selecting propagative structures from the plant having the expression construct; growing plants from the propagative structures; forming starch storing organs on the plants; and extracting starch of the present invention from the starch storing organs.

The invention additionally provides transformed plants containing one or more copies of the said cDNA in the sense orientation.

The present invention also provides the granule bound starch synthase which has the amino acid sequence SEQ ID NO:4.

In further embodiments of this invention the starch bearing plant may be any cereal plant (such as wheat, barley, sorghum, rice, oats, rye etc) or any starch forming plant.

In the preferred embodiment, the plant is a maize plant.

In other embodiments, the plant is a potato, wheat, rice, or barley plant.

Broadly the present invention provides for a the starch storing organs of a plant which contain starch which has unique cooking and functional properties and starch which has an amylose content below 15% (such starches are herein referred to as an waxy-E starch).

The present invention provides for the use of a potato starch with an amylose content between 3.5% and 12.5% and more preferably between 4% and 12.5% to increase the elasticity of a product.

The present invention provides for the use of a wheat starch with an amylose content between 1.5% and 15% and more preferably between 2.5% and 15% to increase the elasticity of a product.

The present invention provides for the use of a rice starch with an amylose content between 1.5% and 15% and more preferably between 3% and 15%, and most preferably between 3% and 6% to increase the elasticity of a product.

The present invention provides for the use of a barley starch with an amylose content between 1.5% and 15% and more preferably between 7% and 15% to increase the elasticity of a product.

The present invention provides for the use of a corn starch with an amylose content between 1.5% and 15% and more preferably between 2.5% and 15% to increase the elasticity of a product.

Three seed sets EX385wx-E1, EX56wx-E1, and EX12wx-E2 have been deposited as EX385wxa, EX56wxa and EX12wxa, respectively, on Sep. 27, 2001, with the American Type Culture Collection, 10801 University Blvd., Manassas, Va. 20110-2209, under conditions of the Budapest Treaty, and assigned Accession Nos. PTA-3730, PTA-3731 and PTA-3732, respectively.

The present invention provides, therefore, a plant starch containing a reduced amylose content and having an EM greater than, alternatively at least twice that of, the EM of a waxy starch of the same plant species and an EM less than the EM of a starch of a wild-type plant of the same species, wherein the AP ratio of the plant starch of the invention is within 0.5 of the starch of the wild-type plant of the same species. In one embodiment, the plant starch of the present invention has an EM of at least 10 Pascals and the AP ratio of the plant starch of the present invention is within 0.5 of a starch of a wild-type plant of the same species.

In one embodiment, the starch of the present invention is as described above and the EM is measured after the starch has been cooked as a suspension of starch using a Rapid Visco Analyzer 4 instrument, and instrument conditions specified in the Newport Scientific Method 1 (STD1) Version 5 heating and stirring profile, and stored for 24 hours at 25° C.

In a further embodiment, the starch of the present invention has a phase angle below the yield strain of less than that of a waxy plant starch of the same plant species.

The starch of the present invention may be further characterized as having more of a gel character below the yield strain than a waxy plant starch of the same plant species and less of a gel character than a plant starch of a wild-type plant of the same species.

The starch of the present invention may be also characterized as having an increase in G' less than 2 fold when subjected to a strain of below the yield strain, as the oscillatory testing frequency is increased from 0.1 to 100 radians per second.

Moreover, the plant starch of the present invention may have a firmness below 30 g-s and above 1 g-s after being cooked as a suspension of 10% starch (dry weight %) according to the RVA Standard Method and then stored for 7 days at 4° C., and the AP ratio of the plant starch of the invention is within 0.5 of the AP ratio of starch of a wild-type plant of the same species.

The plant starch of the present invention has a resilience of at least 50% after having been cooked as a suspension of 10% starch (dry weight %) according to the RVA Standard Method and then stored for 7 days at 4° C. after cooking, and the AP ratio of the plant starch is within 0.5 of the AP ratio of starch of a wild-type plant of the same species.

The plant starch of the present invention demonstrates, according to the RVA Standard Method, a time of greater than 75 seconds between pasting time and peak time after the starch has been cooked at a concentration such that the final viscosity of a waxy starch of the same species cooked at said concentration is between 600 and 850 centipoise, the AP ratio of the starch being within 0.5 of the AP ratio of starch of a wild-type plant of the same species.

The plant starch of the present invention contains a reduced amylose content and demonstrates a ratio of breakdown viscosity to peak viscosity of less than 35%, as measured by the RVA Standard Method, after the starch has been cooked at a concentration whereby the final viscosity of a waxy starch of the same species cooked at said concentration is between 600 and 850 centipoise, the plant starch having an AP ratio of within 0.5 of the AP ratio of starch of a wild-type plant of the same species.

The starch decribed herein may be obtained from a plant containing at least one mutation in the waxy locus of said plant.

The plant starch of the present invention may be obtained from a plant selected from a corn plant, a potato plant, a wheat plant, a rice plant or a barley plant.

The present invention provides a plant which produces the starch of the present invention.

The plant of the present invention may have reduced GBSS activity as a result of at least one of a genetic mutation and a genetic transformation.

The present invention provides a method of producing a starch of the present invention by a method which includes the steps of applying EMS to pollen of plants, forming treated pollen, pollinating plants with the treated pollen or propagation structures, harvesting M1 propagative structures produced from the pollinated plants, planting the M1 propagative structures, harvesting M2 propagative structures from the planted M1 propagative structures, and selecting and/or screening starch from the M2 propagative structures.

The present invention provides a method of producing a starch of the present invention which includes the steps of inducing a mutation in a starch affecting locus of starch storage organ bearing plants, selecting propagative structures from the mutant plants, growing plants from the propagative structures, and selecting and/or screening starch storing organs.

The present invention provides starch selected and/or screened according to the methods, such as those described above, disclosed herein.

In one embodiment, the invention provides a method of producing a plant starch of the invention which includes incorporating a mutation into the genetic ancestry of said plant, wherein the mutation results in the production of the starch.

The plants of the present invention may be a corn plant, a potato plant, a wheat plant, a rice plant or a barley plant. The present invention further provides propagative and non-propagative parts of the disclosed plants.

The present invention provides an isolated nucleic acid molecule encoding a polypeptide having the starch synthase activity of a polypeptide having the amino acid sequence of SEQ ID NO:4. A nucleic acid sequence encoding the amino acid sequence of or including SEQ ID NO:4 is provided. An isolated nucleic acid molecule having the nucleic acid sequence of SEQ ID NO:2 is further described herein and provided by the present invention.

The present invention provides a sol or paste containing the starch of the present invention, as well as a foodstuff containing the same. The present invention further provides a gel of the starch of the present invention, as well as a foodstuff containing the same. A foodstuff containing the starch of the present invention is also provided herein. Methods of making the foodstuffs described herein are also described herein, such as including the steps of admixing a starch, gel, sol, past and/or sol of the present invention with edible ingredients. Methods of making starch preparations more elastic are also provided herein which include admixing the presently described starch, gel, sol, past and/or sol of the present invention with edible and/or starch-containing ingredients and/or components requiring more elastic properties.

Still further objects and advantages will become apparent from a consideration of the ensuing description, accompanying drawings, and examples.

Starch is the granular or powdery complex carbohydrate that is the chief storage form of carbohydrate in plants.

Amylose content is the quantity of amylose in a starch on a dry weight basis determined by comparison to standards.

Normal starch is the starch extracted from the seed of a plant with the expected genes regulating the starch biosynthetic pathway (wild types) that consistently averages an amylose content of 18% to 28%. Such normal starch stains homogeneously blue or purple upon iodine staining.

Waxy starch is the starch extracted from the seed of a plant that consistently stains homogeneously red, brown or red-brown upon iodine staining.

Unmodified starch is starch extracted from seed which has not been further processed with chemicals or enzymes or has not been processed through a heating, cooling, pressure or any other physical regime with the intent to alter the chemical, structural or rheological or textural properties of the starch from its original state.

Modified starch is any starch which after extraction from seed has been processed with chemicals or enzymes or has been processed through a heating, cooling, pressure or any other physical regime with the intent to alter the structural or rheological or textural properties of the starch from its original state after extraction.

Mutant is a description of any biochemical entity (e.g. DNA, RNA, protein, enzyme) which has deviated either in structure or in function or in expression from normal as a result of a change(s) in DNA sequence.

Mutation an alteration in the DNA which results in a mutant biochemical entity.

Mutagenized is any plant tissue treated with a mutagen to induce a mutation in the plant DNA.

Waxy Mutant is any plant that produces waxy starch. Such starch stains homogeneously red, or brown or brown-red upon iodine staining.

Propagative structure For some plants, this may be the fertilized ripened ovule of a flowering plant containing an embryo and capable normally of germination to produce a new plant. For other plants, this may be a short fleshy usually underground stem bearing minute scale leaves each of which bears a bud in its axil and is potentially able to produce a new plant. Additionally, this may be the often underground part of a seed plant body that originates usually from the hypocotyl, functions as an organ of absorption, aeration, and food storage or as a means of anchorage and support, and differs from a stem especially in lacking nodes, buds, and leaves. Further, this may be any cutting or tissue which may be regenerated into a new plant. A propagative structure may be a starch storing organ or starch storage organ of a plant.

Starch storing organ or starch storage organ is a plant structure which stores starch. This may be a propagative structure of a plant.

Sol or Paste is a fluid colloidal system in which the continuous phase is a liquid and which is utilized primarily for its viscosity or other rheological attributes.

Pasting is the process or act of producing a paste or sol.

Gel is a semirigid or rigid colloidal system.

Centipoise or cp is a unit of measure of viscosity equivalent to $1 \times 10^{-3}$ pascal seconds (Pa s)

Peak viscosity is the maximum viscosity a starch paste reaches during a process.

Hot Paste viscosity or HP Viscosity is the viscosity of a starch paste after 2.5 minutes at 95° C.

Breakdown is the decrease in the viscosity of a starch paste from its peak viscosity to some minimum viscosity during a process. The minimum viscosity is observed after the peak viscosity in time.

Final Viscosity is the viscosity of a starch paste at the end of a process.

Setback is the increase in viscosity of a starch paste from some minimum viscosity attained during a process to the final viscosity. The minimum viscosity is observed after the peak viscosity in time.

Peak time is the time at which the peak viscosity is attained during a process.

Pasting temperature is the temperature at which an initial increase in viscosity is detected during a process.

Pasting time is the time at which an initial increase in viscosity is detected during a process.

GBSS (granule bound starch synthase) Enzyme Activity or GBSS activity is the activity of 60 kDa starch synthase enzyme visualized on renaturing PAGE gels and distinguished from other starch synthase enzyme activities in that it stains as a dense blue or dark band upon $KI/I_2$ staining due to the transfer of glucosyl units from ADP-glucose supplied in the reaction mixture to either glycogen or amylopectin embedded in the polyacrylamide gel matrix via formation of (1–4) linkages.

BRIEF DESCRIPTION OF THE DRAWINGS

FIG. 11.(a) Detection of the GBSS protein associated with immature starch granules (14 to 23 days) using western blotting. The identity of the starch and the maturity of the seed for each lane is indicated. (b) Detection of GBSS protein associated with mature starch granules using western blotting. The identity of the starch and the maturity of the seed for each lane is indicated.

FIG. 13.(a) is a schematic showing the design and restriction enzyme sites of plant transformation vectors used to alter nucleic acid expression levels in plants. (b) is a schematic showing the design and restriction enzyme sites of plant transformation used to introduce an nucleic acid sequence into plants.

Figure 1:
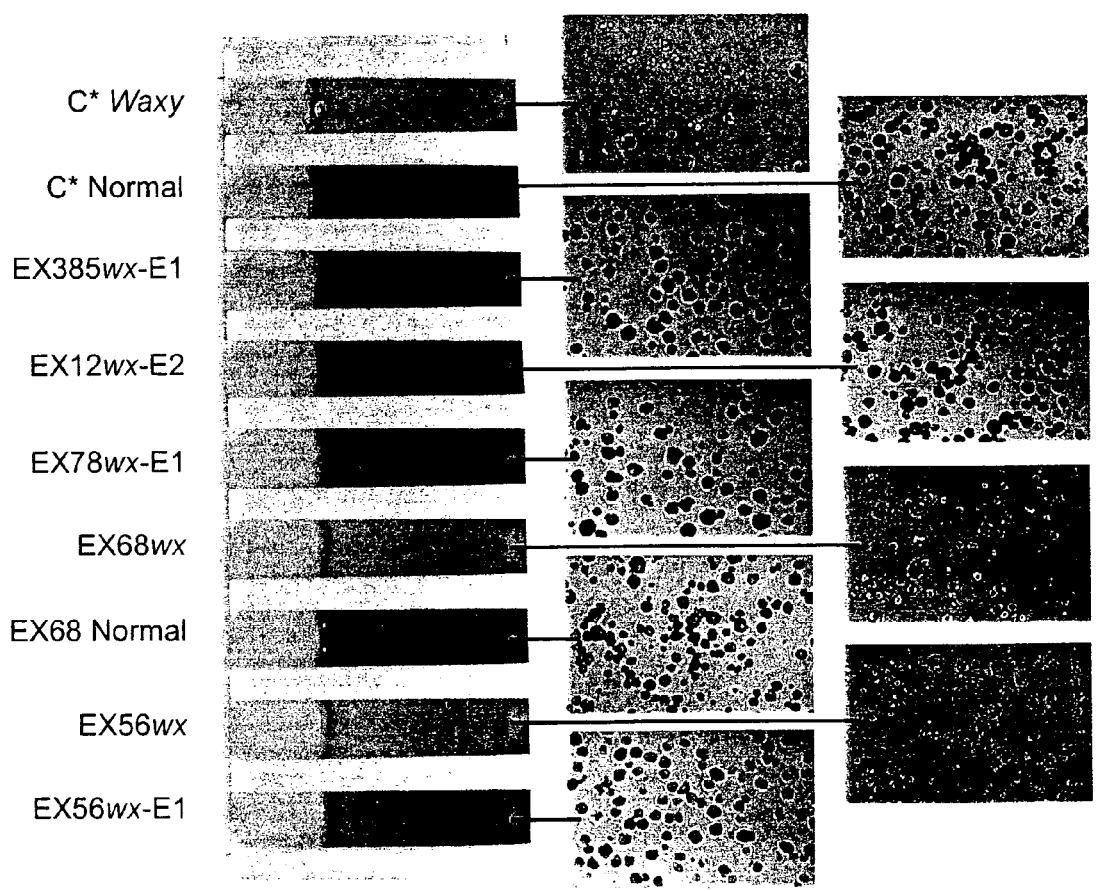
FIG. 1. Iodine staining properties of starch granules. Bulk staining properties are to the left and the staining characteristics of a representative field of starch granules are to the right. Starch names are indicated at the far left of the drawing. All waxy starches are identified by either the "wx" designation (lab-isolated) or by the "Waxy" designation (commercially-isolated). All waxy-E starches are designated by the "wx-E1" or "wx-E2" designation.

This invention describes the production of, identification of, and examination of the starch extracted from plants such as maize plants and/or other plants which produce waxy-E starch. The waxy-E starch has several characteristics which are in combination an improvement over waxy starches:

1) The waxy-E starch produces a high peak viscosity and retains more viscosity at high temperatures under shear than does waxy starch.

2) The waxy-E starch has unique paste and gel rheological characteristics.

3) The waxy-E starch has useful low-temperature paste and gel stability.

These properties are a result of the unique molecular composition of the waxy-E starch, primarily that the waxy-E starch has an amylose content below 10% distributed throughout the bulk of the starch granules. The amylose produced is a result of the reduced but detectable activity of the GBSS enzyme in the starch storing organ compared to the relatively high GBSS activity of normal starch storing organs and the undetectable GBSS activity from waxy starch storing organs.

Additionally, the invention also encompasses a method of producing a waxy-E starch in plants through mutableness or using biotechnology.

Mutant Plant Generation and Screening

Waxy starch may be extracted from a breeding population of corn, wheat, rice, potato or other starchy crop having a recessive wx gene. The population contains the wx gene and selections of modified germplasm which are homozygous for the wx gene. The present invention allows the production of plants capable of producing waxy-E starch in plant inbreds or varieties. The present invention includes the discovery that these plants can be made by pollen mutableness. This process results in the creation of point mutants within the plant genome. The waxy-E mutants produced herein are allelic mutants. The locus is allelic with the waxy locus. The waxy-E locus when mutagenized results in a distinctive phenotype: a starch which has unique cooking and rheological properties and a low amylose content and a starch storing organ which contains a partially active GBSS enzyme. The waxy gene of wild types encodes granule bound starch synthase (GBSS) enzyme, and waxy-E mutants in common with waxy mutants have a point mutation in the waxy locus.

The improved crops of the present invention having the above described characteristics may be produced by using the following pollen mutableness procedure on elite maize inbreds or on any variety of plant species. Additionally other technical approaches that can be envisioned which lead to the same waxy-E phenotype, including mutableness, biotechnology, and breeding.

The method of producing these elite, agronomically sound, high yielding, waxy-E mutants is a known method called mutableness. The process is outlined in the Neuffer paper Maize Genetic Newsletter 45:146. It should be noted that ethylmethane sulfonate (EMS) is a chemical which induces mutations (a mutagen). Like all mutation processes the act of mutation can adversely effect the agronomic traits especially yields of the plant. However, the starting germplasm is superior to that in which the low amylose mutant is usually formed. Thus the overall agronomic traits of the plant of the present invention are more easily preserved and selected for than the industrial approach of recurrent selection or backcrossing. Mutations were induced in the inbred line by treating pollen with EMS in paraffin oil according to the procedure described by Neuffer (1974, Maize Genetic Newsletter 45:146). This treatment was performed on a number of inbreds from the various plant genotypes of cereal. This example will focus on the development of maize waxy-E mutants by this process. This mutableness process has been used to make a number of cereal mutants, including waxy and amylose-extender. The process does guarantee the generation of and simple identifiation of an waxy-E plant. Instead, tens of thousands of seeds from hundreds of plant lines required screening to find putative waxy mutants. Within this set of putative waxy mutants, a second intensive screening was required to find waxy-E mutants. This second screening included increasing the amount of seed, isolating the starch from the seed, and further examining the cooking properties of the resultant starch, examining the amylose content of the resultant starch, and examining the GBSS enzyme activity of seed. Only after this second intensive screening could a few mutants of the putative waxy mutants be classified as producing waxy-E starch. The waxy-E starches of the present invention cannot be produced in maize through heterozygous combinations of normal (Wx) and mutant (waxy) genes by cross pollinating normal and waxy plants. Additionally, the properties of the low amylose starch cannot be reproduced by mixing starch from normal plants and waxy plants, resulting in mixtures with an amylose content less than 15%. Recurrent selection and backcrossing, the most common technique for producing waxy lines from pre-existing waxy lines, would not be successful in producing waxy-E starches of the present invention from existing waxy lines. Additionally, recurrent selection and backcrossing require a number of generations to develop the desired plants whereas the waxy-E starches of the present invention are generated within a single generation through EMS mutableness.

The general steps of the one process to produce plant lines producing waxy-E starch of the present invention include treating inbred pollen (in this case maize) with EMS. Pollen from an inbred line is placed in EMS in oil. A paint brush is used to apply the pollen on to the silks of a receptive corn ear. This forms the Mutant-1(M1) seed. Such seeds are harvested, grown, and self-pollinated to produce the Mutant-2 (M2) kernels. The resulting M2 kernels are examined visually for the waxy phenotype. This is classically a full, opaque endosperm compared to normal endosperm.

The next step is an increase of the seed by self pollination. Increases of the seed may occur over one or multiple generations to obtain quantities of seed sufficient for analysis, starch isolation, or further breeding.

When sufficient seed is available the next step is to cross the putative mutant with a waxy seed phenotype to a waxy mutant inbred to provide a crude verification that in fact the kernel is either a waxy or an waxy-E mutant. A standard waxy mutant or waxy-E or other low amylose mutant inbred is selected. The mutant plant is grown and crossed to the standard and the hybrid seed is once again visually examined for phenotype. If the mutant is the same as the standard then the kernels on the hybrid should be consistent with one another for the phenotype. This test is used because the mutant gene is recessive.

A sample from the increased seed source is further screened for waxy-E starch production. This is done by rehydrating one or more kernels in water (50° C. for 1 day) and then crushing the seed to release the starch. A sample of crushed endosperm is added to a microscope slide, a drop of water added to the sample, and then a cover slide is placed over the wet sample. To one edge of the microscope slide, a drop of diluted stock iodine solution (2 g/L iodine, 20 g/L potassium iodide diluted 10×with water) is added and drawn into the endosperm sample by capillary action. The leading edge of the iodine solution under the cover slide is then examined under the microscope. The observation of blue staining granules is a positive indication that the mutableness resulted in the creation of an waxy-E event. Starch from seed containing putative waxy-E starch along with waxy phenotype seed is isolated on a larger scale for additional examination and characterization.

Transgenic Plant Generation and Screening

There are reports of vectors for engineering modification in the starch pathway by use of a number of starch synthesis genes in various plants. For example, the U.S. Pat. No. 5,349,123 described a vector containing DNA to form glycogen biosynthetic enzymes within plant cells to introduce changes in the potato starch. The present invention provides a starch storing organ with reduced GBSS activity and a starch with a unique rheology and a low amylose content in plants made possible by alterations at the waxy-E locus either by shuffling, mutableness or biotechnology and/or breeding methods.

In the present invention, the waxy-E locus will be generated using (a) standard recombinant methods, (b) synthetic techniques, or (c) combination of both. The isolated nucleic acid may also be produced by "Shuffling" or synthetic arrangement of part or parts of one or more allelic forms of the nucleic acid sequence of interest. The waxy locus will be modified either through point mutations, antisense technology, and/or gene silencing via knockdowns, site directed mutableness, $RNA_i$, or any other methods known in the art to generate the starch of the present invention. These changes will reduce/silence the level of expression of the Waxy gene and/or change its functional properties and thereby will either reduce the corresponding GBSS protein levels, and/or decrease the activity of GBSS enzyme.

In some embodiments, the desired and modified polynucleotide of Waxy locus of the present invention with multiple functionalities will be cloned, amplified or constructed from any starch producing plant. The isolated nucleic acid compositions of this invention, such as RNA, DNA, and genomic DNA can be obtained from plants or other biological sources using any number of cloning techniques known in the art. Functional fragments from different species included in the invention can be obtained using primers (12 to 200 bases) that selectively hybridize under stringent conditions. Functional fragments can be identified using a variety of techniques such as restriction analysis, southern analysis, primer extension analysis and DNA sequence analysis. Variants included in the invention may contain individual substitutions, deletions or additions to the nucleic acid or polypeptide sequence. Such changes will alter, add or delete a single amino acid or a small percentage of amino acids in the encoded sequence.

Preferred nucleic acid molecules of this invention comprise DNA encoding the waxy-E locus with a modification introduced in the functionality of the GBSS enzyme via any or above said methods from any organism and comprise nucleic acid sequences set forth hereof (SEQ ID NO:2).

A polynucleotide of the present invention can be attached to a vector, adapter, promoter, transit peptide or linker for cloning and or for its expression. Preferred plasmids of this invention are adapted for use with specific hosts. A polynucleotide of the present invention can be expressed in sense or antisense orientation (see attached examples for maize, FIG. 13). Plasmids comprising a promoter, a plastid-targeting sequence, a nucleic acid sequence encoding the modified Waxy locus with a modified functionality of GBSS enzyme and a terminator sequence are provided herein (Such plasmids are suitable for insertion of DNA sequences encoding the eGBSS enzyme with modified functionality to express in selected hosts and produce EM (elastic modulus) starch. The invention includes plasmids comprising promoters adapted for both prokaryotic and eukaryotic hosts. The said promoters may also be specifically adapted for expression in monocots or in dicots.

Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art.

Figure 14:
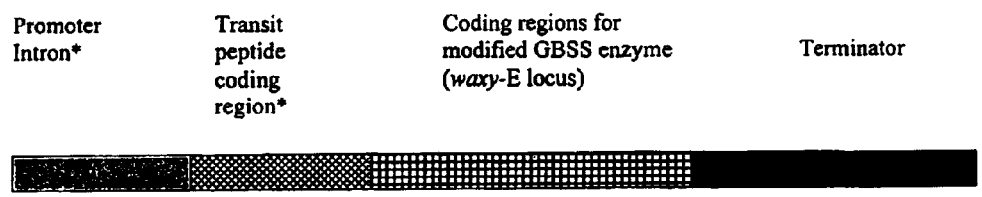
FIG. 14 shows a diagram of a DNA construct for expressing the waxy-E locus within the host.

The DNA Construct for expressing the waxy-E locus within the host is broadly shown in FIG. 14.

As is known in the art, a promoter is a region of DNA controlling transcription. Different types of promoters will be selected for different hosts. Lac and T7 promoters work well in prokaryotes, the 35S CaMV promoter works well in dicots. And the polyubiquitin promoter works well in many monocots. Other suitable promoters include maize 10 kDa Zein promoter, GBSS promoter, ST1 promoter, TR1 promoter, napin promoter etc. Any number of different promoters are known to the art can be used within the scope of this invention. It can be constitutive, inducible, tissue specific and may be homologous or heterologous to the said plant.

Also, as is known to the art, an intron is a nucleotide sequence in a nucleic acid sequence that does not code for the gene product. One component of an intron that often increases expression in monocots is the Adh1 intron. This component of the construct is optional.

The transit peptide-coding region is a nucleotide sequence that encodes for the translocation of the protein into organelles such as plastids and mitochondria. A transit peptide that is recognized and compatible with the host in which the transit peptide is employed is preferred. In this invention the plastid of choice is the amyloplast. An example is the Ferredoxin transit peptide.

It is preferred that the hybrid polypeptide be located within the amyloplast in cells such as plant cells that synthesize and store starch in amyloplasts. If the host is a bacterial or other cell that does not contain an amyloplast, there need not be a transit peptide-coding region.

A terminator is a DNA sequence that terminates the transcription.

The polypeptides generated by the above method may also include post-translational modifications known to the art such as glycosylation, acylation, and other modifications not interfering with the desired activity of the polypeptide.

A variety of methods are known in the art to transform crops or other host cells and any method that provides for efficient transformation/transfection may be employed. A DNA construct of the present invention may be introduced directly into the genomic DNA of the plant cell using techniques such as electroporation, particle bombardment, silicon fiber delivery, or microinjection of plant cell protoplasts or embryogenic callus. Also, the DNA constructs may be combined with suitable T-DNA flanking regions and introduced into a conventional *Agrobacterium tumefaciens* host vector.

The present invention provides methods for increasing or decreasing the concentration or composition of Waxy locus that encodes for GBSS enzyme in a plant or part thereof. The method comprises transformation of a wx plant cell with an expression cassette comprising waxy-E polynucleotide to obtain a transformed plant cell later on grown to a plant under favorable growth conditions and the plant expresses the modified GBSS protein for considerable period of time and it results in production of a starch of the present invention. The plant cell or the plant part comprising the isolated nucleic acid is selected by means known to the skilled art, and include southern blot, DNA sequencing, or PCR analysis using primers specific to the promoter and to the nucleic acid and detecting amplicons produced therefrom. Proteins of the present invention are derived from native GBSS by addition or substitution of one or more amino acids at one or more sites either by genetic polymorphism or synthetic manipulations known in the art. The protein of the present invention can be expressed in a recombinant engineered cell such as bacteria, yeast, insect, and plant cells. The proteins of the invention may be purified using the methods known in the art. Detection of the proteins that are expressed will be achieved by the methods known in the art and include, for example radioactive assays, radioimmunoassay, different electrophoresis techniques, western blotting technique or immunoprecipitation, enzyme-linked immunosorbent assays (ELISAs), immunofluorescent assays, high performance liquid chromatography (HPLC), thin layer chromatography (TLC), and etc.

Starch Examination

Starch Isolation

Starch may be isolated on larger or smaller scales as needed; such procedures are well-described in the literature (e.g. Singh et al, 1997, Cereal Chemistry 74: 40–48). All waxy-E starches are easily isolated in quantity using the above method and the yield losses typically observed with other single mutants (e.g. amylose-extender, sugary-2, dull) and most especially double mutants are not observed. Additionally, by conducting the initial rehydration of the seed at 50° C., the isolation procedure is able to provide evidence that the waxy-E starch may be isolated from waxy-E seed using existing processing technologies, which often involve an initial rehydration of the seed between 50° C. and 55° C.

Starch Amylose Content Analysis

The amylose content of the putative waxy-E starch is determined. The test is based on the fact that two polysaccharide components existing in starch form helical polyiodide complexes with different spectrophotometric properties: the linear amylose complexes iodine to form a deep blue complex and the branched, short chain amylopectin weakly complexes iodine and gives a red coloration (Bailey and Whelan, 1961, The Journal of Biological Chemistry, 236:969–973; Banks et al, 1971, Carbohydrate Research 17:25–33). Thus, waxy starches are differentiated from other starches by their inability to form this deep blue complex when examined in the presence of a commonly used solution of iodine and potassium iodide. The waxy-E starches contain amylose and thus form this blue complex.

More rigorous determination of the amylose content of waxy-E starches, normal starches, and/or waxy starches may be done through calculation by comparing the spectrophotometric absorbance of an iodine stained sample to standards of iodine stained amylose and/or amylopectin and/or waxy starch. The amylose content of the starch is determined from an equation derived from the standard curves for amylose and waxy maize starch (Absorbance at 635 nm vs. carbohydrate concentration) and from the total carbohydrate of each unknown solution, as determined using the method of Dubois et al (1956, Analytical Chemistry 28: 350–356). A similar standardization was utilized by Knutson and Grove (1994, Cereal Chemistry 71: 469–471) to correct the amylose content of the starch based on the total carbohydrate content of the solution measured. Thus, a weight basis amylose content is obtained.

The waxy-E starches of the present invention have an amylose content ranging from 1.5% to between 8% and 12%, depending on whether or not the absorbance of the sample is corrected for the small absorbance of the amylopectin of the sample.

Starch Physical Property Analysis

The waxy-E starches of the present invention are confirmed by testing them against waxy and/or normal and/or other starches for their physical properties using several instrumental techniques. These instruments and techniques, in addition to others, can be used to quantitatively assess the differences one starch has in relation to another. Hence, some value of a starch relative to others in food or industrial applications may be assessed and determined. These techniques apply to both unmodified starch or modified starch, with the starch modified using practices and techniques familiar to those proficient in the art (Whistler, R. L. and BeMiller, J. N. 1997. Carbohydrate chemistry for Food Scientists, Eagan Press, St. Paul, pp. 137–150; Whistler and Daniel, 1985, Carbohydrates, in Food Chemistry, O. R. Fennema, ed., Marcel Dekker, Inc., New York, pp. 118–121; Zheng, G. H. et al, 1999, Cereal Chemistry 76:182–188; Reddy and Seib, 2000, Journal of Cereal Science 31:25–39) to improve or change the physical behavior or chemical structure of the starch.

All of these instrumental techniques require knowledge of the dry solids content of the starch. The solids content is calculated by determining the percentage moisture of the starch and then subtracting this value from 100. The moisture content of the starch is assessed using the one-stage moisture determination method of Standard Method 44-15A of the American Association of Cereal Chemists (2000, Method 44-15A, Moisture-Air Oven Methods, Approved Methods of the American Association of Cereal Chemists, Tenth Ed., American Association of Cereal Chemists, Inc., St. Paul, Minn.).

A differential scanning calorimeter (DSC) has the ability to measure or calculate the quantity of energy (as heat) required to dissociate the structures holding starch granules together. Sometimes, this heat energy is determined mathematically from a temperature difference. This process of dissociation, called gelatinization, is endothermic (i.e. requiring the input of energy). Normal starches undergo two thermal transitions during gelatinization: one transition at a lower temperature is attributed to the disruption of order between starch chains (dissociation of starch crystallites and unwinding of starch double helices) and a higher temperature transition attributed to the dissociation of amylose-lipid complexes. The amylose-lipid transition is not observed for waxy starches as they have no amylose and contain little lipid. A DSC has the ability to measure or calculate the quantity of energy (as beat) required to re-dissociate a retrograded starch paste which has partially reorganized into double-helical and crystalline structures. This energy (Enthalpy) involved is a measure of starch stability and may vary depending on the solids content of the starch, the storage temperature, and the aqueous environment of the starch. The gelatinization temperature range and enthalpy of the starch component of waxy-E starch is indistinguishable from the gelatinization of the starch component of either waxy or normal starch. I some cases, an amylose-lipid dissociation endotherm is observed, however the magnitude of this endotherm (as die enthalpy) is significantly smaller than observed for normal starch; These results provide additional evidence that the waxy-E starch may be isolated from waxy-E seed using existing processing technologies, which often involve heating steps exceeding 50° C. The retrogradation temperature range of waxy-E starch is indistinguishable from the retrogradation temperature range of either waxy or normal starch. However, the retrogradation enthalpy may be observed to be between waxy and normal starch though this largely depends on the starch concentration and the temperature to which the starch was heated during gelatinization: higher heating temperatures during gelatinization result in lower starch retrogradation enthalpies more than with lower heating temperatures (Liu, Q. and Thompson, D. B., 1998, Carbohydrate Research 314:221–235). Retrogradation enthalpies of waxy-E starches will approach those of waxy starches with increasing cooking temperature, decreasing starch content, or in general, increasing destructurization of the starch granules.

Assessment of the rheology of starch during starch gelatinization and after gelatinization are commonly conducted using varying types of instruments. Gelatinization of starch granules into pastes is commonly monitored by continuously shearing the sample as the sample is heated and cooled in a controlled manner. One instrument which does this is called a Rapid Visco Analyzer (RVA; Rapid Visco Analyser 4, Newport Scientific Pty. Ltd., Warriewood NSW, Australia). Rapid visco analysis of starch suspensions may be performed using a variety of standard heating and cooling protocols provided with the instrument (Anonymous. 1998. Ch. 7, General applications, in the Applications Manual for the Rapid Visco Analyzer, Newport Scientific Pty. Ltd., Warriewood NSW, Australia, p. 36) or programmed for specific heating, cooling, and shear rate regimes. The waxy-E starches begin to develop viscosity at slightly higher temperatures than waxy starch during initial heating. The waxy-E starches also develop a peak viscosity at later times than waxy starch, and retain more of the developed viscosity than does waxy starch. All waxy-E starches develop a higher peak viscosity than normal starch within useful concentrations of starch solids. Finally, waxy-E starches develop higher viscosity pastes than waxy starch as the paste is cooled. Thus, more of the viscosity developed by the waxy-E starch is retained during cooking and is reestablished after cooking than is observed for waxy starch. As the retention of viscosity and improvement of starch stability to heat and shear is often a primary reason for starch chemical modification, the present invention may be viewed as a natural alternative to chemically modified starches or as a feedstock for improved chemically modified starches. Such starches could also be used in countries where some chemically modified food starches are prohibited by law.

In addition to shear viscosity measurements, more complex assessment of the rheological quality of a starch paste may be conducted using an oscillatory shear rheometer which is able to probe the elastic and viscous nature of viscous pastes or gels. These descriptors and their derivation are described in detail by Biliaderis (1992, Characterization of starch networks by small strain dynamic rheometry, in Developments in Carbohydrate Chemistry, R. J. Alexander and H. F. Zobel, eds. American Association of Cereal Chemists, St. Paul). Generally, a force deforming an object can be divided into two parts: one part which is lost to the material during deformation, and one part which is retained by the sample and returned when the deforming force is removed. When normalized for the area over which the force is applied and normalized for the strain (the amount the sample is deformed relative to the thickness or height of a sample), the total force is termed the "complex modulus" (abbreviated G*), the elastic, conserved, force is termed the "storage modulus" (abbreviated G'), and the lost force is termed the "viscous modulus" (abbreviated G"). The relationship between G*, G', and G" is:

$$G^* = \sqrt{G'^2 + G''^2}$$

Above a given strain, the ability of a starch paste to store the force applied to it decreases due to an decrease in long-term interactions (longer than the time taken per deformation cycle) between starch molecules; the strain at which this begins to occur is termed the "yield strain" of the material. For strong biopolymer gels, like amylose, the yield strain is often below 1% (Clark, A. H. and Ross-Murphy, S. B., 1987, Advances in Polymer Science 83:57–192). Below the yield strain, the G*, G', and G" remain relatively constant, a small, incremental increase or decrease in the strain applied to the material will have no effect on these values. Changes in the paste with strain may also be evaluated by observing the phase angle of the material. The phase angle represents how close the material is to a perfectly elastic material (with a phase angle of 0 degrees) or to a perfectly viscous liquid (with a phase angle of 90 degrees). As the strain on a sample increases beyond the yield strain of a material, the phase angle of a material increases due to a decrease in the long-term structure of the material, i.e. the links between molecules break under high strain. The frequency dependence of the elastic modulus and viscous modulus may also be examined with a rheometer. The dependence of the elastic and viscous moduli on measurement frequency is an indication of the nature of the polymer system: strong frequency dependence indicates that the system is more related to a dispersion of randomly-interacting polysaccharide molecules with low long-term order and low gel-like character, while weak frequency dependence indicates that the structure within the system is relatively fixed which is a characteristic of polymer gels with high gel-like character. Thus, using continuous shear measurements and oscillatory rheological measurements, the quality of starch pastes may be assessed. Below the yield strain, waxy-E starch pastes have a higher G' than waxy starch. Additionally, below the yield strain the lower phase angles of waxy-E starch pastes compared to waxy pastes indicates that the waxy-E pastes have a higher degree of elastic character. Further, the waxy-E starch pastes have a lower frequency dependence than do pastes of waxy starch, indicating that the waxy-E pastes have a higher gel-like character than do waxy starch pastes. A result of these characteristics is an indication of the behavior of the waxy-E starch when at rest or under low deformations: waxy-E starches have a lower likelihood to flow under their own weight and produce pastes which are not as noticably stringy and cohesive as are those of waxy starch.

Assessment of starch gel characteristics may be examined using penetrometers and texture analyzers which have the ability to penetrate or withdrawl a probe from a solid or semi-solid sample and measure the force required to move the probe a given distance. The waxy-E starches form weak gels at relatively low concentrations (10% w/w starch). Further, gels of waxy-E starch are unique: they do not fracture and they return to their original shape to a large extent after the deformation. A measure of this return to the original shape is the resilience (or resiliency) of the gel, is calculated as the ratio of the positive force during probe withdrawl to the positive force during probe penetration (the firmness). Normal starch gels do not exhibit these qualities:

they set into firm gels which fracture under low deformations and remain deformed after the force acting on the gel has been removed.

The physical properties and benefits of starches are also commonly tested against other starches in applied situations, normally as part of a food or industrial formulation. Often, starches behave differently when in the presence of dissolved solutes and other materials such as proteins and lipids. Tests in formulations help to confirm the benefits of a particular starch. From examination of the waxy-E starches in a lemon pie filling formulation, the viscosity and rheological properties of the waxy-E starches are found to be consistent with those properties observed with the isolated starch in pastes. The similarity in the rheological properties of the fillings after they have been stored for one day and one week additionally shows that the waxy-E starches have useful low temperature stability.

Starch Chemical Structure Analysis

Starches may also be differentiated and evaluated based on the structures of the molecules. One way to assess the differences between the physical structures of starch molecules is by examination of the distribution of the lengths of their chains. This distribution is commonly assessed using high-performance gel permeation chromatography (GPC) (Klucinec and Thompson, 1998, Cereal Chemistry 75:887–896) or high-performance anion-exchange chromatography (HPAEC) with pulsed amperometric detection (PA) (Jane et al, 1999, Cereal Chemistry 76:629–637). Other chromatographic or similarly functioning methods of detection are known to those ordinarily familiar with the art. It is well-known that additional mutations in the starch biosynthetic pathway affect the structure of the starch molecules, and that the changes in the structure of the starch molecules due to these additional mutations affect the physical properties of the starch (Jane and Chen, 1992, Cereal Chemistry 69:60–65 ; Jane et al., 1999, Cereal Chemistry, 76:629–637; Klucinec and Thompson, 1998, Cereal Chemistry 75:887–896; Klucinec and Thompson, 1999, Cereal Chemistry 76:282–291; Klucinec and Thompson, 2001a, Cereal Chemistry, accepted; Klucinec and Thompson, 2001b, Cereal chemistry, accepted). Using HPAEC-PAD, no differences are observed between the debranched waxy-E starches, debranched waxy starch, or debranched normal starch in their chain length distribution up to a degree of polymerization of 50 glucose units. This result indicates that alteration of the shorter chains of the waxy-E starch are not responsible for its unique physical behavior, unlike waxy amylose-extender starch which has an altered distribution of shorter chains.

GPC may also be used to assess the amylose content of the starch since amylose molecules are typically longer in length than those of amylopectin, and GPC detection and separation methods are commonly optimized to examine such chain lengths. HPAEC-PAD chromatography methods are typically insensitive to chains longer than 50 to 100 glucose units in length due to the limits of the detection method. Using high performance GPC with a chromatography column set chosen for the examination of longer starch chains, debranched waxy starches are observed to elute between 43 minutes and 53 minutes, while debranched normal starch elutes between 30 minutes and 53 minutes. The difference in the initial elution time of debranched waxy starch and debranched normal starch is due to the amylose of the normal starch, which elutes between 30 and 43 minutes. Debranched waxy-E starches have a low but reproducible amount of starch chains which elute before 43 minutes, indicating that they contain long chains not present in the waxy starches. This long chain material is approximately 24%–28% of the total mass for normal starch and for waxy-E starches ranges from 1.5% to about 8% of the total carbohydrate mass. The long chain material is believed to be amylose. The presence and quantity of this long chain material is consistent with the spectrophotometric amylose content measurements described earlier by iodine staining.

Plant Hybrid Production

The production of a hybrid plant involves combining the genetics of at least two inbred plants. The development of a hybrid corn variety involves three steps: (1) the selection of plants from various germplasm pools; (2) the selfing of the selected plants for several generations to produce a series of inbred lines, which, although different from each other, breed true and are highly uniform; and (3) crossing the selected inbred lines with unrelated inbred lines to produce the hybrid progeny (F1). During the inbreeding process in corn, the vigor of the lines decreases. Vigor is restored when two unrelated inbred lines are crossed to produce the hybrid progeny. An important consequence of the homozygous and homogeneous nature of the inbred lines is that the hybrid between any two specific inbreds will always be the same. Once the inbreds that give a superior hybrid have been identified, the hybrid seed can be reproduced indefinitely as long as the homogeneity of the inbred parents is maintained. The inbred mutant of the present invention is recessive. The recessive nature of the gene makes it necessary in the production of hybrid crops such as maize and hybrid wheat to produce the event in two inbreds. Alternatively, the hybrid crop may be made with another plant such that the mutant of the present invention is dominant or semi-dominant to those traits contained in the other parent plant. These two inbreds should be suitably crossed to get a hybrid that is high yielding and has acceptable commercial agronomic characteristics. For example but not as a limitation in maize one inbred could be from the stiff stalk family such as B73 and the other could be a Mo17 or other Lancaster type. Likewise breeders with ordinary skill in the art of plant breeding can select the elite lines that should be mutagenized to make an acceptable hybrid cross. Alternatively the inbreds in existing commercial inbred waxy lines can be used to form two new hybrids each containing the desired mutant. In this case the waxy-E properties of the hybrid will be mid-way between the amylose contents of the two inbreds. The inbreds containing the desired physical and structural traits of a low amylose starch can be selected and crossed with another inbred having the same mutations, different mutations, or additional mutations to make the hybrid. Other alternative breeding methods can be used with the inbred to form hybrids or breeding populations.

This invention is directed primarily at alteration of starch in grain of plants using genes from donor species of plants. Alternatively the invention can be used to alter starch of other recipient plants using genes from monocotyledonous plants. This can be achieved by mutableness or breeding or a variety of known techniques which are known in the art as genetic engineering. Making hybrid proteins with different glucan chain-extending properties is also possible.

EXAMPLES

Example 1

Starch Isolation

Starch is isolated from maize seeds based on the following procedure modified from Eckhoff et al (1996, Cereal Chemistry. 73: 54–57) and Singh et al (1997, Cereal Chemistry 74: 40–48). Corn kernels (100 g) are mixed with 200 mL of an aqueous steeping solution (0.3% sodium metabisulfite and 0.5% lactic acid) in a flask. The flask is then stoppered and the mixture then held at 50° C. for 48 h. After 48 h the corn is rinsed once with water, transferred to the unmodified 64 fluid oz. jar of a commerical blender (Vita-Mix Commercial Food Preparing Machine, model VM0101, Vita-Mix Corp., Cleveland, Ohio) along with 150 mL of water, and then ground at variable speed setting "5" for 4 min, with a pause for 10 sec every min to improve homogenization. The ground sample is transferred to a #7 mesh sieve snugly fit atop a 4L bucket (Encore Plastics Corp., Byesville, Ohio). Additional starch is removed from the sample atop the mesh by rinsing it with 150 mL of water. The entire assembly is then shaken for 5 min using a sieve shaker (CSC-Meinzer sieve shaker, Model 184800-000, CSC Scientific Company, Inc., Fairfax, Va.) on setting "9" and to which 100V is delivered through the use of a variable transformer (Powerstat variable transformer, 117C series, Superior Electric, Bristol, Conn.). During shaking an additional 200 mL of water is added to rinse the sample. The material passing through the sieve is returned to the blender jar and then ground at variable speed setting "9" for 2 min, with a pause for 5 sec every 30 sec to improve homogenization. The resultant sample is allowed to settle for 10 min, after which time 250–300 mL of liquid is decanted. The remainder of the sample is transferred to a 200 mesh sieve snugly fit atop a 4L bucket. The entire assembly is then shaken for 5 min using a sieve shaker as before, during which time the sample is washed with the previously decanted liquid and an additional 600 mL of water. The material passing through the sieve is allowed to settle for at least 1.5 h, at which time most of the liquid is first decanted from the sample and a portion of which is then returned to the sample to bring the specific graivty to 1.040–1.045. The starch-protein slurry is pumped at 55 mL/min along a 2 inch×96 inch (W×L) aluminum channel placed at a 0.0104 ratio of rise to run. The decanted liquid is pumped along the table immediately following the starch-protein slurry, followed by 125 mL of water. Yellow colored protein impurities are moved along the table, when necessary, during the time when the decanted liquid and 125 mL of water are pumped along the table by using air squeezed from an empty wash bottle. The starch, as the white residue remaining on first 90 inches of the table, is allowed to air dry on the table for at least 18 h and is then scraped from the table into a plastic weighing dish. The starch in the dish is dried for an additional 18 h at 30° C. in a forced air convection oven, after which it is ground into a fine podwer using a retail coffee grinder and then transferred into a storage bottle. Starch was isolated on larger scales according to Singh et al (1997, Cereal Chemistry 74: 40–48) as needed.

Example 2

Starch Morphology and Color

This experiment was conducted to illustrate the effect of the low amylose content of waxy-E starch on the iodine staining properties of the waxy-E starch.

The waxy-E starch granules extracted as described in Experiment 1 were studied microscopically and compared to known waxy and normal starches. Additionally commercial normal maize (Cerestar-USA, C*Gel 03420) and waxy maize starch (Cerestar-USA, C*Gel 04230) samples were also examined. Light microscope studies showed all of the starches were shaped similarly and all were highly birefringent under cross-polarized light. The iodine staining of the starches is tested by suspending 5 mg of starch in 2.85 mL of water. A stock iodine-iodide solution (2 g/L iodine, 20 g/L potassium iodide) is diluted 100-fold in water. Any aliquot (0.15 mL) of the diluted iodine-iodide is stock solution is added to the starch suspension. The starch color was visually examined (FIG. 1). All waxy-E starches stained a dark bluish-purple with the addition of iodine stain and could not be distinguished from normal starches. Only the waxy starches stained a light reddish-brown color. The uniformity of the coloration across starch granules was examined using a light microscope after the addition of three additional 0.15 mL aliquots of diluted iodine-iodide stock. When the suspensions in FIG. 1 were examined under the microscope, the waxy-E starches stained predominantly bluish-purple and could not be distinguished from normal starch by their iodine staining character (FIG. 1). The commercial waxy starch could be clearly differentiated from the lab-isolated waxy starches by its contamination with normal starch. For the commercial waxy starch sample every microscope field contained one or two bluish-purple staining starch granules.

Example 3

Amylose Content & Amylopectin Chain Ratio

These tests were conducted to demonstrate that waxy-E starches may be differentiated from waxy and normal starches using two amylose quantitation techniques: iodine binding and gel permeation chromatography.

The amylose content of the starches is tested using an adaptation of the method of Morrison and Laignelet (1983, Journal of Cereal Science 1: 9–20). Starch granules (8 mg) in a microcentrifuge tube are dispersed in 0.4 mL of 90% dimethyl sulfoxide by heating in a boiling water bath for 1 h. Samples are agitated every 10 min during heating. The dispersed starch is precipitated by adding 1.6 mL of ethanol and centrifuged at 3000×g for 5 min in a microcentrifuge at room temperature. The supernatant material is discarded. The starch pellet is washed twice with 1.0 mL of ethanol and once with 1.0 mL of acetone, centrifuging the sample as described above each time. The non-granular starch, free of native lipids which interfere with amylose determination, is allowed to dry in the uncapped microcentrifuge tube for at least 2 hours. After drying, the non-granular starch is dispersed in 1.0 mL of a solution of 10% 6M urea and 90% dimethyl sulfoxide by heating in a boiling water bath for 1 h. Samples are agitated every 10 min during heating. The dispersed sample (0.05 mL) is mixed with 10 mL of water and 0.2 mL of an iodine-iodide solution (2 g/L iodine, 20 g/L potassium iodide). Blank solutions without carbohydrate were prepared in the same manner. Normal corn amylose standards (0.05 mL of 1, 2, 4, 6, and 8 mg/mL stock solutions) were made from lab-isolated amylose of at least 95% purity using the method of Klucinec and Thompson (1998, Cereal Chemistry 75: 887–896). The purity of the amylose was confirmed using the gel permeation chromatography method of Klucinec and Thompson (1998, Cereal Chemistry 75: 887–896). Waxy maize, isolated from a known GBSS-absent waxy (null) mutant, was used for an amylopectin standard [0.05 mL of 2, 4, 6, and 8 mg/mL stock solutions in addition to 0.1 mL of the 6 mg/mL stock solution (12 mg/mL), and 0.1, 0.15, and 0.2 mL of the 8 mg/mL stock solution (16, 24, and 32 mg/mL, respectively)]. The additional DMSO in the 16, 24, and 32 mg/mL amylopectin standards has no effect on the linearity of the subsequently constructed standard curve. The spectrophotometer is zeroed at 635 nm with the blank solution, after which the absorbance of the remaining solutions is measured. The standard curve used for amylose quantitation is of the form:

Amylose (in micrograms)={(Absorbance of iodine solution at 635 nm)−[(Slope of amylopectin standard curve in micrograms$^{-1}$)×(Total Carbohydrate of Solution in micrograms)]}/[(Slope of amylose standard curve in micrograms$^{-1}$)−(Slope of amylopectin standard curve in micrograms$^{-1}$)]

The apparent amylose in micrograms is converted to a percentage of the total starch by dividing the value obtained by the carbohydrate content of the solution and then multiplying by 100. Three independent analyses for each starch were conducted. The results are presented in Table 7.

Figure 2:
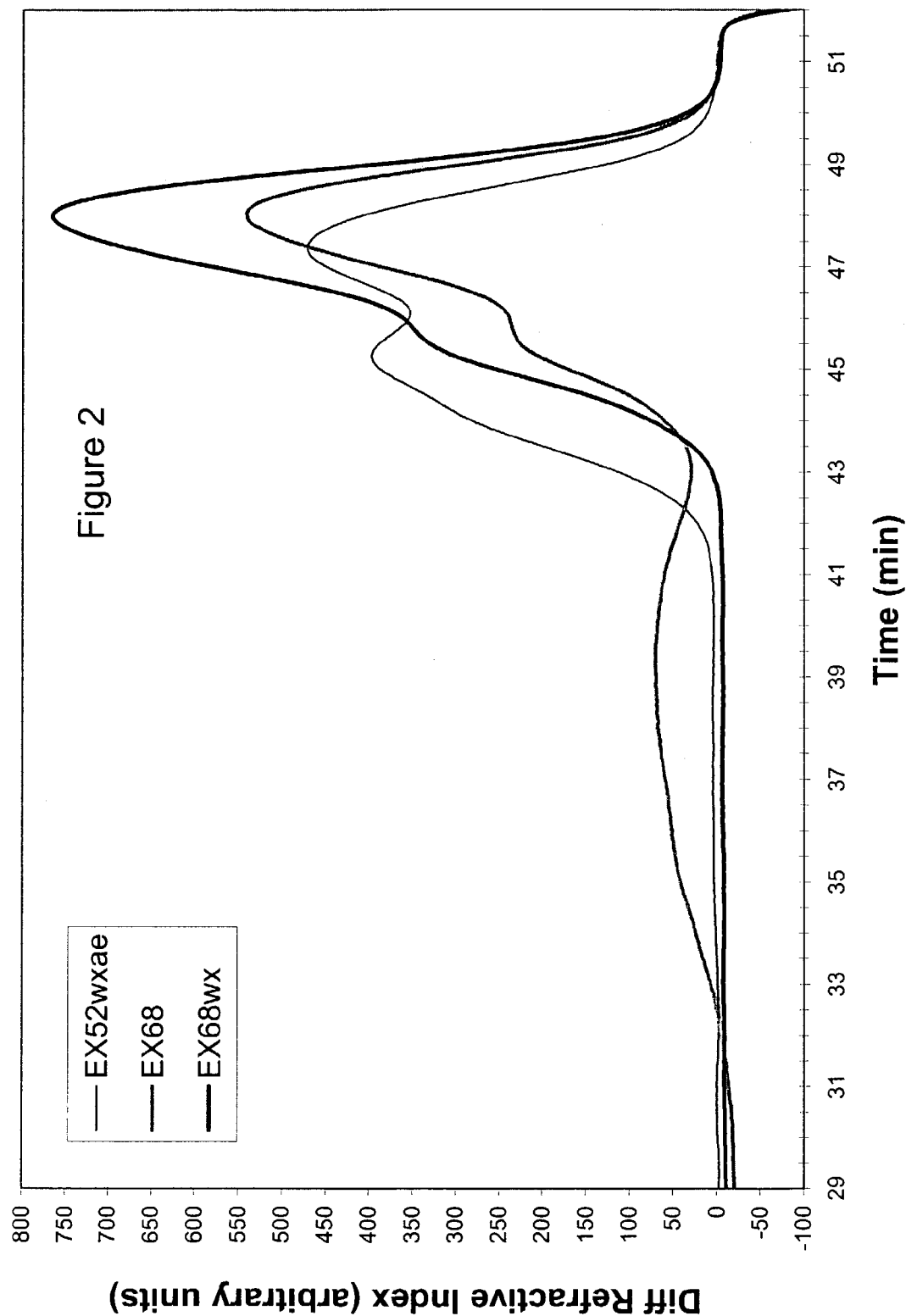
FIG. 2. High-performance size-exclusion chromatography of debranched normal starch and debranched waxy starch from the EX68 background and debranched EX52wxae starch. Differential refractive index response is plotted against elution time.
Figure 3:
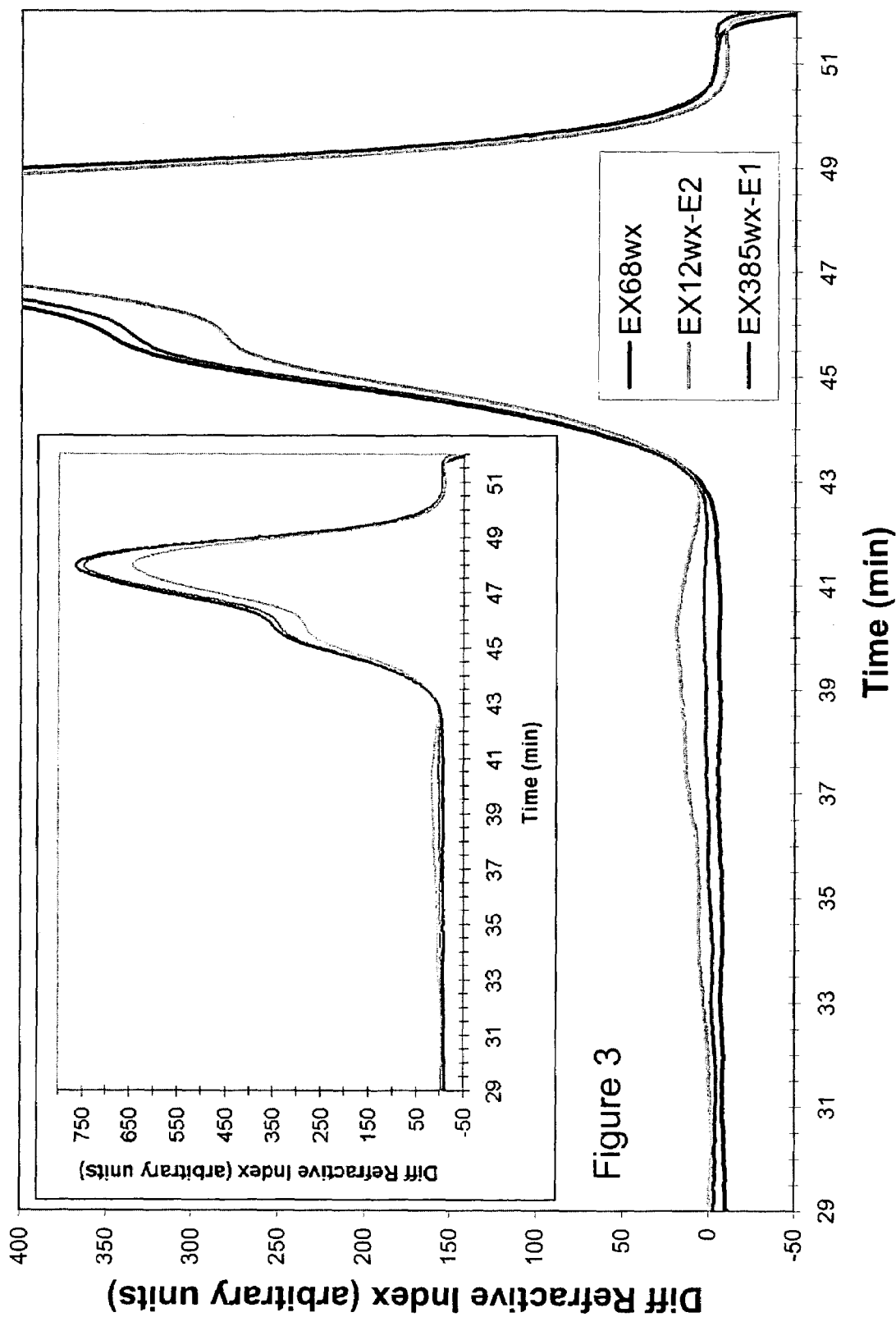
FIG. 3. High-performance size-exclusion chromatography of debranched waxy starch and debranched waxy-E starches. The inset figure shows the full response of the detector. In both drawings, the differential refractive index response is plotted against elution time.

For analysis of the amylose content by gel permeation chromatography, samples consisted of samples of normal starch (lab isolated and a commercial normal starch from Cerestar-USA, C*Gel 03420), waxy starch (lab isolated and a commercial waxy starch from Cerestar-USA, C*Gel 04230), and lab-isolated waxy-E starches. Starch granules (5.5 mg) in a microcentrifuge tube are dispersed in 0.4 mL of 90% dimethyl sulfoxide by heating in a boiling water bath for 1 h. The sample is agitated every 10 min during heating. The dispersed starch is precipitated by adding 1.6 mL of ethanol and centrifuged at 3000×g for 5 min in a microcentrifuge at room temperature. The supernatant material is discarded. The starch pellet is washed twice with 1.0 mL of ethanol and once with 1.0 mL of acetone, centrifuging the sample as described above each time. The resultant non-granular starch is allowed to dry in the uncapped microcentrifuge tube for at least 2 h. The dry non-granular starch is mixed with 0.9 mL of water and 0.1 mL of 100 mM sodium acetate (pH 4.5) and heated in a boiling water bath for 1 hour. The sample is mixed every 10 min during boiling. After heating, the sample is cooled to 40° C. in a water bath. An isoamylose suspension (0.001 mL; isolated from *Pseudomonas* sp., Megazyme International Ireland Ltd, Co. Wicklow, Ireland) is added and the sample is inverted several times before it is returned to the 40° C. water bath. After 18 h, the sample is heated in a boiling water bath for 5 min to inactivate the enzyme. The sample is allowed to cool after which time 0.2 mL of digest is added to 1.8 mL of DMSO. For injection, 0.5 mL is centrifuged at 9,000×g. High-performance GPC is conducted in conjunction with a differential refractive index detector as part of a chromatography system (Waters Breeze HPLC system consisting of a 1515 Isocratic HPLC Pump, a Waters 2414 Differential Refractive Index detector, and a Rheodyne model 7725i injector with a 0.250 mL injection loop, Waters Corporation, Milford, Mass.). Three PL-Gel 10 micrometer Mixed-B (300×7.5 mm) analytical columns (Polymer Laboratories, Amherst, Mass.) and one PL-Gel 10 micrometer Mixed-B (100×7.5 mm) guard column (Polymer Laboratories, Amherst, Mass.) are used to separate the component chains of the starch. The system is operated at a flow rate of 0.5 mL/min with a mobile phase of 0.1% lithium bromide in DMSO. The system is calibrated with standards of maltose (Sigma-Aldrich, St. Louis, Mo.), maltotriose (Sigma-Aldrich, St. Louis, Mo.), maltoheptaose (Sigma-Aldrich, St. Louis, Mo.), and pullulan standards with weight average molecular weights of 788000, 212000, 47300, 22800, 11800, and 5900 from a carbohydrate standards kit (Polymer Laboratories, Amherst, Mass.). All injections are 0.200 mL. Monitoring of the chromatograms and analysis of the data is done using the accompanying software (Breeze v. 3.20). Chromatograms of EX68wx and EX68 normal starch are shown in FIG. 2. Chromatograms of EX68wx, EX385wx-E1, and EX12wx-E2 are shown in FIG. 3. From FIGS. 2 and 3 it is clear that negligible area is observed before 43 minutes for waxy starch. For normal starch, a minimum in the chromatogram is observed at 43 minutes; this minimum was used as a demarcation between the elution of amylose and debranched amylopectin from the system: amylose elutes before 43 minutes and debranched amylopectin elutes after 43 minutes. The percentage of the area eluting before a time of 43 minutes in relation to the total area is calcualted and is used as a measure of the amylose content (w/w) of the starch. In cases where small areas were observed before 43 minutes, the time slices of multiple chromatograms were averaged and the relative areas preceeding and following 43.0 minutes for the average chromatogram were then calculated. Amylose contents calculated in this way from all chromatograms are presented in Table 7.

From the GPC chromatograms, the AP Ratio (Amylopectin Chain Ratio) was calculated. The AP Ratio is the ratio of the area of the chromatogram between a time of 46.01667 minutes and 51 minutes to the area of the chromatogram between a time of 43.01667 minutes and 46 minutes.

TABLE 7

Amylose Content of Starches

| Sample | Amylose Content Spectrophotometric (% w/w) | High-Performance GPC[a] (% w/w) | AP Ratio High-Performance GPC[a] |
|---|---|---|---|
| Normal | | | |
| EX68 Normal | 23.3 ± 1.5 | 27.0 (1) | 3.5 (1) |
| C* Normal | 20.0 ± 0.7 | 28.7 (1) | 3.4 (1) |
| wx starch | | | |
| EX68wx | 0.4 ± 0.1 | 0.2 (3) | 3.7 (3) |
| C* waxy | 1.7 ± 0.3 | 0.2 (2) | 3.7 (2) |
| wxae starch | | | |
| EX52wxae waxy-E starch | 17.3 ± 1.0 | 3.1 (2) | 1.3 (2) |
| EX56wx-E1 | 1.4 ± 0.2 | 1.3 (3) | 3.6 (3) |
| EX385wx-E1 | 2.4 ± 0.1 | 2.2 (3) | 3.7 (3) |
| EX78wx-E1 | 2.5 ± 0.2 | 2.3 (3) | 3.7 (3) |
| EX12wx-E2 | 6.5 ± 0.4 | 7.2 (1) | 3.7 (1) |

[a]The number of injections utilized for the calculation of the amylose content of the starch is shown in parentheses.

The results show that the amylose of EX56wx-E1, EX385wx-E1, EX78wx-E1, and EX12wx-E2 starches is significantly less than normal starch. Additionally, the results of these tests clearly show that the low amylose starches have an amylose content which is also higher than the pure lab-isolated waxy starches. The higher amylose content of the C* waxy starch compared to the lab-isolated waxy starches is likely to be an artifact of normal starch contamination from commercial isolation processes. Additionally, the waxy-E starches may be divided into two groups based on amylose content: one group which has an amylose content between 1% and 3% (wx-E1 starches; EX56wx-E1, EX385wx-E1, EX78wx-E1) and another group which has an amylose content between 6% and 8% (wx-E2 starches; EX12wx-E2). Further, notice that for the EX52wxae starch the amylose contents determined by the two methods differ considerably. This is because wxae starches have an altered amylopectin structure which is able to produce some blue color resulting in high spectrophotometrically-determined amylose contents. However, when the same starch is analyzed by chromatography, a very low proportion of the total area elutes from the chromatograph before a time of 43 min, and this area is actually part of a peak which is attributable to the amylopectin of this starch (FIG. 2). Thus, there is no true amylose in the wxae starch. For the low amylose starches, the distribution of starch chains eluting after 43 minutes is indistinguishable from waxy starch; long amylopectin chains are not responsible for the observed amylose of waxy-E starches. Thus the amylose of the waxy-E staches may be quantitated by both by spectrophotometric and chromatographic measurement techniques, and both techniques yield similar amylose content values. Additionally, to the best of our knowledge the low amylose contents of the waxy-E starches are not attributable to long chain amylopectin. Further, the results show that the AP Ratio is within 0.5 of the AP ratio of the normal starches. The wxae starch has an AP Ratio lower than 1/2 that of the normal, waxy, and waxy-E starches, indicating the severe effects that the ae mutation has on the chain disrtibution of amylopectin.

Example 4

Starch Gelatinization—Pasting Viscosity Profiles at pH 6.5—2.5 min at 95° C.—waxy-E, waxy, and Normal Starches This experiment was conducted to demonstrate that the waxy-E starches have unique gelatinization behavior. Assessment of the viscositiy changes during starch gelatinization are commonly conducted using a Rapid Visco Analyzer.

A pH 6.5 buffer solution is prepared as described in the "Applications Manual for the Rapid Visco Analyzer" (Anonymous. 1998. Ch. 7, General applications, in the Applications Manual for the Rapid Visco Analyzer, Newport Scientific Pty. Ltd., Warriewood NSW, Australia, p. 20). Both p-hydroxybenzoic acid methyl ester (0.8 g; Sigma-Aldrich, St. Louis, Mo.) and n-propyl p-hydroxybenzoate (0.2 g; Sigma-Aldrich) are added to a 250 mL beaker, to which 150 mL of water is added. The suspension is brought to a boil with stirring to dissolve the solids. The hot solution is added to 700 mL of distilled water in a 1000 mL graduated cylinder, after which the volume is brought to 1000 mL. To this solution is added: 18.9 g of dibasic sodium phosphate heptahydrate (Fisher Scientific, Pittsburgh, Pa.), 2.0 g of sodium benzoate (Sigma-Aldrich), and 2.7 g of anhydrous, granular citric acid (Sigma-Aldrich). The mixture is stirred until all of the solids are dissolved. Using a properly calibrated pH meter, the mixture is then adjusted to pH 6.5 using citric acid if the pH is greater than 6.5 or dibasic sodium phosphate is the pH is below 6.5. For each starch, a known mass of starch (on a dry weight basis) is weighed into an aluminum rapid visco analysis cup (Newport Scientific Pty. Ltd). The sample is then brought to a total mass of 28 g with pH 6.5 buffer. The RVA paddle is then added to the RVA cup and the paddle then agitated in an up and down motion for 15 seconds to suspend the starch. The cup, paddle, and starch suspension are then transferred to the RVA and the instrument analysis procedure is immediately initiated. As the starch slurry is mixed at 960 rpm for the initial 10 seconds and 160 rpm for the remainder of the RVA analysis while the temperature is modulated using the controlling/analysis software (Thermocline for Windows v. 2.2, Newport Scientific Pty. Ltd.) per the following Standard 1 Version 5 (December 1997) heating and stirring program: hold at 50° C. for 1 min, heat to 95° C. over 3.7 min, hold at 95° C. for 2.5 min, cool to 50° C. over 3.8 min, and hold at 50° C. for 2 min. This method, when used with a Rapid Visco Analyzer 4 instrument is the RVA Standard Method.

For this Example, 1.4 g of starch on a dry weight basis was used for all tests.

Figure 4:
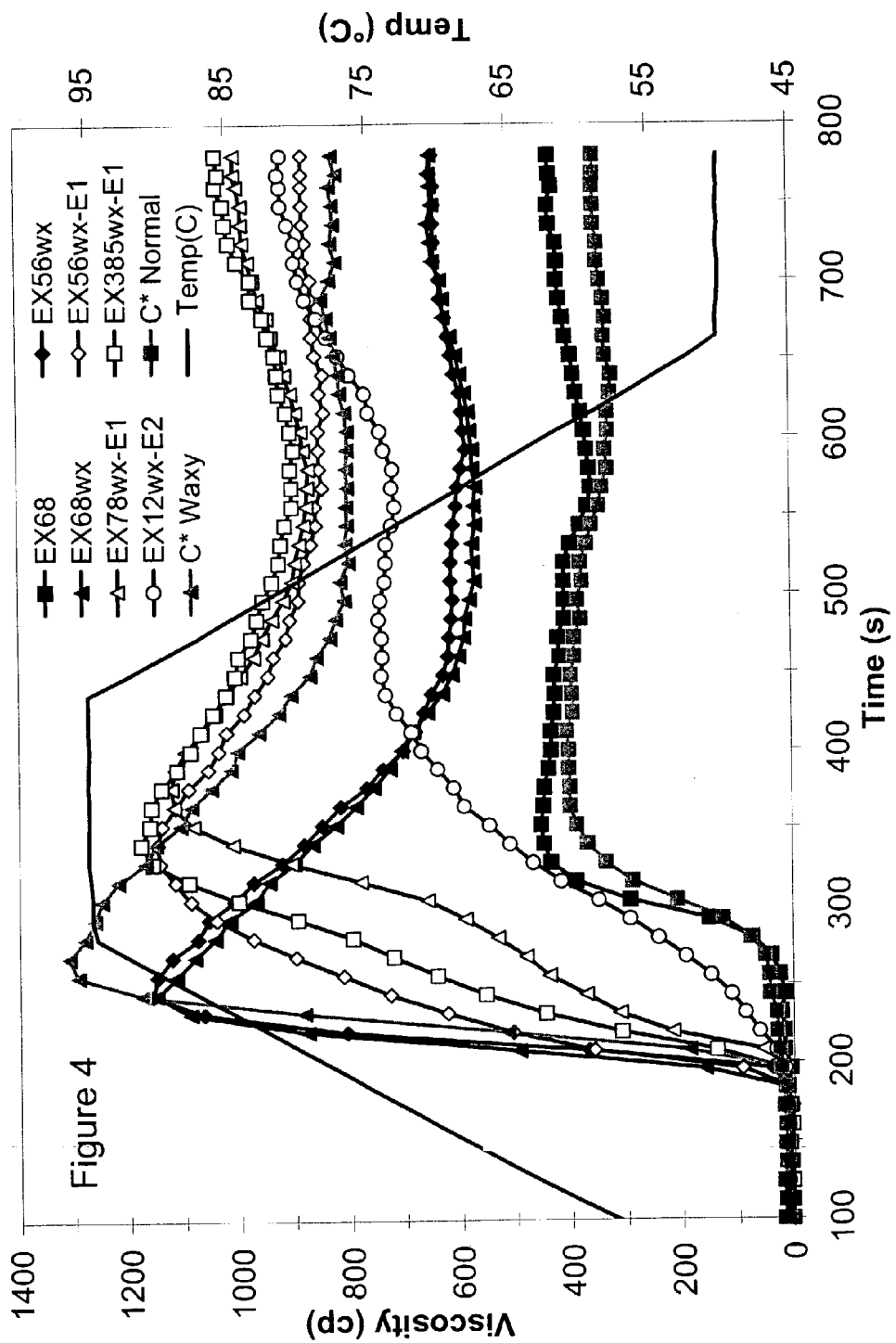
FIG. 4. RVA viscograms of 5% starch suspensions in a pH 6.5 buffer with a 2.5 min cooking step at 95° C. Viscosity and temperature are plotted against time.

Analysis of the viscogram is conducted using the accompanying software. Data from three analyses of each starch are presented in Table 8, including samples of commercial starches obtained from Cerestar-USA (normal starch, C*Gel 03420; waxy starch C*Gel 02430). Example viscograms are presented in FIG. 4.

TABLE 8

Rapid Visco Analysis Profile Data - Ph 6.5–2.5 min @ 95° C.

| Sample | Peak Viscosity (cp) | HP Viscosity (cp) | Breakdown (cp) | B/P[a] (%) | Final Viscosity (cp) | Setback (cp) | Peak Time (min) | Pasting Temp (° C.) |
|---|---|---|---|---|---|---|---|---|
| Normal | | | | | | | | |
| EX68 | 461 ± 13 | 435 ± 18 | 101 ± 4 | 21.9 | 428 ± 6 | 68 ± 6 | 6.1 ± 0.2 | 94.0 ± 1.6 |
| C* Normal wx starch | 305 ± 4 | 386 ± 10 | 90 ± 4 | 29.6 | 333 ± 4 | 28 ± 3 | 6.6 ± 0.3 | 94.7 ± 0.5 |
| EX68wx | 1133 ± 3 | 616 ± 4 | 573 ± 14 | 50.6 | 633 ± 10 | 73 ± 7 | 4.1 ± 0.0 | 75.5 ± 0.5 |
| EX56wx | 1162 ± 18 | 635 ± 14 | 580 ± 3 | 49.9 | 646 ± 23 | 65 ± 6 | 4.1 ± 0.1 | 76.9 ± 0.4 |
| C* waxy waxy-E starch | 1293 ± 7 | 857 ± 24 | 521 ± 3 | 40.3 | 804 ± 3 | 33 ± 6 | 4.4 ± 0.1 | 77.5 ± 0.1 |
| EX56wx-E1 | 1149 ± 12 | 958 ± 16 | 324 ± 11 | 28.2 | 862 ± 15 | 37 ± 4 | 5.7 ± 0.1 | 76.1 ± 0.4 |
| EX78wx-E1 | 1123 ± 10 | 1001 ± 10 | 269 ± 10 | 24.0 | 956 ± 27 | 102 ± 22 | 6.1 ± 0.1 | 78.8 ± 0.6 |
| EX385wx-E1 | 1171 ± 22 | 1004 ± 15 | 290 ± 21 | 24.8 | 1013 ± 13 | 132 ± 7 | 5.8 ± 0.2 | 77.5 ± 0.1 |
| EX12wx-E1 | 690 ± 28 | 710 ± 23 | −121 ± 5 | 17.5 | 906 ± 24 | 337 ± 9 | 7.0[b] | 88.8 ± 1.1 |

[a]Percentage breakdown relative to the peak viscosity. B/P = {[Breakdown (cp)]/[Peak Viscosity (cp)]} × 100
[b]Peak time exceeded 7.0 minutes.

All of the low amylose starches and waxy-E starches had a significantly higher peak viscosity and higher final viscosity than the normal starches, indicating that all of the waxy and waxy-E starches excel in the development of viscosity at relatively low starch concentrations. Additionally, all waxy-E and waxy starches had a pasting temperature lower than that of the normal starches, indicating that all of these starches begin to build viscosity earlier than do the normal starches.

The waxy-E starches differed from the waxy starches in many respects (Table 8). All of the low amylose starches had a breakdown viscosity less than waxy starches; this is true when viewed as the absolute breakdown viscosity of the waxy-E starches but is also lower when the breakdown viscosity is viewed as a percentage of the peak viscosity (B/P, Table 8) of the waxy-E starch. Additionally, all of the waxy-E starches had a peak time later than those of the waxy starches. The waxy-E starches all had a final viscosity higher than those of the waxy starches. All of these observations indicate that the waxy-E starches develop viscosity more slowly than do waxy starches and also retain and continue to develop viscosity during processing over a longer period of time than do the waxy starches.

Further, the waxy-E starches may be divided into two groups of differing behavior: one group containing EX56wx-E1, EX78wx-E1, and EX385wx-E1 (wx-E1 Group, based on functional properties, see Table 8) and the other group containing EX12wx-E2 (wx-E2 Group, also based on functional properties, see Table 8). These groupings are the same as those described for the amylose content of these starches (see Example 3). Despite the common differences between all of these waxy-E starches and waxy starches noted above, the process by which each group obtains these properties happens in a different way. Starches of the wx-E1 Group develop a peak viscosity similar to that of the waxy starches, break down less than the waxy starches, and then set back an amount similar to waxy starches to result in a final viscosity higher than waxy starch. Starches of the wx-E2 Group plateau at a viscosity between the normal starches and waxy starches without noticable breakdown and then develop considerable setback viscosity to result in a final viscosity higher than waxy starch.

Example 5

Starch Gelatinization—Pasting Viscosity Profiles at pH 6.5—20 min at 95° C.—waxy-E, waxy, and Normal Starches This experiment was conducted to further demonstrate that the waxy-E starches have unique gelatinization behavior. Assessment of the viscositiy changes during starch gelatinization are commonly conducted using a Rapid Visco Analyzer.

Figure 5:
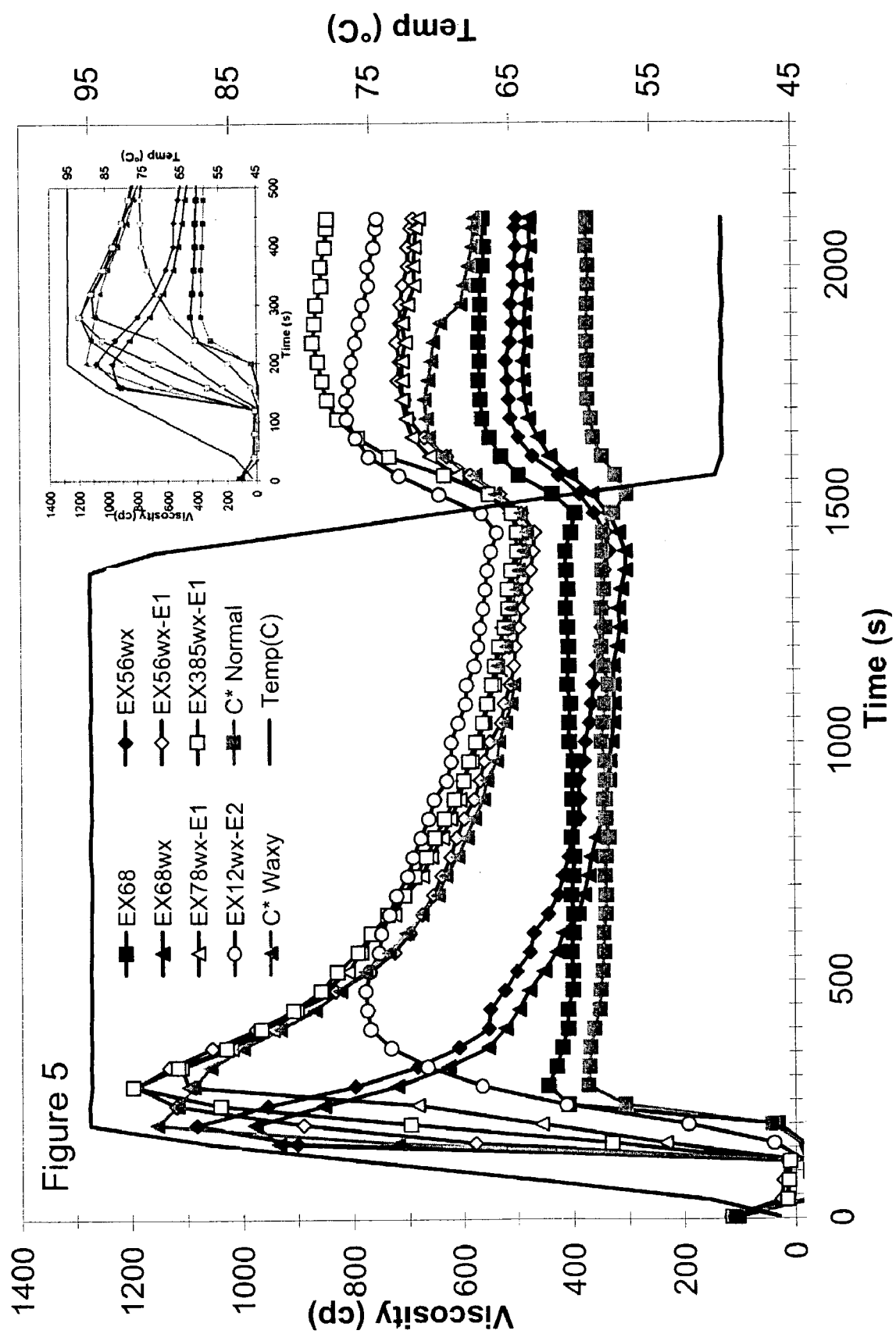
FIG. 5. RVA viscograms of 5% starch suspensions in a pH 6.5 buffer with a 20 min cooking step at 95° C. The inset figure shows the first 500 seconds of the analysis to better show the delayed development of viscosity of waxy-E starches relative to waxy starches. In both drawings, viscosity and temperature are plotted against time.

A pH 6.5 buffer solution is prepared as described in the "Applications Manual for the Rapid Visco Analyzer" (Anonymous. 1998. Ch. 7, General applications, in the Applications Manual for the Rapid Visco Analyzer, Newport Scientific Pty. Ltd., Warriewood NSW, Australia, p. 20). both p-hydroxybenzoic acid methyl ester (0.8 g; Sigma-Aldrich, St. Louis, Mo.) and n-propyl p-hydroxybenzoate (0.2 g; Sigma-Aldrich) are added to a 250 mL beaker, to which 150 mL of water is added. The suspension is brought to a boil with stirring to dissolve the solids. The hot solution is added to 700 mL of distilled water in a 1000 mL graduated cylinder, after which the volume is brought to 1000 mL. To this solution is added: 18.9 g of dibasic sodium phosphate heptahydrate (Fisher Scientific, Pittsburgh, Pa.), 2.0 g of sodium benzoate (Sigma-Aldrich), and 2.7 g of anhydrous, granular citric acid (Sigma-Aldrich). The mixture is stirred until all of the solids are dissolved. Using a properly calibrated pH meter, the mixture is then adjusted to pH 6.5 using citric acid if the pH is greater than 6.5 or dibasic sodium phosphate is the pH is below 6.5. For each starch, 1.4 g of starch (dry weight basis) is weighed into an aluminum rapid visco analysis cup (Newport Scientific Pty. Ltd). The sample is then brought to a total mass of 28 g with pH 6.5 buffer. As the starch slurry is mixed at 960 rpm for the initial 10 seconds and 160 rpm for the remainder of the RVA analysis while the temperature is modulated using the controlling/analysis software (Thermocline for Windows v. 2.2, Newport Scientific Pty. Ltd.) per the following ST-01 Revision 3 (November, 1998) heating and stirring program (Newport Scientific Pty. Ltd.): hold at 50° C. for 0.5 min, heat to 95° C. over 2.5 min, hold at 95° C. for 20 min, cool to 50° C. over 3.0 min, and hold at 50° C. for 9 min. Analysis of the viscogram is conducted using the accompanying software. Data from three analyses of each starch are presented in Table 9, including samples of commercial starches obtained from Cerestar-USA (normal starch, C*Gel 03420; waxy starch C*Gel 02430). Example viscograms are presented in FIG. 5.

All of the waxy-E starches and waxy starches had a significantly higher peak viscosity and higher final viscosity than the normal starches, indicating that all of the waxy and waxy-E starches excel in the development of viscosity at relatively low starch concentrations. Additionally, all waxy-E and waxy starches had a pasting temperature lower than that of the normal starches, indicating that all of these starches begin to build viscosity earlier than do the normal starches.

The waxy-E starches differed from the waxy starches in many respects (Table 9). All of the waxy-E starches had a peak time later than those of the waxy starches, indicating that the waxy-E starches develop viscosity more slowly than do waxy starches and also retain and continue to develop viscosity under more severe temperature conditions than do the waxy starches. Additionally, the waxy-E starches develop significantly higher setback viscosities and final viscosities than do waxy starches, attributable to the structure-developing amylose in the waxy-E starches.

Further, as in Examples 3 and 4, the waxy-E starches may be divided into two groups of differing behavior: one group containing EX56wx-E1, EX78wx-E1, and EX385wx-E1 (wx-E1 Group, based on functional properties, see Table 9) and the other group containing EX12wx-E2 (wx-E2 Group, also based on functional properties, see Table 9). Despite the common differences between all of these waxy-E starches and waxy starches noted above, the process by which each group obtains these properties happens in a different way. Starches of the wx-E1 Group develop a peak viscosity similar to that of the waxy starches, and then set back to result in a final viscosity higher than waxy starch. Starches of the wx-E2 Group plateau at a viscosity between the normal starches and waxy starches and then develop considerable setback viscosity to result in a final viscosity higher than waxy starches.

TABLE 9

Rapid Visco Analysis Profile Data - Ph 6.5–20 min @ 95° C.

| Sample | Peak Viscosity (cp) | HP Viscosity (cp) | Breakdown (cp) | B/P[a] (%) | Final Viscosity (cp) | Setback (cp) | Peak Time (min) | Pasting Temp (° C.) |
|---|---|---|---|---|---|---|---|---|
| Normal | | | | | | | | |
| EX68 | 483 ± 3 | 427 ± 3 | 76 ± 8 | 15.7 | 609 ± 39 | 202 ± 48 | 4.4 ± 0.0 | 95[b] |
| C* Normal wx starch | 409 ± 6 | 378 ± 6 | 89 ± 24 | 21.8 | 408 ± 50 | 88 ± 27 | 4.7 ± 0.1 | 95[b] |
| EX68wx | 1096 ± 22 | 531 ± 10 | 761 ± 17 | 69.4 | 509 ± 10 | 174 ± 5 | 2.9 ± 0.1 | 77.2 ± 0.4 |
| EX56wx | 1160 ± 27 | 561 ± 3 | 788 ± 19 | 67.9 | 532 ± 22 | 160 ± 17 | 3.0 ± 0.0 | 77.7 ± 0.3 |
| C* waxy waxy-E starch | 1212 ± 37 | 866 ± 42 | 709 ± 35 | 58.5 | 624 ± 18 | 122 ± 20 | 3.3 ± 0.0 | 78.7 ± 0.6 |
| EX56wx-E1 | 1205 ± 23 | 889 ± 31 | 747 ± 21 | 62.0 | 693 ± 27 | 235 ± 24 | 4.4 ± 0.1 | 77.2 ± 0.3 |
| EX78wx-E1 | 1171 ± 13 | 933 ± 6 | 668 ± 24 | 57.0 | 698 ± 13 | 196 ± 24 | 5.0 ± 0.1 | 79.7 ± 0.5 |
| EX385wx-E1 | 1194 ± 7 | 911 ± 15 | 684 ± 16 | 57.2 | 865 ± 32 | 355 ± 13 | 4.6 ± 0.0 | 78.6 ± 0.5 |
| EX12wx-E1 | 783 ± 12 | 786 ± 13 | 243 ± 4 | 31.0 | 755 ± 12 | 216 ± 8 | 6.9 ± 0.1 | 88.3 ± 4.1 |

[a]Percentage breakdown relative to the peak viscosity. B/P = {[Breakdown (cp)]/[Peak Viscosity (cp)]} × 100
[b]Pasting was observed at the highest temperature reached during the experiment, 95° C.

Example 6

Starch Gelatinization—Pasting Viscosity Profiles at pH 6.5—2.5 min at 95° C.—Mixtures of waxy and Normal Starch This experiment was conducted to demonstrate that the properties of waxy-E starches cannot be reproduced using mixtures of normal starch and waxy starch.

Mixtures of normal starch and waxy starch were prepared to produce starches with bulk amylose content within the range observed for the waxy-E starches. The starches examined were the waxy and normal starches of EX68 used in Example 4. The composition of the mixtures prepared and the amylose content of the mixtures is illustrated in Table 10. The amylose content of the normal starch was assumed to be 20% for this experiment.

TABLE 10

Composition of starch mixtures

| Estimated Amylose Content (%) | Normal Starch EX68 (dry mass %) | Waxy Starch EX68wx (dry mass %) |
|---|---|---|
| 0 | 0 | 100 |
| 2 | 10 | 90 |
| 4 | 20 | 80 |
| 6 | 30 | 70 |
| 8 | 40 | 60 |

The starch pastes were prepared using the RVA Standard Method. For this Example, 1.4 g of total starch on a dry weight basis was used for all tests. The properties of the mixtures are shown in Table 11.

Addition of the normal starch to the waxy starch had four clear effects on the bulk properties of the starch: (1) the peak viscosity decreased with increasing normal starch content, (2) the breakdown of the starch decreased with increasing normal starch content as indicated by both the absolute value of the breakdown and by the B/P ratio, (3) the setback viscosity of the starch increased with the inclusion of normal starch, and (4) the peak time of the starch increased with increasing starch content. Some of these behaviors appear to mimic those of the waxy-E starches, especially those of the wx-E1 Group (Example 4), however:

1 ) for the wx-E1 Group waxy-E starches higher peak viscosities are observed compared to the 80% EX68wx/20% EX68 mixture which shows a considerable drop in peak viscosity compared to the 100% EX68wx starch.

2) The wx-E1 Group waxy-E starches retain considerably more viscosity as a hot paste and at their minimum viscosities compared to the 80% EX68wx/20% EX68 mixture which has hot paste and minimum viscosities similar to or lower than those of the EX68wx starch. The decreasing B/P ratio for the mixtures of waxy and normal starch with increasing normal starch appears to be primarily due to the decreasing peak viscosities of the mixtures with increasing amylose normal starch content rather than a decrease in breakdown viscosity.

TABLE 11

Rapid Visco Analysis Profile Data - Ph 6.5

| Sample | Peak Viscosity (cp) | HP Viscosity (cp) | Breakdown (cp) | B/P[a] (%) | Final Viscosity (cp) | Setback (cp) | Peak Time (min) | Pasting Temp (° C.) |
|---|---|---|---|---|---|---|---|---|
| EX68wx | 1133 ± 3 | 616 ± 4 | 573 ± 14 | 50.6 | 633 ± 10 | 73 ± 7 | 4.1 ± 0.0 | 75.5 ± 0.5 |
| 90% EX68wx 2% amylose | 1065 | 585 | 533 | 50.0 | 631 | 99 | 4.2 | 75.9 |
| 80% EX68wx 4% amylose | 1029 | 619 | 472 | 45.9 | 677 | 120 | 4.3 | 76.0 |

TABLE 11-continued

Rapid Visco Analysis Profile Data - Ph 6.5

| Sample | Peak Viscosity (cp) | HP Viscosity (cp) | Breakdown (cp) | B/P[a] (%) | Final Viscosity (cp) | Setback (cp) | Peak Time (min) | Pasting Temp (° C.) |
|---|---|---|---|---|---|---|---|---|
| 70% EX68wx 6% amylose | 971 | 614 | 411 | 42.3 | 682 | 122 | 4.4 | 75.9 |
| 60% EX68wx 8% amylose | 903 | 628 | 333 | 36.9 | 675 | 105 | 4.8 | 75.9 |

[a]Percentage breakdown relative to the peak viscosity. B/P = {[Breakdown (cp)]/[Peak Viscosity (cp)]} × 100

3) The wx-E1 Group waxy-E starches have higher pasting temperatures and peak times than the mixtures of waxy and normal starch; these properties appear to be dominated by the waxy content of the mixtures.

All of these points indicate that the waxy-E starch properties cannot be reproduced by blending of normal starch with waxy starch.

Example 7

Starch Paste Texture—Rheology

This experiment was conducted to demonstrate the rheological properties of waxy-E starch.

Starch pastes were prepared with waxy starches (EX68wx, EX56wx, Cerestar-USA commercial waxy starch C*Gel 02430) and waxy-E starches (EX385wx-E1, EX78wx-E1, EX56wx-E1, and EX12wx-E1). Normal starches gelled during storage in preliminary experiments, an indication of their instability and high elastic modulus, so they could not tested rheologically.

Starches were cooked using the RVA Standard Method. For this Example, 1.4 g of starch on a dry weight basis was used for all tests.

Immediately after cooking, each paste was transferred to a 50 mL tube and placed in a 25° C. water bath. Samples were analyzed using a rheometer 18–22 hours later. After storage, frequency and strain dependence of the starch pastes were tested using a rheometer (RFSIII Fluids Spectrometer, Rheometric Scientific, Piscataway N.J.). All pastes were measured at 25° C. A parallel plate geometry was utilized for testing (50 mm; 0.9 to 1.1 mm gap width); loaded samples were permitted to rest between the plates of the rheometer for 10 minutes in order to reduce the effects of loading on the measurements. A thin film of oil was applied to the exposed surface of the paste between the rheometer plates to minimize moisture evaporation during the testing process. Frequency dependence of a paste was always examined first, followed by the strain dependence. The frequency dependence of the pastes was tested between 0.1 and 100 radians per second with a oscillatory strain of 1%. Strain dependence of the pastes was tested between 0.1 and 1000% deformation at a constant testing frequency of 1 radian per second. The EM of a starch is the elastic modulus of the starch below the yield strain and at an oscillatory frequency of 1 rad/sec as observed using this testing method after the starch has been cooked using the RVA Standard Method using a concentration of starch such that the final viscosity of a waxy starch extracted from a plant of the same species is between 600 and 850 centipoise and after the cooked starch has been stored for 18–22 hours at 25° C.

Figure 6:
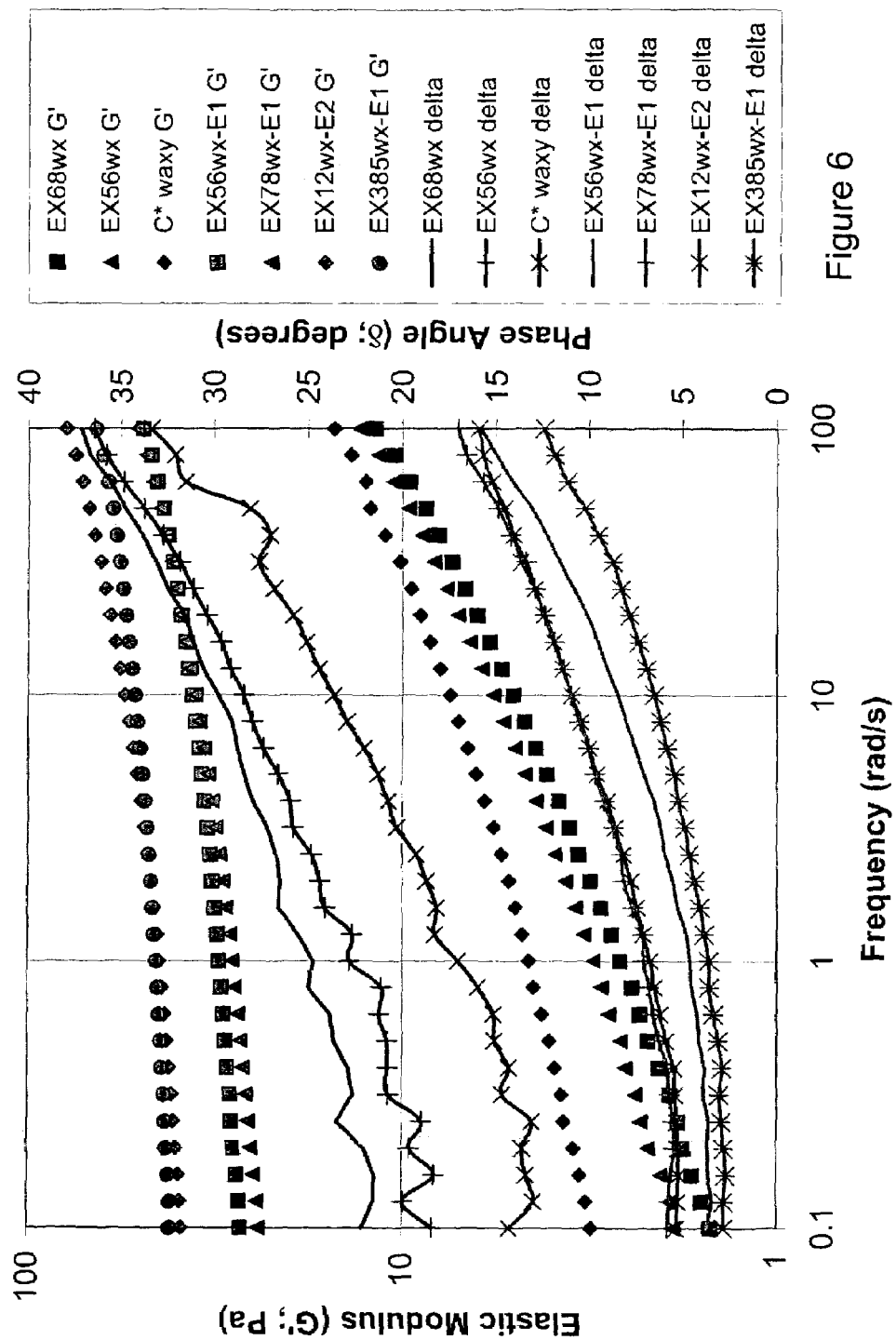
FIG. 6. Frequency dependence (rad/s) at 1% strain of 5% starch pastes prepared in a pH 6.5 buffer using the RVA programmed with a 2.5 min cooking step at 95° C. Elastic modulus and phase angle are plotted against frequency.
Figure 7:
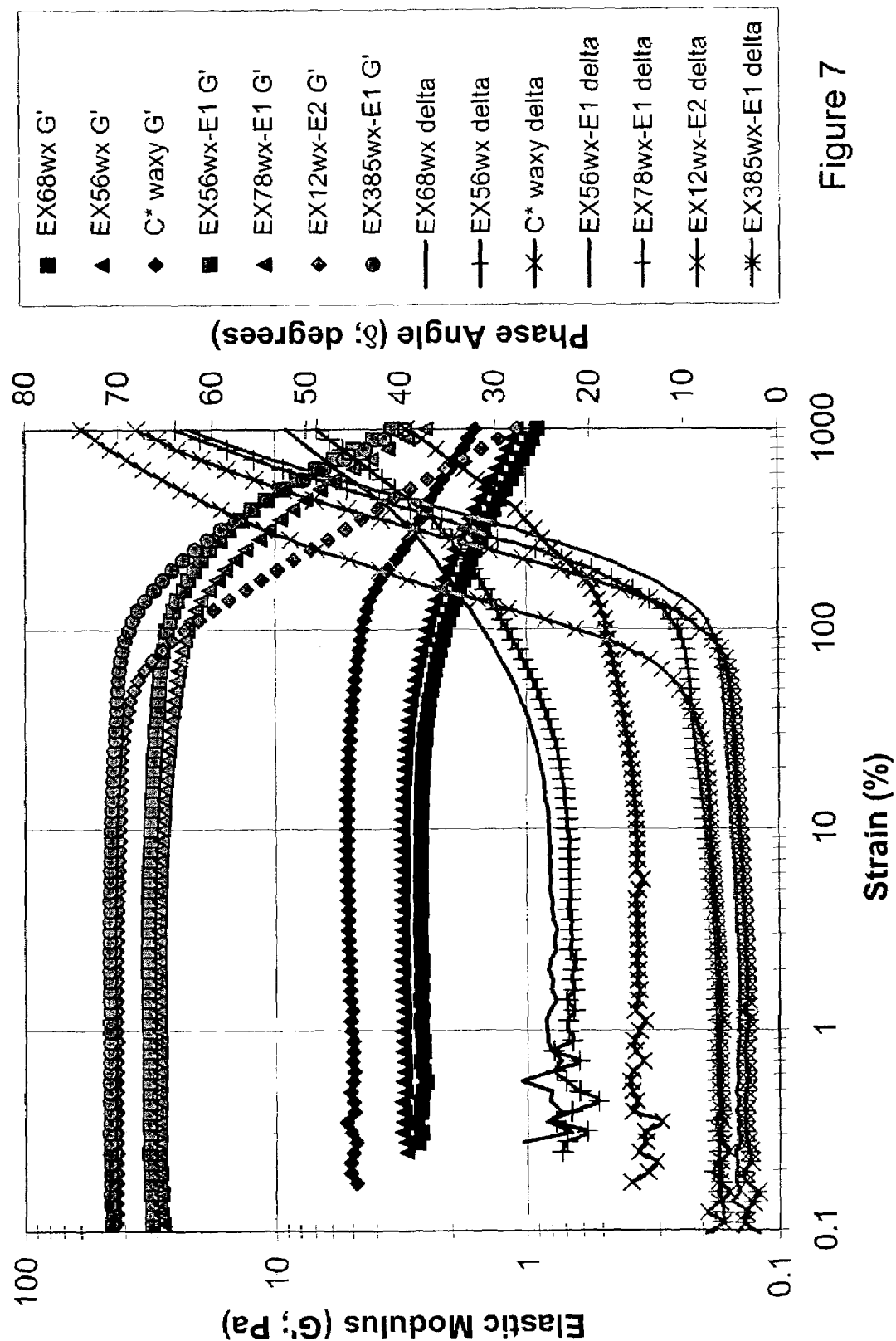
FIG. 7. Strain dependence at 1 rad/s frequency of 5% starch pastes prepared in a pH 6.5 buffer using the RVA programmed with a 2.5 min cooking step at 95° C. Elastic modululs and phase angle are plotted against strain (%).

Two replicates of the experiment were conducted, and the analysis order of the second replicate was the reverse of the first replicate in an attempt to eliminate any confounding effect of storage time on the results. The strain and frequency dependence of the starch pastes is presented in Table 12. The results of each replicate are shown. Illustrative charts of G' and phase angle vs frequency and G' and phase angle vs strain are presented in FIGS. 6 and 7, respectively. The waxy-E starch pastes had a lower frequency dependence than did any of the waxy starch pastes (Table 12), with approximately a 2 fold increase in G' between a frequency of 0.1 and 100 radians per second compared to waxy starch pastes which generally had a 5 fold increase over the same frequency range. The lower frequency dependence of waxy-E starch pastes shows that the waxy-E starch pastes have more gel-like character than do waxy starch pastes.

TABLE 12

Rheology of Starch Pastes - Storage at 25° C.

| | Frequency Dependence | | | | Strain Dependence | | | | | |
|---|---|---|---|---|---|---|---|---|---|---|
| | 0.1 rad/s | | 100 rad/s | | 1% | | 200% | | 1000% | |
| Starch Source | G' (Pa) | phase angle (deg) | G' (Pa) | phase angle (deg) | G' (Pa) | phase angle (degrees) | G' (Pa) | phase angle (degrees) | G' (Pa) | phase angle (degrees) |
| wx starch | | | | | | | | | | |
| EX68wx | 2 | 22 | 12 | 37 | 3 | 25 | 2 | 36 | 1 | 52 |
| | 2 | 18 | 13 | 37 | 3 | 24 | 2 | 37 | 1 | 50 |
| EX56wx | 2 | 19 | 13 | 36 | 3 | 22 | 2 | 32 | 1 | 49 |
| | 2 | 17 | 13 | 36 | 3 | 23 | 2 | 36 | 1 | 50 |
| C* waxy | 3 | 14 | 15 | 33 | 5 | 15 | 3 | 22 | 2 | 39 |

TABLE 12-continued

Rheology of Starch Pastes - Storage at 25° C.

| | Frequency Dependence | | | | Strain Dependence | | | | |
|---|---|---|---|---|---|---|---|---|---|
| | 0.1 rad/s | | 100 rad/s | | 1% | | 200% | | 1000% |
| Starch Source | G' (Pa) | phase angle (deg) | G' (Pa) | phase angle (deg) | G' (Pa) | phase angle (degrees) | G' (Pa) | phase angle (degrees) | G' (Pa) | phase angle (degrees) |
| waxy-E starch | 3 | 12 | 16 | 33 | 5 | 17 | 3 | 24 | 2 | 40 |
| EX56wx-E1 | 27 | 4 | 49 | 16 | 32 | 4 | 21 | 16 | 3 | 63 |
| | 26 | 4 | 46 | 17 | 29 | 5 | 21 | 16 | 4 | 63 |
| EX385wx-E1 | 41 | 3 | 66 | 12 | 46 | 3 | 26 | 23 | 3 | 68 |
| | 41 | 3 | 65 | 13 | 44 | 4 | 26 | 24 | 3 | 69 |
| EX78wx-E1 | 24 | 6 | 51 | 17 | 29 | 6 | 16 | 20 | 2 | 64 |
| | 22 | 6 | 49 | 18 | 26 | 7 | 17 | 19 | 3 | 64 |
| EX12wx-E2 | 39 | 5 | 79 | 16 | 43 | 6 | 10 | 42 | 1 | 74 |
| | 40 | 5 | 81 | 16 | 46 | 6 | 11 | 41 | 1 | 74 |

The waxy-E starch pastes had a higher elastic modulus at 1% strain than the elastic modulus of waxy starch pastes, exceeding nearly 10 fold in all cases. Additionally, the phase angles of waxy-E starch pastes at 1% strain were lower compared with the phase angles of waxy starch pastes, indicating that a higher proportion of the complex modulus of waxy-E starch pastes is attributable to the elastic component of the paste compared to waxy starch pastes. Thus, the waxy-E starch pastes are considerably different rheologically from waxy starch pastes.

The elastic modulus of waxy-E starch pastes remained higher than the elastic modulus of waxy starch pastes through 500–1000% strain. Additionally, through 100–200% strain waxy-E starch pastes generally maintained lower phase angles than waxy starch pastes. Thus, waxy-E starch pastes not only retained a relatively high elastic modulus but also a relatively high elasticity (as a component of the complex modulus, indicated by the low phase angles) through high deformations compared to waxy starch pastes.

This combination of a moderate elastic modulus and low phase angle indicates that under low deformations the waxy-E starches behave more like gels than viscous pastes through 1% to 200% strain. Further, the waxy-E starches may be divided into two groups (wx-E1 and wx-E2) as in the previous examples, with the starch of the wx-E2 group yielding at a lower strain than the wx-E1 starches. Regarding all of the waxy-E starches, their gel behavior is unusual for a native starch: waxy starches, as Table 12 shows, do not develop a high elastic modulus and have a high phase angle even at low strains, and gels of normal starch or amylose are sensitive to small deformations (see additionally Example 8), often losing considerable elastic modulus between 0.1% and 1% strain like other strong biopolymer gels.

Example 8

Starch Paste Texture—Penetrometry

This experiment was conducted to demonstrate that waxy-E starches have the ability to develop gels, unlike waxy starches at the same concentration, and that the gels of waxy-E starches do not have the same properties as normal starch gels. Penetrometry is conducted using a method modified from Takahashi and Seib (1988, Cereal Chemistry 65:474–483) and Yamin et al (1999, Cereal Chemistry 76:175–181). Well in advance of the experiment, a cylindrical plastic sample receptacle (58 mm tall by 22 mm inside diameter) with a screw-on lid is prepared by sawing it along its long axis. The receptacle halves are welded together with silicone adhesive, taking care to match the threads for the screw-on lid at the open end of the receptacle. The adhesive holding the welded receptacle together is then permitted to dry for 48 hours. Starch is pasted as a 10% (w/w) slurry in pH 6.5 phosphate buffer in the Rapid Visco Analyzer (Rapid Visco Analyser 4, Newport Scientific Pty. Ltd.): while stirring at 160 rpm, the sample is held at 50° C. for 1 min, heated to 95° C. over 3.7 min, held at 95° C. for 2.5 min, cooled to 50° C. over 3.8 min, and then held at 50° C. for 2 min. Upon immediate completeion of sample preparation using the RVA, the sample receptacle is filled by the resultant gelatinized paste from the RVA. The full receptacle is then covered with its screw-on cap and then the cap and a portion of the sample receptacle is wrapped with laboratory film. The gelatinized starch paste is stored for seven days at 4° C. Before analysis, a starch sample is removed from refrigerated storage, and allowed to equilibrate to room temperature for 2 hours. For analysis, the halves of the sample receptacle are separated and the gel (when present) is cut along its short axis into two pieces: doing so provides two samples for analysis with no edge effects due to the sample being in contact with either the bottom or top of the sample receptacle. These "contact" edges are trimmed as necessary to provide a horizontal surface for gel testing. The prepared gels are analyzed using a penetrometer (Texture Analyzer TA-XT2i with a 5 kg load cell, Stable Micro Systems, England) interfaced with a computer running associated data analysis and instrument control software (Texture Expert Exceed version 2.55, Stable Micro Systems, England). Analysis was done using a method modified from Yamin et al (1999, Cereal Chemistry 76:175–181). A gel sample 1.5 cm in height is penetrated with a cylindrical probe with a flat surface having a diameter of 4 mm. The gel is compressed 7.5 mm at a rate of 0.9 mm/s by the probe and withdrawn at the same rate. The peak force observed during penetration of the gel was the hardness. The fracturability was the initial force peak observed during penetration of the sample, related to the initial penetration of the sample by the downward-moving probe. The force during penetration as the area of the curve (in gram-seconds) was the gel firmness. The positive force as the area of the curve (in gram-seconds) acting on the probe during its withdrawl was recorded. The resiliency (or resiliency) of the gel was calculated as the ratio of the positive force during probe withdrawl to the positive force during probe penetration (the firmness). Ten measurements per gel were conducted and the two highest and two lowest measurements of each property were removed; these data were typically beyond two standard deviations of the mean. Penetrometry data, as the average of six penetrations per gel, are presented in Table 13. The experiment was conducted in duplicate; results from both gels prepared for each starch are presented in Table 13.

The results of these tests clearly show that waxy-E starches can develop a range of textures which is not developed by either waxy-E or normal starch. All of the waxy-E starches have a hardness and firmness below that of normal starches. Additionally, the quality of waxy-E starch gels is not similar to those formed by normal starch: waxy-E starch gels do not fracture as do normal starch gels. Instead, the waxy-E gels which are formed are highly resilient and deformable with a gradual increase in force during penetration and a gradual release of that force during removal of the probe from the starch gel. This behavior is consistent with the high deformability of waxy-E starch pastes observed using dynamic oscillatory rheometry (Example 7).

TABLE 13

Starch Gel Texture Properties

| Sample | Fracturability | Hardness (g) | Firmness (g-s) | Probe Withdrawl Positive Area (g-s) | Resilience (%) |
|---|---|---|---|---|---|
| Normal |  |  |  |  |  |
| EX68 | 30 ± 1 | V[a] | 145 ± 9 | 17 ± 3 | 12 |
|  | 31 ± 1 | V | 177 ± 4 | 19 ± 1 | 11 |
| C* Normal | 35 ± 1 | V | 191 ± 3 | 25 ± 2 | 13 |
| wx starch | 34 ± 2 | V | 213 ± 6 | 21 ± 3 | 10 |
| EX68wx | NA[b] | NA | NA | NA | NA |
|  | NA | NA | NA | NA | NA |
| C* waxy | NA | NA | NA | NA | NA |
|  | NA | NA | NA | NA | NA |
| waxy-E starch |  |  |  |  |  |
| EX56wx-E1 | ND[c] | 2.3 ± 0.2 | 5.4 ± 0.6 | 4.4 ± 0.6 | 81 |
|  | ND | 2.9 ± 0.2 | 8 ± 1 | 6.4 ± 0.9 | 80 |
| EX78wx-E1 | ND | 5.4 ± 0.2 | 14.0 ± 0.9 | 11.3 ± 0.8 | 80 |
|  | ND | 6.7 ± 1.1 | 20 ± 3.8 | 12.2 ± 0.9 | 61 |
| EX385wx-E1 | ND | 6.6 ± 0.7 | 21 ± 3 | 16 ± 2 | 76 |
|  | ND | 6.0 ± 0.3 | 18 ± 2 | 15 ± 1 | 83 |
| EX12wx-E2 | ND | 4.6 ± 0.4 | 13 ± 2 | 8.1 ± 0.9 | 62 |
|  | ND | 4.0 ± 0.3 | 11 ± 2 | 6.8 ± 0.7 | 62 |

[a]V = variable. Hardness varied considerably after the initial fracture of the gel for these samples. Results are not reported but were generally of the same magnitude as the hardness.
[b]NA = not applicable. Starch was a viscous sol which could not be measured.
[c]ND = not detected. No initial fracture point was observed for these gels. Instead, the force continued to steadily increase until the maximum penetration depth was reached.

Example 9

Starch Gelatinization—Calorimetry

This experiment was conducted to illustrate the temperature range and granule stability of waxy-E starches. As described earlier, assessment of the gelatinization temperature profile of the starch is commonly conducted using a differential scanning calorimeter (DSC).

For each starch, 8.0 mg (±0.2 mg) of starch (dry weight basis) is weighed into a 0.05 mL stainless steel DSC sample pan. The sample is then brought to a total mass of approximately 30 mg with water, resulting in a suspension of 25% starch (w/w). The mass of starch and water is recorded and the starch concentration calculated based on the mass of water added and the solids content of the starch. The pan is then sealed and stored at room temperature for approximately 18 h. The sample is heated in the DSC (Pyris 1 Differenetial Scanning Calorimeter, PerkinElmer Instruments, Norwalk, Conn.) from 5° C. to 140° C. at 10° C./min. The onset temperature, peak temperature, endset temperature, and enthalpy of the gelatinization and amylose-lipid complex (if observed) endotherms are calculated using the controlling/analysis software (Pyris Software v. 3.81, PerkinElmer Instruments). Amylose-lipid complex enthalpy is determined as a partial area of the total endotherm after 85° C. for wild type starch when overlap is observed between the starch gelatinization and amylose-lipid complex dissociation endotherms when necessary. An empty stainless steel pan is used as a reference and temperature and enthalpy calibrations are made using an indium standard. Gelatinization data as averages of at least three replicates are presented in Table 14.

TABLE 14

Starch Gelatinization Temperatures and Enthalpy

| Sample | Onset Temp (° C.) | Peak Temp (° C.) | Endset Temp (° C.) | Enthalpy (J/g) |
|---|---|---|---|---|
| Normal EX68 |  |  |  |  |
| Starch-Starch | 68.4 ± 0.2 | 71.9 ± 0.1 | 76.7 ± 0.2 | 16.8 ± 0.5 |
| AM-Lipid | NA* | NA* | NA* | 2.9 ± 0.5 |
| C* Normal |  |  |  |  |
| Starch-Starch | 69.8 ± 0.3 | 73.1 ± 0.2 | 77.9 ± 0.2 | 17.3 ± 0.4 |
| AM-Lipid | 83.9 ± 1.6 | 98.8 ± 2.9 | 107.4 ± 0.6 | 2.2 ± 0.3 |
| wx starch |  |  |  |  |
| EX68wx | 67.8 ± 0.1 | 74.0 ± 0.3 | 79.3 ± 0.2 | 18.7 ± 0.4 |
| EX56wx | 67.4 ± 0.0 | 71.0 ± 0.0 | 76.1 ± 0.1 | 17.8 ± 0.5 |
| C* waxy wxae starch | 66.8 ± 0.3 | 74.0 ± 0.1 | 79.5 ± 0.3 | 18.8 ± 0.4 |
| EX52wxae waxy-E starch | 75.1 ± 0.4 | 85.7 ± 0.4 | 95.0 ± 0.6 | 23.5 ± 0.4 |
| EX56wx-E1 | 67.5 ± 0.4 | 70.9 ± 0.2 | 76.3 ± 0.5 | 18.8 ± 0.8 |
| EX385wx-E1 | 66.1 ± 0.1 | 72.1 ± 0.3 | 79.1 ± 0.1 | 18.3 ± 0.8 |
| EX78wx-E1 | 68.8 ± 0.1 | 74.3 ± 0.1 | 79.5 ± 0.4 | 18.6 ± 0.3 |
| EX12wx-E2 |  |  |  |  |
| Starch-Starch | 70.3 ± 0.2 | 74.3 ± 0.3 | 80.5 ± 0.1 | 19.5 ± 0.7 |
| AM-Lipid | 87.8 ± 2.0 | 101.0 ± 0.2 | 107.1 ± 1.5 | 1.1 ± 0.2 |

*NA = Not Applicable. Enthalpy was determined as a partial area of the total. Onset Temp, Peak Temp, and Endset Temp were not observed for this endotherm.

The results of these tests clearly show that the waxy-E starches are similar in both gelatinization temperature range and enthalpy to waxy starches and normal starch. For at least one waxy-E starch, sufficient amylose-lipid complex enthalpy is also present for detection during gelatinization using DSC. The lower amylose-lipid complex enthalpy observed for waxy-E starches compared to normal starches is consistent with the lower amylose content of waxy-E starches.

Example 10

Starch Stability—Calorimetry

This experiment was conducted to illustrate the paste stability of waxy-E starches. As described above, starch can reorganize after gelatinization. The process of reorganization is called retrogradation. The amount of reorganization, an assessment of the temperature stability of starch, is commonly conducted using a differential scanning calorimeter (DSC).

Samples examined for their gelatinization properties in the previous example (above) were cooled to 5° C. and immediately placed in a refrigerator, where they were stored for 7 days. After storage, the samples were removed from the refrigerator, immediately placed in the DSC chamber at 5° C., and reheated in the DSC (Pyris 1 Differenetial Scanning Calorimeter, PerkinElmer Instruments, Norwalk, Conn.) from 5° C. to 140° C. at 10° C./min. The onset temperature, peak temperature, endpoint temperature, and enthalpy of the retrogradation endotherm(s) are calculated using the controlling/analysis software (Pyris Software v. 3.81, PerkinElmer Instruments). An empty pan was used as a reference and temperature and enthalpy calibrations were made using an indium standard. This method was used to determine the Retrogradation Enthalpy of the starch. Retrogradation data are presented in Table 15.

TABLE 15

Starch Retrogradation Temperatures and Enthalpy

| Sample | Onset Temp (° C.) | Peak Temp (° C.) | Endset Temp (° C.) | Enthalpy (J/g) |
| --- | --- | --- | --- | --- |
| Normal EX68 | | | | |
| Starch-Starch | 35.6 ± 0.1 | 51.9 ± 0.6 | 65.1 ± 0.2 | 7.8 ± 0.2 |
| AM-Lipid | 87.9 ± 0.8 | 97.5 ± 0.4 | 105.2 ± 0.8 | 1.6 ± 0.4 |
| C* Normal | | | | |
| Starch-Starch | 34.8 ± 0.9 | 51.3 ± 0.9 | 65.3 ± 0.8 | 8.6 ± 0.2 |
| AM-Lipid | 87.7 ± 0.4 | 96.5 ± 0.6 | 105.6 ± 2.7 | 1.4 ± 0.1 |
| wx starch | | | | |
| EX68wx | 40 ± 6 | 54.2 ± 2.1 | 66.3 ± 0.3 | 2.9 ± 0.3 |
| C* waxy | 35.2 ± 1.0 | 57.0 ± 1.4 | 68.1 ± 4.9 | 2.8 ± 0.4 |
| wxae starch | | | | |
| EX52wxae | 36.2 ± 0.4 | 70.8 ± 0.5 | 84.5 ± 0.5 | 13.9 ± 0.6 |
| waxy-E starch | | | | |
| EX56wx-E1 | 34.4 ± 0.6 | 54.9 ± 0.5 | 64.8 ± 0.4 | 4.3 ± 0.4 |
| EX385wx-E1 | 34.2 ± 0.4 | 55.8 ± 0.6 | 65.8 ± 0.5 | 5.4 ± 0.6 |
| EX78wx-E1 | | | | |
| Starch-Starch | 34.8 ± 1.3 | 54.2 ± 1.0 | 65.5 ± 0.8 | 6.7 ± 0.7 |
| AM-Lipid | 93 ± 5.0 | 98 ± 2 | 108 ± 3 | 0.31 ± 0.07 |

TABLE 15-continued

Starch Retrogradation Temperatures and Enthalpy

| Sample | Onset Temp (° C.) | Peak Temp (° C.) | Endset Temp (° C.) | Enthalpy (J/g) |
| --- | --- | --- | --- | --- |
| EX12wx-E2 | | | | |
| Starch-Starch | 34.9 ± 1.1 | 53.2 ± 0.9 | 65.0 ± 0.6 | 7.8 ± 0.8 |
| AM-Lipid | 90 ± 3 | 94.4 ± 0.2 | 106 ± 2 | 1.0 ± 0.2 |

*NA = Not Applicable.
The endotherm for this starch was bimodal, resulting in unreliable estimates of the onset temperature.

The waxy-E starches are between waxy starches and normal starches in their retrogradation enthalpy, indicating that the waxy-E starches have intermediate low temperature stability. All of the waxy-E starches have a retrogradation enthalpy lower than or equivalent to normal starches. For at least two waxy-E starches, sufficient amylose-lipid complex enthalpy is also present for detection during retrogradation analysis using DSC. The lower amylose-lipid complex enthalpy observed for waxy-E starches compared to normal starches is consistent with the lower amylose content of waxy-E starches.

Example 11

Starch Structure—High-Performance Anion-Exchange Chromatography

Figure 8:
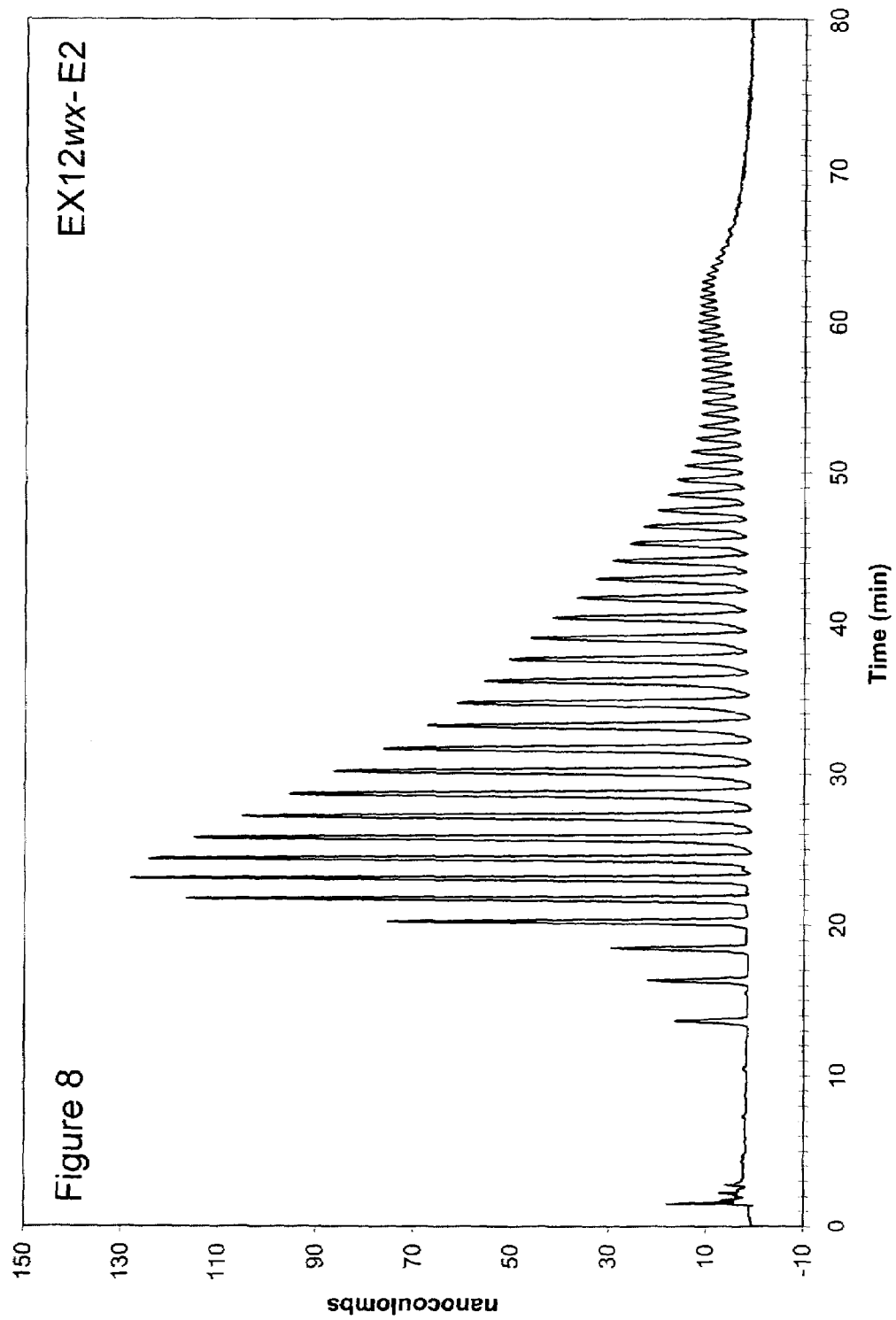
FIG. 8. A high-performance anion exchange chromatogram of isoamylose-debranched EX12wx-E2 starch. Detector response in nanocoulombs is plotted against time.
Figure 9:
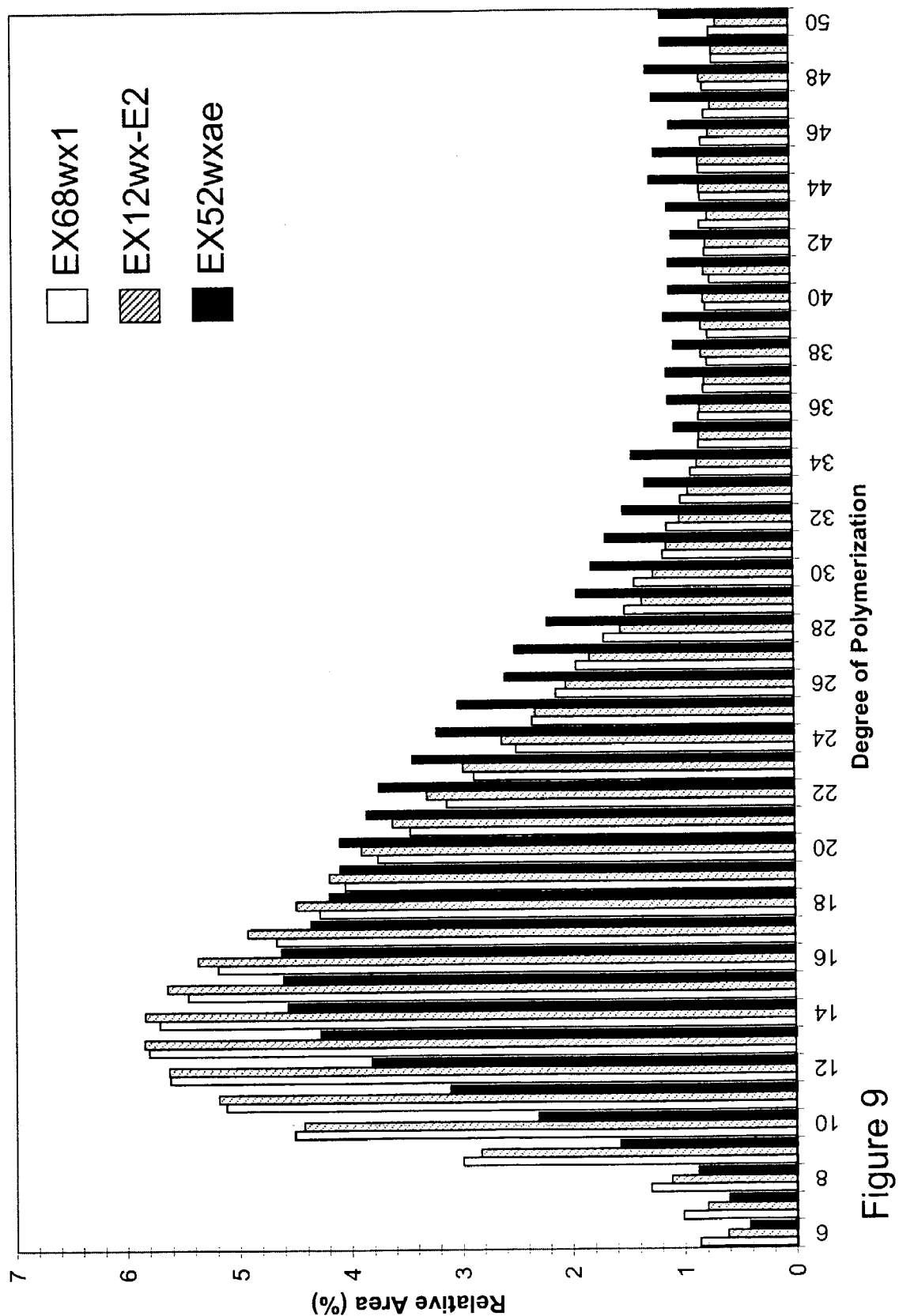
FIG. 9. A comparison of the relative chain length distribution of EX68 waxy starch, EX12wx-E2 starch and EX52 waxy amylose-extender double mutant starch. Relative percent area is plotted against the degree of polymerization.

This test was conducted to illustrate the short chain distribution of waxy-E starches. Starch granules (5.5 mg) in a microcentrifuge tube are dispersed in 0.4 mL of 90% dimethyl sulfoxide by heating in a boiling water bath for 1 h. Samples consisted of two independent events of waxy starch from the EX68 line (EX68wx1 and EX68wx2), a wxae starch (EX52wxae), and four waxy-E starches (EX56wx-E1, EX385wx-E1, EX78wx-E1, and EX12wx-E1). The sample is agitated every 10 min during heating. The dispersed starch is precipitated by adding 1.6 mL of ethanol and centrifuged at 3000×g for 5 min in a microcentrifuge at room temperature. The supernatant material is discarded. The starch pellet is washed twice with 1.0 mL of ethanol and once with 1.0 mL of acetone, centrifuging the sample as described above each time. The resultant non-granular starch is allowed to dry in the uncapped microcentrifuge tube for at least 2 h. The dry non-granular starch is mixed with 0.9 mL of water and 0.1 mL of 100 mM sodium acetate (pH 4.5) and heated in a boiling water bath for 1 hour. The sample is mixed every 10 min during boiling. After heating, the sample is cooled to 40° C. in a water bath. An isoamylose suspension (0.001 mL; isolated from Pseudomonas sp., Megazyme International Ireland Ltd, Co. Wicklow, Ireland) is added and the sample is inverted several times before it is returned to the 40° C. water bath. After 18 h, the sample is heated in a boiling water bath for 5 min to inactivate the enzyme. The sample is allowed to cool before 0.4 mL are centrifuged through a 0.22 micron filter. This filtered sample is immediately injected into the HPAEC system. HPAEC is conducted in conjunction with a pulsed amperometric detector (PAD) as part of a chromatography system (Dionex DX 500 chromatography system with a GP40 Gradient Pump, an ED40 Electrochemical Detector, and a Rheodyne model 9125 injector with a 0.050 mL injection loop, Dionex Corp, Sunnyvale, Calif.). A Carbopac PA1 (4×250 mm) analytical column (Dionex Corp, Sunnyvale, Calif.) with a Carbopac PA1 (4×50 mm) guard column (Dionex Corp, Sunnyvale, Calif.) is used to separate the component chains of the starch. The system is operated at a flow rate of 1.0 mL/min with a gradient profile of 150 mM sodium hydroxide (mobile phase "A") and 500 mM sodium acetate in 150 mM sodium hydroxide (mobile phase "B") as follows: 0 min, A:B::80:20; 2 min, A:B::80:20; 10 min, A:B::70:30; 20 min, A:B::50:50; 60 min, A:B::20:80; 80 min, A:B::20:80. All gradients in the profile are linear. The system is calibrated with of a mixture of glucose and oligosaccharides with a degree of polymerization (DP) between 2 and 7. Peaks appearing after DP 7 in the debranched starch chromatograms are presumed to have a DP a single glucose unit longer than the previously eluting peak. All injections are 0.050 mL. Monitoring of the chromatograms and analysis of the data is done using the accompanying software (Peaknet v. 4.30). None of the starches contained chains with a DP less than 6. A chromatogram of EX12wx-E2 is shown in FIG. 8. The percentage that each peak represents in relation to the total peak area through a DP of 50 is calcualted. These percentages are presented in Table 16. Relative area percentage plots of EX68wx1, EX12wx-E2, and EX52wxae are illustrated in FIG. 9.

TABLE 16

Area Percentages of Debranched Non-Granular Starch through DP

| DP | EX68 wx1 | EX68 wx2 | EX52 wxae | EX56 wx-E1 | EX385 wx-E1 | EX78 wx-E1 | EX12 wx-E2 |
|---|---|---|---|---|---|---|---|
| 6 | 0.621 | 0.805 | 0.432 | 0.718 | 0.760 | 0.862 | 0.621 |
| 7 | 0.801 | 1.054 | 0.609 | 0.989 | 0.991 | 1.055 | 0.801 |
| 8 | 1.121 | 1.313 | 0.881 | 1.260 | 1.422 | 1.342 | 1.121 |
| 9 | 2.834 | 2.830 | 1.576 | 3.016 | 2.885 | 2.992 | 2.834 |
| 10 | 4.426 | 4.142 | 2.310 | 4.600 | 4.135 | 4.594 | 4.426 |
| 11 | 5.186 | 4.768 | 3.108 | 5.198 | 4.675 | 5.120 | 5.186 |
| 12 | 5.630 | 5.132 | 3.815 | 5.625 | 5.104 | 5.602 | 5.630 |
| 13 | 5.845 | 5.402 | 4.272 | 5.826 | 5.261 | 5.747 | 5.845 |
| 14 | 5.837 | 5.434 | 4.563 | 5.832 | 5.351 | 5.671 | 5.837 |
| 15 | 5.642 | 5.251 | 4.605 | 5.654 | 5.254 | 5.525 | 5.642 |
| 16 | 5.369 | 4.975 | 4.622 | 5.396 | 4.957 | 5.275 | 5.369 |
| 17 | 4.923 | 4.457 | 4.361 | 4.880 | 4.591 | 4.862 | 4.923 |
| 18 | 4.488 | 4.095 | 4.188 | 4.453 | 4.201 | 4.420 | 4.488 |
| 19 | 4.188 | 3.990 | 4.091 | 4.137 | 3.977 | 4.139 | 4.188 |
| 20 | 3.898 | 3.787 | 4.095 | 3.914 | 3.722 | 3.856 | 3.898 |
| 21 | 3.620 | 3.545 | 3.850 | 3.554 | 3.508 | 3.463 | 3.620 |
| 22 | 3.304 | 3.286 | 3.744 | 3.263 | 3.256 | 3.194 | 3.304 |
| 23 | 2.983 | 2.994 | 3.437 | 3.069 | 2.977 | 2.690 | 2.983 |
| 24 | 2.628 | 2.671 | 3.219 | 2.290 | 2.718 | 2.277 | 2.628 |
| 25 | 2.322 | 2.467 | 3.029 | 2.094 | 2.469 | 2.139 | 2.322 |
| 26 | 2.043 | 2.277 | 2.598 | 1.901 | 2.248 | 1.975 | 2.043 |
| 27 | 1.828 | 2.051 | 2.507 | 1.669 | 2.032 | 1.682 | 1.828 |
| 28 | 1.548 | 1.845 | 2.208 | 1.479 | 1.825 | 1.552 | 1.548 |
| 29 | 1.359 | 1.647 | 1.940 | 1.370 | 1.654 | 1.440 | 1.359 |
| 30 | 1.252 | 1.529 | 1.810 | 1.202 | 1.481 | 1.154 | 1.252 |
| 31 | 1.133 | 1.335 | 1.678 | 1.115 | 1.343 | 1.038 | 1.133 |
| 32 | 1.014 | 1.246 | 1.518 | 0.928 | 1.234 | 0.974 | 1.014 |
| 33 | 0.935 | 1.174 | 1.321 | 1.009 | 1.155 | 0.986 | 0.935 |
| 34 | 0.853 | 1.005 | 1.433 | 0.905 | 1.059 | 0.930 | 0.853 |
| 35 | 0.830 | 0.974 | 1.056 | 0.819 | 1.015 | 0.895 | 0.830 |
| 36 | 0.822 | 0.966 | 1.109 | 0.794 | 0.888 | 0.819 | 0.822 |
| 37 | 0.781 | 0.908 | 1.116 | 0.813 | 0.909 | 0.929 | 0.781 |
| 38 | 0.809 | 0.915 | 1.052 | 0.787 | 0.816 | 0.899 | 0.809 |
| 39 | 0.809 | 0.903 | 1.135 | 0.829 | 0.879 | 0.788 | 0.809 |
| 40 | 0.786 | 0.855 | 1.092 | 0.768 | 0.878 | 0.854 | 0.786 |
| 41 | 0.780 | 0.869 | 1.096 | 0.846 | 0.858 | 0.842 | 0.780 |
| 42 | 0.763 | 0.813 | 1.067 | 0.764 | 0.910 | 0.940 | 0.763 |
| 43 | 0.745 | 0.864 | 1.098 | 0.846 | 0.852 | 0.912 | 0.745 |
| 44 | 0.817 | 0.780 | 1.258 | 0.871 | 0.857 | 0.904 | 0.817 |
| 45 | 0.822 | 0.902 | 1.214 | 0.846 | 0.861 | 0.745 | 0.822 |
| 46 | 0.732 | 0.716 | 1.081 | 0.789 | 0.854 | 0.922 | 0.732 |

TABLE 16-continued

Area Percentages of Debranched Non-Granular Starch through DP

| DP | EX68 wx1 | EX68 wx2 | EX52 wxae | EX56 wx-E1 | EX385 wx-E1 | EX78 wx-E1 | EX12 wx-E2 |
|---|---|---|---|---|---|---|---|
| 47 | 0.712 | 0.789 | 1.226 | 0.751 | 0.822 | 0.791 | 0.712 |
| 48 | 0.810 | 0.755 | 1.284 | 0.783 | 0.790 | 0.753 | 0.810 |
| 49 | 0.697 | 0.735 | 1.146 | 0.752 | 0.804 | 0.784 | 0.697 |
| 50 | 0.656 | 0.747 | 1.148 | 0.597 | 0.763 | 0.666 | 0.656 |
| SUM | 100 | 100 | 100 | 100 | 100 | 100 | 100 |

As a proportion of the chains with a DP of 50 or less, the chain distribution of each waxy-E starch is not representative of the range observed for wxae (EX52wxae) starch. Instead, the chain distributions of the waxy-E starches are representative of the chain distributions observed for the waxy starch. If long amylopectin chains were the cause of the cooking and physical properties and amylose content of the starch illustrated in Examples 3, 4, 5, 7, and 8, the chain distribution would be expected to more closely resemble that of the wxae starch. This chromatographic analysis is consistent with the appearance of the high-performance size-exclusion chromatograms (FIG. 3) used to calculate the amylose content of the starches (Example 3).

Example 12

Determination of the Presence and Activity of Starch Biosynthetic Enzymes within Kernels This set of experiments was conducted to demonstrate that the waxy-E starch contains an active granule-bound starch synthase (GBSS) with reduced activity compared to normal starch and that commercial waxy starches and lab-isolated waxy starches lack such activity.

Starch Extraction and Protein Analysis of Starch Granules

The dry weight of a known number (1–5 kernels) from each sample was recorded and the kernels were ground initially using a retail coffee bean grinder. This was followed by homogenization using a Pro400 homogenizer (Pro-Scientific Inc., Monroe, Conn., USA) in TEB (Tissue extraction buffer; 50 mM MES (pH 7.5), 1 mM EDTA, 5 mM DTT) at 4° C. The resulting slurry was filtered through 4 to 6 layers of cheese-cloth and centrifuged at 10,000 rpm for 10 min. at 4° C. Supernates were saved and the pellets were washed 2×with TEB followed by a wash with 2% sodium dodecyl sulphate (SDS) solution. The pellet was again suspended in TEB and microfuged at 10,000 rpm at 4° C. The supernate from this wash was discarded and the pellets were stored at −80° C. until further used. Granular associated proteins were recovered by boiling starch for 10 min in the presence of SDS-sample loading buffer (57 mM pH 6.8 Tris-HCl, 2% SDS, 9% Glycerol, and a reducing agent plus bromophenol blue). The resulting slurry was cooled to room temperature and microfuged at 10,000 rpm for 10 min. The supernate with starch granular proteins was retained for electrophoresis (below). These proteins were either run on SDS-PAGE or native-PAGE in order to detect the protein levels and their activities, respectively (according to the procedures described below).

SDS-PAGE (Denaturing and Non-denaturing) and Detection of Enzyme Activity

Figure 10:
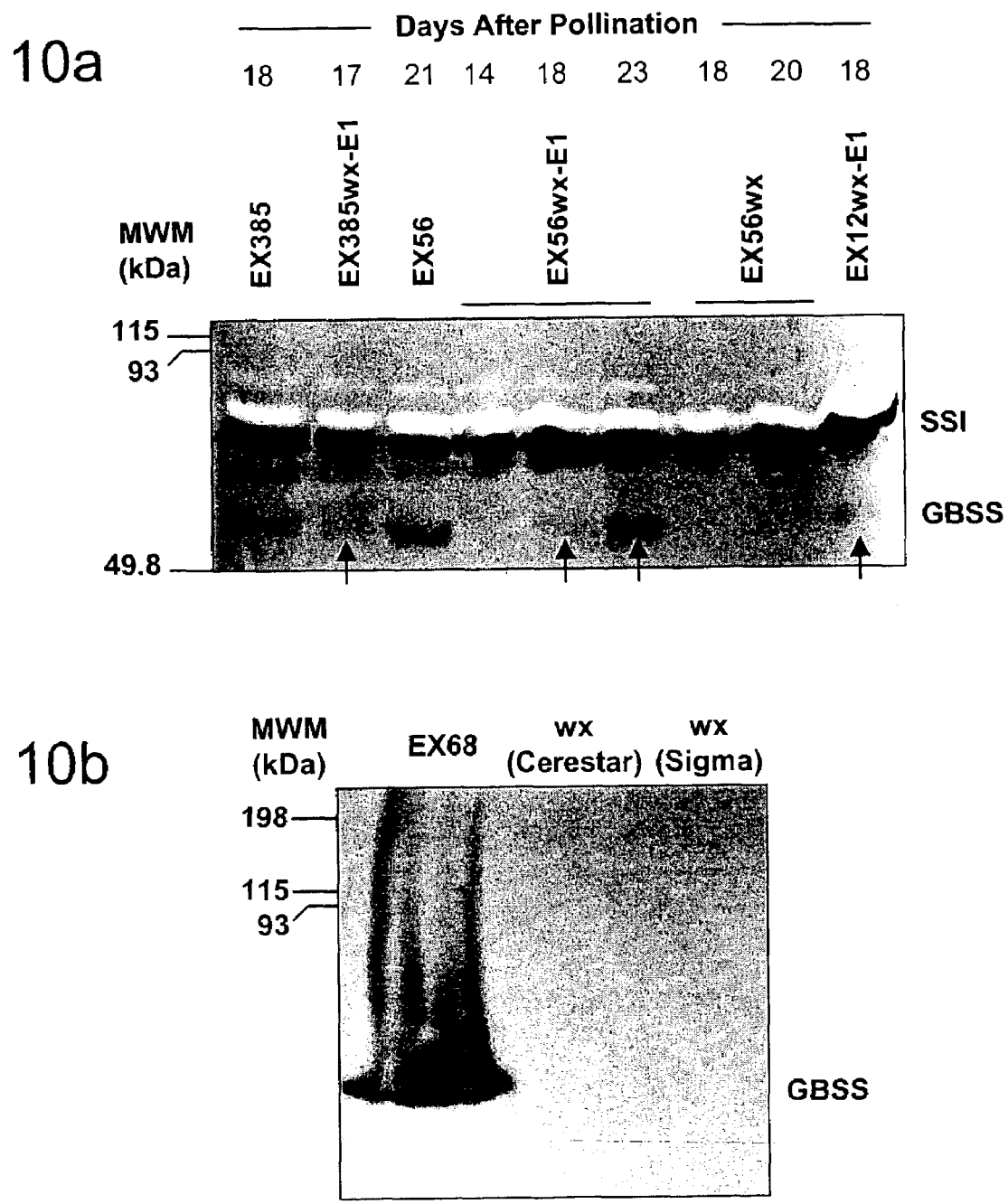
FIG. 10.(a) Detection of starch synthase activities associated with immature starch granules (14 to 23 days) in renaturing gradient gels (7 to 20%). An equal amount of starch (based on fresh weight) was loaded in each lane. The identity of the starch and the maturity of the seed for each lane are indicated. (b) Detection of starch synthase activities associated with mature starch granules in renaturing gels (7 to 20%). An equal amount of starch was loaded in each lane. The identity of the starch for each lane is indicated.

Polyacrylamide (37.5:1 w/w acrylamide:bis-acrylamide) gels of either 8% straight (for Biorad MiniProtean III apparatus) or 7% to 20% gradient (Biorad Protean II) under non-denaturing conditions, and 10% or 12% under denaturing conditions (with 0.1% sodium dodecyl sulphate (SDS)) were run according to Laemmli (Laemmli, U.K., 1970, Nature 227:680–685). The non-denaturing gels contained either 0.1% rabbit liver glycogen or potato amylopectin and were electrophoresed in a running buffer (25 mM Tris, 192 mM glycine, 1% SDS) containing 5 mM DTT. The denaturing gels contained either 0.1% rabbit liver glycogen or potato amylopectin and were electrophoresed in a running buffer without DTT. At the end of the electrophoresis, denaturing gels were incubated in the renaturation buffer (40 mM Tris, 5 mM DTT) for 90 min to 2 h with a change of solution after every 30 min. The non-denaturing gels were incubated in 5 to 10 ml of the reaction buffer [10 mg/ml glycogen, 5 mM ADPG, 5 mM glutathione, 0.5 mg/ml BSA, 25 mM potassium acetate, 100 mM Bicine (pH 8.5), 2M citrate] for 12 h, and the denaturing SDS gels were incubated in the same buffer for 48 h. At the end of the incubation gels were stained with iodine solution (2% KI and 0.2% $I_2$ in 0.01 N HCl) to detect the band(s) having starch synthase activity (FIGS. 10a and 10b). The figures clearly show GBSS activity in all of the waxy-E starches, that the activity of GBSS in waxy-E starches is lower than with normal, and that there is no activity in the lab-isolated waxy starch EX56wx or the commercial waxy starches.

Western Blotting

An SDS gel (stacker 15 mA and 20 mA for gel) was soaked in 100 mL of Towbins buffer (25 mM pH 8.3 Tris-acetate; 192 mM glycine) for 10 minutes, with a nitrocellulose membrane. At the same time, a Towbins transfer buffer composed of 800 mL of Towbins buffer and 200 mL of methanol was made. The soaked gel and nitrocellulose membrane were sandwiched together in a gel holder cassette (composed of a sponge, filter paper, gel, nitrocellulose, and filter paper). Air bubbles were removed from the cassette by rolling a glass pipette over the sponge, the gel holder cassette was snapped shut and placed in the transblot module. The transfer in Towbins transfer buffer was conducted at 300 mA for 1 hour. The nitrocellulose membrane was stained with Ponceuau-S (Sigma, catalog number P7767) 5:45 mls dilution from stock) for 10 minutes. The membrane was then incubated in 5% skim milk in TBS buffer+Tween 20 (TBST: 10 mM pH 7.5 Tris; 150 mM sodium chloride; 0.1% Tween 20) for 1.5 to 2 h at room temperature or at 4° C. overnight. After this, the membrane was incubated with primary antibody (1:3000–60 kDa) for 2 hours at room temperature or 4° C. overnight. The membrane was then washed 3 times with TBST for 15 minutes each time at room temperature followed by incubation with secondary antibody (1:3000 goat anti-rabbit IGg with AP conjugate, Biorad, catalog number 1706518) for 1 hour at room temperature. The membrane was then washed three times with TBST for 15 minutes each time at room temperature and the cross reactivity of antibody with GBSS enzyme was detected by developing the membrane using a mixture of 33 μl of a solution of 10 mg of 5-bromo-4-chloro-3-indolyl phosphate (BCIP: Sigma, catalog number B6777) in 2 mL of dimethyl formamide and 330 μl of a solution of 200 mg of nitro blue tetrazolium (NBT) in 2 mL of 70% dimethyl formamide) in 10 ml of alkaline phosphate buffer (100 mM pH 9.5 Tris-sodium hydroxide, 100 mM sodium chloride, 5 mM magnesium chloride). The membrane was then washed with distilled-deionized $H_2O$. The reaction was stopped using 5 mM ethylene-diamine tetraacetic acid. For detection of the levels of SSI protein in starch samples, the same procedure as described above was followed using a 1:3000 dilution of antibody for 77 kDa protein. Developed membranes are presented in FIGS. 11a and 11b. The membranes clearly show that GBSS protein is present in all of the waxy-E starches and is absent from the lab isolated waxy starch. Both commercial waxy starches show a very low level of GBSS protein which is likely to be from contaminating normal starch (Example 1 and FIG. 1) due to commercial starch isolation practices.

Coomassie Staining of Proteins

Figure 12:
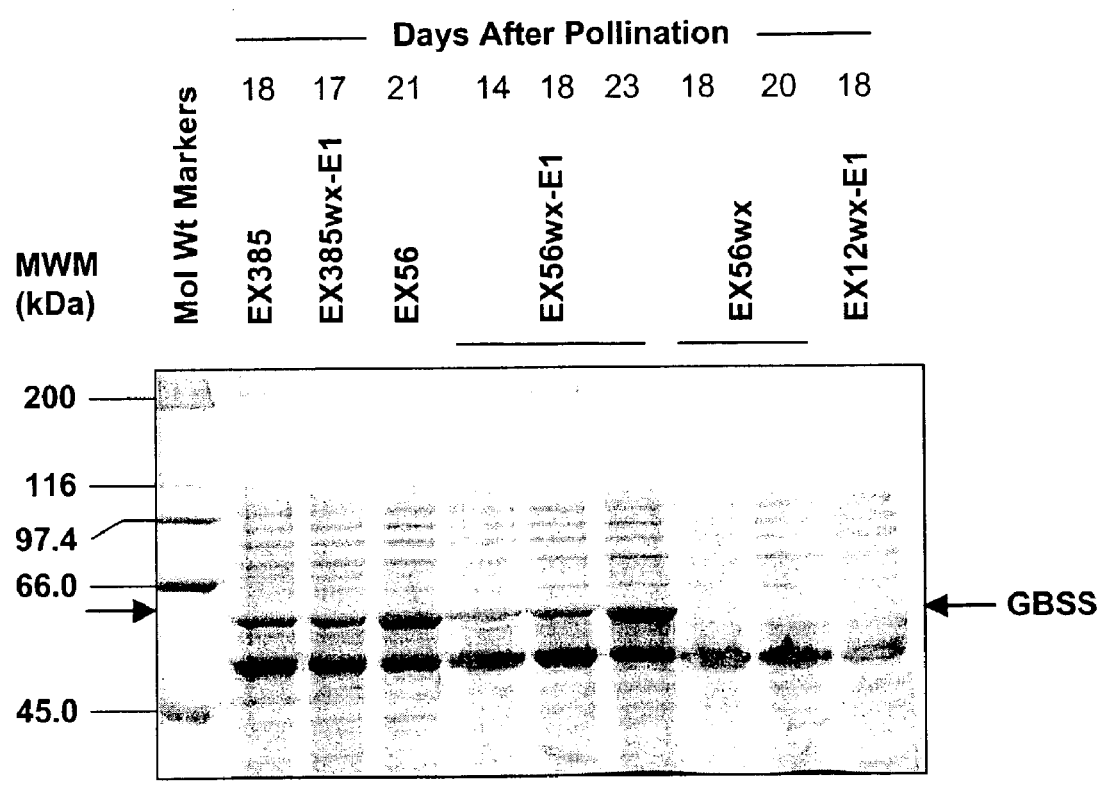
FIG. 12. Detection of the quantity of GBSS protein associated with immature starch granules (14 to 23 days) using coomassie staining. The identity of the starch and the maturity of the seed for each lane is indicated.

At the end of the gel electrophoresis, proteins were stained with coomassie blue in a buffer containing 43% de-ionized water, 40% methanol, 17% glacial acetic acid, and 0.1% coomassie brilliant blue R-250 (Biorad) for at least 40 min. Gels were briefly rinsed with de-ionized water and were de-stained for 20 min in a buffer containing 50% de-ionized water, 40% methanol, and 10% glacial acetic acid (De-stain-I), followed by de-staining for at least 40 min in a buffer solution containing 88% de-ionized water, 5% methanol, and 7% glacial acetic acid (De-stain II). At the end of the de-staining procedure, the gels were soaked in de-ionized water in order to get rid of any trace amounts of acetic acid trapped in the gel matrix. The wx-E1 starches had a level of GBSS during development which appeared substantially equivalent to the level of GBSS in the wild type plants, as observed by the level of staining of the bands associated wth GBSS in the gel (FIG. 12). The wx-E2 starch had a level of GBSS which was subtantially reduced as observed by the level of staining of the band associated with GBSS in the gel.

Example 13

Identification of a Point Mutation in the Nucleic Acid Sequence Encoding Granule-Bound Starch Synthase The waxy gene from EX385 wild type and EX385wx-E1 mutant seed were sequenced and compared to identify an EMS-induced point mutation. To do this, total RNA was isolated from immature kernels harvested 17–18 days after pollination using standard protocols. The RNA was used as a template to synthesize complementary DNA (cDNA) using the enzyme reverse transcriptase by standard protocols. The cDNA was then used as a template for the polymerase chain reaction (PCR) to amplify the GBSS coding sequence using two pairs of oligonucleotide primers by conventional methods. The PCR amplified product was then used as a template in dideoxynucleotide sequencing reactions that utilized sequencing primers specific to the GBSS nucleic acid sequence. Techniques for the above methods are described in Current Protocols in Molecular Biology, John Wiley & Sons, Inc. The sequences from EX385 and EX385wx-E1 were compared to each other, as well as to the GBSS sequence (accession number X03935; SEQ ID NO:5) available in Genbank, a public database. The GBSS sequence from EX385wx-E1 (SEQ ID NO:2) had a single base pair change relative to that from EX385 wild type (SEQ ID NO:1), located at position+1643 from the transcription start site. This mutation changes amino acid 484 from a glycine in EX385 (SEQ ID NO:3) to a serine in EX385wx-E1 (SEQ ID NO:4).

Example 14

Starch Application—Lemon Pie Filling

This experiment was conducted to illustrate the benefits of waxy-E starch in a lemon pie filling application. Lemon pie fillings were prepared with normal starches (EX68, Cerestar-USA commercial normal starch C*Gel 03420), waxy starches (EX68wx, Cerestar-USA commercial waxy starch C*Gel 02430), and waxy-E starches (EX385wx-E1, EX56wx-E1, EX78wx-E1, and EX12wx-E2). The following formulation for lemon pie filling was utilized (Table 17):

TABLE 17

Lemon Pie Filling Formulation

| Ingredient | Mass (%) | Mass (40 g scale) |
|---|---|---|
| Dry Ingredients | | |
| Granulated Sugar | 25.54 | 10.22 |
| Starch (10% moisture basis) | 4.55 | 1.82 |
| Salt | 0.19 | 0.08 |
| Liquid Ingredients | | |
| Water | 46.09 | 18.44 |
| Lemon Juice | 11.71 | 4.68 |
| Egg Yolk | 9.66 | 3.86 |
| Shortening | | |
| hydrogenated vegetable shortening (melted) | 2.26 | 0.91 |

All of the dry ingredients except the starch were combined preceeding the experiment on a large scale (500 g total prepared and termed the lemon pie filling pre-mix). Liquid ingredients (the water, lemon juice, and egg yolk) for each individual analysis were also combined in advance. The moisture content of each starch was accounted for in the formulation; all formulations utilized an equal mass of starch on a dry weight basis. Fillings (40 g) were processed using a Rapid-Visco-Analyzer as a temperature-controlled mixer. To prepare the fillings, the starch and lemon pie filling pre-mix were added to an RVA sample cup and thoroughly mixed using the stirring paddle to be used for that sample. The prepared mixtures of dry ingredients and liquid ingredients (no shortening) had a pH of 3.3; indicating that the starch was in a highly acidic environment. The liquid ingredients were then added to the RVA sample cup containing the dry ingredients and the stirring paddle agitated to thoroughly suspend the sample solids in the liquid medium. The lemon filling was mixed at 960 rpm for 10 seconds and then mixed at 160 rpm for the remainder of the first step of the cooking process. The first step of the cooking process lasted 9 minutes during which the filling was heated using the following program: the ingredients were held at 50° C. for 1 min, heated from 50° C. to 95° C. for 7.5 min, then held at 95° C. for 0.5 min. After the first step of the cooking process, the melted vegetable shortening was added to the filling within 15 seconds. The filling was then stirred at 480 RPM for 15 seconds to incorporate the shortening with the other ingredients. Stirring at 160 RPM then resumed and continued for the remainder of the cooking process: fillings were heated at 95° C. for an additional 2 minutes, cooled to 50° C. over 4.5 minutes, then held at 50° C. for 3 minutes. The entire cooking process lasted 19 minutes. Immediately after cooking, the finished lemon pie filling was added to a 50 mL tube and placed in a 4° C. refrigerator for storage. Two replicates of the experiment were conducted, and the analysis order of the second replicate was the opposite of the first replicate in an attempt to eliminate any confounding effect of storage time on the results.

Lemon fillings prepared with normal starches had formed highly rigid gels within 24 hours of storage at 4° C. and syneresed strongly after 7 days of storage at 4° C. Rheological measurements were not conducted on these samples at either time point. Samples of lemon fillings prepared with waxy starches or waxy-E starches were taken for rheological analysis after 24 hours at 4° C. and after 7 days at 4° C.; none of the samples syneresed over the course of the week of storage at 4° C. Frequency and strain dependence of lemon pie fillings were tested using a rheometer (RFSIII Fluids Spectrometer, Rheometric Scientific, Piscataway N.J.). All fillings were measured at 25° C. A parallel plate geometry was utilized for testing (50 mm; 0.9 to 1.1 mm gap width); loaded samples were permitted to rest between the plates of the rheometer for 10 minutes in order for them to come to 25° C. and also to reduce the effects of loading on the measurements. A thin film of oil was applied to the exposed surface of the filling between the rheometer plates to minimize moisture evaporation during the testing process. Frequency dependence of a filling was always examined first, followed by the strain dependence. The frequency dependence of lemon pie fillings was tested between 0.1 and 100 radians per second with a oscillatory strain of 1%. Strain dependence of lemon pie fillings was tested between 0.1 and 1000% deformation at a constant testing frequency of 1 radian per second. The strain and frequency dependence of the lemon pie fillings stored for 24 hours and 7 days at 4° C. prepared with waxy and waxy-E starches is presented in Table 18 and Table 19, respectively. The results of each replicate are shown.

Fillings made with waxy-E starch stored for 24 hours at 4° C. showed lower frequency dependence than did any of the waxy starches (Table 18 and 19), with a 2–3 fold increase in G' between a frequency of 0.1 and 100 radians per second compared to fillings made with waxy starches which generally had a 5–10 fold increase over the same frequency range. The lower frequency dependence of fillings made with waxy-E starches shows that the waxy-E starches contribute more gel-like character to the fillings than do waxy starches.

TABLE 18

Rheology of Lemon Pie Fillings - Storage for 24 Hours at 4° C.

| | Frequency Dependence | | | | Strain Dependence | | | | | |
|---|---|---|---|---|---|---|---|---|---|---|
| | 0.1 rad/s | | 100 rad/s | | 1% | | 200% | | 1000% | |
| Starch Source | G' (Pa) | phase angle (deg) | G' (Pa) | phase angle (deg) | G' (Pa) | phase angle (degrees) | G' (Pa) | phase angle (degrees) | G' (Pa) | phase angle (degrees) |
| wx starch | | | | | | | | | | |
| EX68wx | 3 | 27 | 38 | 40 | 7 | 31 | 3 | 48 | 2 | 64 |
| | 2 | 29 | 38 | 40 | 6 | 33 | 3 | 48 | 2 | 64 |
| C* waxy | 8 | 18 | 44 | 35 | 13 | 22 | 7 | 31 | 3 | 59 |
| | 12 | 17 | 54 | 36 | 16 | 20 | 7 | 33 | 3 | 56 |
| waxy-E starch | | | | | | | | | | |
| EX56wx-E1 | 48 | 5 | 98 | 19 | 58 | 7 | 41 | 17 | 5 | 67 |
| | 68 | 5 | 132 | 17 | 78 | 6 | 42 | 24 | 6 | 66 |
| EX385wx-E1 | 95 | 5 | 165 | 15 | 108 | 5 | 50 | 27 | 6 | 70 |
| | 94 | 3 | 167 | 15 | 107 | 5 | 50 | 28 | 6 | 70 |
| EX78wx-E1 | 76 | 5 | 142 | 17 | 88 | 6 | 22 | 26 | 5 | 70 |
| | 91 | 4 | 162 | 15 | 102 | 5 | 46 | 29 | 7 | 68 |
| EX12wx-E1 | 25 | 11 | 73 | 27 | 33 | 14 | 17 | 24 | 4 | 62 |
| | 24 | 9 | 74 | 26 | 30 | 12 | 17 | 26 | 4 | 61 |

TABLE 19

Rheology of Lemon Pie Fillings - Storage for 7 Days at 4° C.

| | Frequency Dependence | | | | Strain Dependence | | | | | |
|---|---|---|---|---|---|---|---|---|---|---|
| | 0.1 rad/s | | 100 rad/s | | 1% | | 200% | | 1000% | |
| Starch Source | G' (Pa) | phase angle (deg) | G' (Pa) | phase angle (deg) | G' (Pa) | phase angle (degrees) | G' (Pa) | phase angle (degrees) | G' (Pa) | phase angle (degrees) |
| wx starch | | | | | | | | | | |
| EX68wx | 5 | 22 | 42 | 37 | 9 | 26 | 4 | 43 | 3 | 57 |
| | 7 | 24 | 51 | 36 | 11 | 25 | 5 | 44 | 3 | 56 |
| C* waxy | 16 | 12 | 64 | 30 | 22 | 15 | 11 | 30 | 5 | 53 |
| | 18 | 12 | 65 | 30 | 23 | 15 | 11 | 30 | 5 | 51 |
| waxy-E starch | | | | | | | | | | |
| EX56wx-E1 | 59 | 5 | 124 | 18 | 69 | 7 | 37 | 23 | 5 | 67 |
| | 73 | 4 | 140 | 17 | 82 | 6 | 43 | 25 | 7 | 67 |
| EX385wx-E1 | 120 | 4 | 200 | 13 | 133 | 4 | 54 | 33 | 7 | 71 |
| | 113 | 4 | 191 | 14 | 126 | 5 | 51 | 32 | 6 | 71 |
| EX78wx-E1 | 112 | 4 | 198 | 14 | 126 | 5 | 43 | 38 | 6 | 72 |
| | 118 | 3 | 201 | 13 | 131 | 5 | 45 | 38 | 6 | 72 |
| EX12wx-E1 | 44 | 7 | 108 | 22 | 52 | 9 | 24 | 28 | 5 | 64 |
| | 43 | 7 | 104 | 21 | 51 | 9 | 23 | 29 | 6 | 63 |

Fillings made with waxy-E starch stored for 24 hours at 4° C. had a higher elastic modulus at 1% strain than the elastic modulus of fillings made with waxy starch, exceeding 4-fold in all cases and roughly 8–10 fold for all of the wx-E1 group starches. Additionally, the phase angles of waxy-E starch fillings at 1% strain were lower compared with the phase angles of fillings made with waxy starch, indicating that a higher proportion of the complex modulus of fillings made with waxy-E starch is attributable to the elastic component of the filling compared to those fillings made with waxy starch. Thus, the fillings made with waxy-E starches are considerably different rheologically from those fillings made with waxy starch.

For fillings stored for 24 hours at 4° C., the elastic modulus of fillings made with waxy-E starches remained higher than the elastic modulus of fillings made with waxy starch through 1000% strain. Additionally, through 200% strain the fillings made with waxy-E starch maintained lower phase angles than the fillings made with waxy starch. Thus, fillings made with waxy-E starch not only retained a relatively high elastic modulus but also a relatively high elasticity (as a component of the complex modulus, indicated by the low phase angles) through high deformations compared to fillings made with waxy starch.

Finally, fillings made with waxy-E starches and waxy starches stored 24 hours at 4° C. vs. stored for 7 days at 4°

C. had similar frequency dependent behavior, strain dependent behavior, an elastic modulus magnitudes, and phase angles. This similarity between the measurements after 24 hours and 7 days indicates that the filling properties did not change much over the course of six additional days of storage at 4° C., indicative of the useful low-temperature stability of formulations containing waxy-E starch. Large changes in any of these properties would have indicated the development of additional structure in the filling, which would be undesirable for applications requiring extended storage at low temperatures such as pie fillings used for ready-to-eat pies distributed from a centralized wharehouse to retail outlets. Waxy starches themselves have good low temperature stability, but they do not provide the higher elasticity that waxy-E starches provide.

The waxy-E starches, because of their high elasticity and low temperature stability, could additionally act to suspend for fruit or other large particles in food formulations including pies, puddings, soups, yoghurts, sauces, and other foodstuffs. The waxy starch pastes, though viscous, do not form sufficient paste structure to act as a useful suspension aid. Additionally, because of the unique rheological characteristics of waxy-E starch pastes and gels, they could be used for coatings and films in foodstuffs such as batter coatings. Once deposited on a surface, a paste of waxy-E starch will have a better tendency than waxy starch to cling and adhere to a surface rather than flow with gravity.

Although the examples above contain many specificities, these should not be construed as limiting the scope of the invention but as merely providing illustrations of some of the presently preferred embodiments of this invention. Various other embodiments and ramifications are possible within it's scope and are readily apparent to those skilled in the art. Accordingly, the spirit and scope of the invention are to be limited only by the appended claims and not by the foregoing specification.

WO028052 Nucleic acid molecules from rice and their use for the production of modified starch WO9211376 Genetically engineered modification of potato to form amylopectin-type starch WO09535026 Novel plants and processes for obtaining them WO9720936 Starch Synthase Sequences WO9844780 Starch Synthase Hosts WO9814601 EnCapsulation WO09815621 Waxy wheat starch types having waxy proteins in granule WO09827212 Novel nucleic acid molecules from maize and their use for the production of modified starch WO9924575 Dull1 Starch Synthase III JP04104791 Use of waxy gene to control the amylose content of rice EP788735 Potato plant, tuber, seed and microtuber engineered to form starch EP1102547 Heat-Stable High-Amylopectin Starch U.S. Pat. No. 5,302,523 Transformation of plant cells U.S. Pat. No. 5,464,765 Transformation of plant cells U.S. Pat. No. 4,428,972 Starch thickener characterized by improved low-temperature stability U.S. Pat. No. 4,615,888 Bread containing wxsu2 genotype starch as an anti-stalent U.S. Pat. No. 4,767,849 Starch of the wxsh1 genotype and products produced therefrom U.S. Pat. No. 4,789,557 Foodstuffs containing starch of a dull waxy genotype U.S. Pat. No. 4,789,738 Starch of wxfl1 genotype and products produced therefrom U.S. Pat. No. 4,801,470 Foodstuffs containing starch of a waxy shrunken-2 genotype U.S. Pat. No. 5,009,911 Foodstuff containing aewx starch U.S. Pat. No. 5,482,560 Beta-limit dextrin from dull waxy starch U.S. Pat. No. 5,356,655 Starch-thickened acidic foodstuffs and method of preparation U.S. Pat. No. 5,502,270 Starch and grain with a novel genotype U.S. Pat. No. 5,516,939 Starch and grain with a novel genotype U.S. Pat. No. 6,165,535 Wheat starch with novel characteristics U.S. Pat. No. 5,004,864 Dominant amylose-extender mutant of maize Andersson, L., Fredriksson, H., Oscarsson Bergh, M., Andersson, R., and Åman, P. 1999. Journal of Cereal Science 30:165–171.

Anonymous. 1998. Ch. 7, General applications, in the Applications Manual for the Rapid Visco Analyzer, Newport Scientific Pty. Ltd., Warriewood NSW, Australia.

Atwell, W. A., Hood, L. F., Lineback, D. R., Varriano-Marston, E., and Zobel, H. F. 1988. The terminology and methodology associated with basic starch phenomena. Cereal Foods World 33(3): 306–311.

Baba, T., Nishihara, M., Mizuno, K., Kawasaki, T., Shimada, I I., Kobayashi, E., Ohnishi, S., Tanaka, K. and Arai, Y. 1993. Identification, cDNA cloning, and gene expression of soluble starch synthase in rice (Oryza sativa L.) immature seeds. Plant Physiology 103:565–573.

Bailey, J. M. and Whelan, W. J. 1961. Physical properties of starch. I. Relationship between iodine stain and chain length. The Journal of Biological Chemistry 236:969–973.

Banks, W., Greenwood, C. T., and Khan, K. M. 1971. The interaction of linear, amylose oligomers with iodine. Carbohydrate Research 17:25–33.

Bett-Garber, K. L., Champagne, E. T., McClung, A. M., Moldenhauer, K. A., Linscombe, S. D., and McKenzie, K. S. 2001. Categorizing rice cultivars based on cluster analysis of amylose content, protein content, and sensory attributes. Cereal Chemistry 78:551–558.

Biliaderis, C. G. 1992. Characterization of starch networks by small strain dynamic rheometry, in Developments in Carbohydrate Chemistry, R. J. Alexander and H. F. Zobel, eds. The American Association of Cereal Chemists, St. Paul.

Boyer, C. D. 1985. Soluble starch synthases and starch branching enzymes from developing seeds of sorghum. Phytochemistry 24:15–18.

Boyer, C. D. and Preiss J. 1978. Multiple forms of (1 to 4)-alpha-D-glucan, (1 to 4)-alpha-D-glucan-6-glycosyl transferase from developing Zea mays L. kernels Carbohydrate Research 61:321–334.

Boyer, C. D., Garwood, D. L., and Shannon, J. C. 1976. Interaction of the amylose-extender and waxy mutants of maize. The Journal of Heredity 67:209–214.

Brimhall, B., Sprague, G. F., and Sass, J. E. 1945. A new waxy allel in corn and its effect on the properties of the endosperm starch. Journal of the American Society of Agronomy 37:937–944

Champagne, E. T., Bett, K. L., Vinyard, B. T., McClung, A. M., Barton, F. E., Moldenhauer, K., Linscombe, S., and McKenzie, K. 1999. Correlation between cooked rice texture and rapid visco analyser measurements. Cereal Chemistry 76:764–771.

Coe, E. H., Neuffer, M. G., and Hoisington, D. A. 1988. The genetic of corn, in Corn and Corn Improvement, 3rd edition, G. F. Sprague and J. W. Dudley, eds. American Society of Agronomy, Madison.

Craig, S. A. S., Maningat, C. C., Seib, P. A., and Hoseney, R. C. 1989. Starch paste clarity. Cereal Chemistry 66:173–182.

Creech, R. G. 1965. Genetic control of carbohydrate synthesis in maize endosperm. Genetics 52:1175–1186.

Dang, P. L. and Boyer, C. D. 1988. Maize leaf and kernel starch synthases and starch branching enzymes. Phytochemistry 27:1255–1259

Delrue, B., Fontaine, T., Routier, F., Decq, A., Wieruszeski, J. M., van der Koornhuyse, N., Maddelein, M. L., Fournet, B., and Ball, S. 1992. Waxy Chlamydonas reinhardtii: monocellular algal mutants defective in amylose biosynthesis and granule-bound starch synthase activity accumulate a structurally modified amylopectin. Journal of Bacteriology 174:3612–3620.

Denyer, K., Foster, J. M., and Smith, A. M. 1995. The contribution of adenosine 5'-diphosphglucose pyrophosphorylase and starch-branching enzyme to the control of starch synthesis in developing pea embyros. Planta 197:57–62.

Denyer, K., Sidebottom, C., Hylton, C. M. and Smith, A. M. 1993. Soluble isoforms of starch synthase and starch branching enzyme also occur within starch granules in developing pea embryos. The Plant Journal. 4:191–198.

Denyer, K., Barber, L. M., Burton, R., Hedley, C. L., Hylton, C. M., Johnson, S., Jones, D. A., Marshall, J., Smith, A. M., Tatge, H., Tomlinson, K., and Wang, T. L. 1995. The isolation and characterization of novel low-amylose mutants of *Pisum sativum* L. Plant Cell and Environment 18:1019–1026.

Denyer, K., Clarke, B. and Smith, A. 1996. The elongation of amylose and amylopectin chains in isolated starch granules. The Plant Journal 10:1135–1143.

Denyer, K. and Smith, A. M. 1992. The purification and characterization of two forms of soluble starch synthase from developing pea embryos. Planta 186:609–617.

Denyer, K., Waite, D., Motawia, S., Lindberg-Moller, B. and Smith, A. M. 1999a. Granule-bound starch synthase I in isolated starch granules elongates maltooligosaccharides processively. Biochemical Journal 340:183–191.

Denyer, K., Waite, D., Edwards, A., Martin, C. and Smith, A. M. 1999b. Interaction with amylopectin influences the ability of granule-bound starch synthase I to elongate maltooligosaccharides. Biochemical Journal 342:647–653.

Dry, I., Smith, A., Bhattacharyya, M., Dunn, P. and Martin, C. 1992. Characterization of cDNAs encoding two isoforms of granule-bound starch synthase which show differential expression in developing storage organ of pea and potato. The Plant Journal 2:193–202.

Dubois, M., Gilles, K. A., Hamilton, J. K., Rebers, P. A., and Smith, F. 1956. Colorimetric method for determination of sugars and related substances. Analytical Chemistry 28(3):350–356.

Echt, C, and Schwartz, D. 1981. The wx locus is the structural gene for the Wx protein. Maize Genetics Cooperation Newsletter 55:8–9.

Eckhoff, S. R., Singh, S. K., Zehr, B. E., Rausch, K. D., Fox, E. J., Mistry, A. K., Haken, A. E., Niu, Y. X., Zou, S. H., Buriak, P., Tumbleson, M. E., and Keeling, P. L. 1996. A 100-g laboratory corn wet-milling procedure. Cereal Chemistry. 73:54–57.

Edwards, A., Marshall, J., Sidebottom,C., Visser, R. G. F., Smith, A. M. and Martin, C. 1995. Biochemical and molecular characterization of a novel starch synthase from potato tubers. The Plant Journal 8(2): 283–294.

Edwards, A., Marshall, J., Denyer, K., Sidebottom, C., Visser, R. G. F., Martin, C. and Smith, A. M. 1996. Evidence that a 77-Kilodalton protein from the starch of pea embryos is an isoform of starch synthase that is both soluble and granule bound. Plant Physiology 112:89–97.

Eliasson, A.-C. and Kim, H.-R. 1995. A dynamic rheological method to study the interaction between starch and lipids. Journal of Rheology 39:1519–1534.

Fisher, D. K., Boyer, C. D. and Hannah, L. C. 1993. Starch branching enzyme II from maize endosperm. Plant Physiology 102:1045–1046

Fisher D. K., Kim, K. N., Gao, M., Boyer, C. D. and Guiltinan, M. J. 1995. A cDNA encoding starch branching enzyme I from maize endosperm. Plant Physiology 108: 1313–1314

Flipse, E., Keetels, C. J. M., Jacobsen, E., Visser, R. G. F. 1996. The dosage effect of the wild type GBSS allele is linear for GBSS activity but not for amylose content: Absence of amylose has a distict influence on the physicochemical properties of starch. Theoretical and Applied Genetics 92: 121–127

Frydman, R. B. and Cardini, C. E. 1964. Biochemical and Biophysical Research Communications 17:407–411.

Gao, M., Fisher, D. K., Kim, K. N., Shannon, J. C. and Guiltinan, M. J. 1997. Independent genetic control of maize starch-branching enzymes IIa and IIb. Plant Physiology 114:713–722

Gao, M., Wanat, J., Stinard, P. S., James, M. G. and Myers, A. M. 1998. Characterization of dull1, a maize gene coding for a novel starch synthase. The Plant Cell. 10:399–412.

Garwood, D. L. and Vanderslice, S. F. 1982. Carbohydrate composition of alleles at the sugary locus in maize *Zea mays*. Crop Science 22:367–371.

Garwood, D. L., Shannon, J. C., and Creech, R. G. 1976. Starches of endosperms possessing different alleles at the amylose-extender Locus in *Zea mays* L. Cereal Chemistry 53:355–364.

Gidley, M. J. and Bulpin, P. V. 1989. Aggregation of amylose in aqueous systems: The effect of chain length on phase behavior and aggregation kinetics. Macromolecules. 22:341–346.

Glover, D. V. and Mertz, E. T. 1987. Corn, in Agronomy. American Society of Agronomy, Madison.

Guan, H. and Keeling, P. L. 1998. Understanding the functions and interactions of multiple isozymes of starch synthase and branching enzyme. Trends in Glycoscience 10:307–319.

Harn, C., Knight, M., Ramakrishnan, A., Guan H., Keeling, P. L. and Wasserman, B. P. 1998. Isolation and characterization of the zSSIIa and zSSIIb starch synthase cDNA clones from maize endosperm. Plant Molecular Biology 37:639–649.

Hawker, J. S. and Jenner, C. F. 1993. High temperature affects the activity of enzymes in the committed pathway of starch synthesis in developing wheat endosperm. Australian Journal of Plant Physiology 20:197–209.

Hizukuri, S., Takeda, Y., Yasuda, M., and Suzuki, A. 1981. Multi-branched nature of amylose and the action of debranching enzymes. Carbohydr. Research 94:205–213

Hizukuri, S., Takeda, Y., Maruta, N. and Julian, B. O. 1989. Molecular structures of rice starch. Carbohydrate Research. 189:227–235.

Holder, D. G., Glover, D. V., and Shannon, J. C. 1974. Interaction of shrunken-2 with five other carbohydrate genes in corn endosperm. Crop Science 14:643–646.

Hovenkamp-Hermelink, J. H. M., Jacobsen, E., Ponstein, A. S., Visser, R. G. F., Vos-Scheperkeuter, G. H., Bijmolt, E. W., de Vries, J. N., Witholt, B., and Feenstra, W. J. 1987. Isolation of an amylose-free starch mutant of the potato (*Solanum tuberosum* L.) Theoretical and Applied Genetics 75:217–221.

Imparl-Radosevich, J. M., Keeling, P. L., and Guan, H. 1999. Essential arginine residues in maize starch synthase IIa are involved in both ADP-glucose and primer binding. FEBS Left. 457:357–362.

Imparl-Radosevich, J. M., Li, P., Zhang, L., McKean, A. L., Keeling, P. L. and Guan, H. 1998a. Purification and characterization of maize starch synthase I and its truncated forms. Archives of Biochemistry and Biophysics 353(1): 64–72.

Imparl-Radosevich, J. M., Nichols, D. J., Li, P., McKean, A. L., Keeling, P. L. and Guan, H. 1998b. Analysis of purified maize starch synthases IIa and IIb: SS isoforms can be distinguished based on their kinetic properties. Archives of Biochemistry and Biophysics 362(1): 131–138.

Isshiki, M., Morino, K., Nakajima, M., Okagaki, R. J., Wessler, S. R., Izawa, T., and Shimamoto, K. 1998. A naturally occurring functional allele of the rice waxy locus has a GT to TT mutation at the 5' splice site of the first intron. The Plant Journal 15:133–138.

Jane, J. and Chen, J. 1992. Effect of amylose molecular size and amylopectin branch chain length on paste properties of starch. Cereal Chemistry 69(1):60–65.

Jane, J., Chen, Y. Y., Lee, L. F., McPherson, A. E., Wong, K. S., Radosavljevic, M., and Kasemsuwan, T. 1999. Effects of amylopectin branch chain length and amylose content on the gelatinization and pasting properties of starch. Cereal Chemistry 76:629–637.

Jane, J.-I., Kasemsuwan, T., Leas, S., Zobel, H., and Robyt, J. F. 1994. Anthology of starch granule morphology by scanning electron microscopy. Starch/Stärke. 46:121–129.

Jenner, C. F., Siwek, K. and Hawker, J. S. 1993. The synthesis of 14C starch from 14C sucrose in isolated wheat grains is dependent upon the activity of soluble starch synthase. Australian Journal of Plant Physiology 20:329–335.

Jenner, C. F., Denyer, K. and Guerin, J. 1995. Thermal characteristics of soluble starch synthase from wheat endosperm. Australian Journal of Plant Physiology 22:703–709.

Juliano, B. O., Nazareno, M. B., and Ramos, N. B. 1969. Properties of waxy and isogenic nonwaxy rices differing in starch gelatinization temperature. Journal of Agricultural and Food Chemistry 17:1364–1369.

Kainuma K. 1988. Structure and chemistry of the starch granule. In The Biochemistry of Plants, Vol 14, J. Preiss, ed. Academic Press, San Diego, pp.141–180.

Keeling, P. L., Bacon, P. J. and Holt, D. C. 1993. Elevated temperature reduces starch deposition in wheat endosperm by reducing the activity of soluble starch synthase. Planta. 191:342–348.

Keeling, P. L., Banisadr, R., Barone, L., Wasserman, B. P. and Singletary, G. W. 1994. Effect of temperature on enzymes in the pathway of starch biosynthesis in developing wheat and maize grain. Australian Journal of Plant Physiology 21:807–827.

Kiribuchi-Otobe, C., Yanagisawa, Y., Yamaguchi, I., and Yoshida, H. 1998. Wheat mutant with waxy starch showing stable hot paste viscosity. Cereal Chemistry 75:671–672

Klucinec, J. D. and Thompson, D. B. 1998. Fractionation of high-amylose maize starches by differential alcohol precipitation and chromatography of the fractions. Cereal Chemistry 75:887–896.

Klucinec, J. D. and Thompson, D. B. 1999. Amylose and amylopectin interact in retrogradation of dispersed high-amylose starches. Cereal Chemistry 76:282–291.

Klucinec and Thompson, 2001a. Structure of amylopectins from ae-containing maize starches. Cereal Chemistry, accepted.

Klucinec and Thompson 2001b. The nature of amylopectin and the amylose to amylopectin ratio both influence the nature of starch gels from mixtures of amylopectin and amylose. Cereal Chemistry, accepted.

Knight, E., Harn, C., Lilley, C. E. R., Guan, H., Singletary, G. W., Mu-Forster, C., Wasserman, B. P. and Keeling, P. L. 1998. Molecular cloning of starch synthase from maize (W64) endosperm and expression in *Escherichia coli*. The Plant Journal 14:613–622

Kusnadi, A. R., Ford, C. and Nikolov, Z. L. 1993. Functional starch-binding domain of Aspergillus glucoamylose I in *Escherichia coli*: Maltose-binding protein; fusion protein; factor Xa; recombinant DNA. Elsevier Science Publishers. 193–197.

Knutson, C. A. and Grove, M. J. 1994. Rapid method for estimation of amylose in maize starches. Cereal Chemistry 71: 469–471

Kuipers, A. G. J., Jacobsen, E., and Visser, R. G. F. 1994. Formation and deposition of amylose in the potato tuber starch granule are affected by the reduction of granule-bound starch synthase gene expression. The Plant Cell 6:43–52.

Kumar, I., and Khush, G. S. 1988. Inheritance of amylose content in rice (*Oryza sativa* L.). Euphytica 38:261–269.

Laemmli, U. K. 1970. Cleavage of structural proteins during the assembly of the head of bacteriophage T4. Nature 227:680–685.

Lai, V. M.-F., Lu, S., and Lii, C.-y. 2000. Molecular characteristics influencing retrogradation kinetics of rice amylopectins. Food Chemistry 77:272–278.

Li, J. H., Vasanthan, T., Rossnagel, B., and Hoover, R. 2001. Starch from hull-less barley: I. Granule morphology, composition and amylopectin structure. Food Chemistry 74:395–405.

Li, J. H., Vasanthan, T., Rossnagel, B., and Hoover, R. 2001. Starch from hull-less barley: II. Thermal, rheological, and acid hydrolysis characteristics. Food Chemistry 74:407–415.

Li, Z., Rahman, S., Kosar-Haskemi, B., Mouille, G., Appels, R. and Morell, M. K. 1999. Cloning and characterization of a gene encoding wheat starch synthase I. Theoretical and Applied Genetics 98:1208–1216.

van der Leij, F. R., Visser, R. G. F., Oosterhaven, K., van der Kop, D. A. M., Jacobsen, E., and Feenstra, W. J. 1991. Complementation of the amylose-free starch mutant of potato (*Solanum tuberosum*) by the gene encoding granule-bound starch synthase. Theoretical and Applied Genetics 82:289–295.

Lloyd, J. R., Landschütze, V, and Kossmann, J. 1999. Simultaneous antisense inhibition of two starch-synthase isoforms in potato tubers to accumulation of grossly modified amylopectin. Biochemical Journal 338:515–521

Lu, T. J., Jane, J. L., Keeling, P. L., and Singletary, G. W. 1996. Maize starch fine structures affected by ear developmental temperature. Carbohydrate Research 282:157–170.

Macdonald, F. D. and Preiss, J. 1983. Solubilization of the starch-granule-bound starch synthase of normal maize kernels [*Zea mays*]. Plant Physiology 73:175–178.

Macdonald, F. D. and Preiss, J. 1985. Partial purification and characterization of granule-bound starch synthases from normal and waxy maize. Plant Physiology 78:849–852.

Maddelein, M. L., Libessart, N., Bellanger, F., Delrue, B., D'Hulst C. 1994. Towards an understanding of the biogenesis of the starch granule: determination of granule bound and soluble starch synthase functions in amylopectin synthesis. Journal of Biological Chemistry 269:25150–25157

Marshall, J., Sidebottom, C., Debet, M., Martin, C., Smith, A. M. and Edwards, A. 1996. Identification of the major starch synthase in the soluble fraction of potato tubers. The Plant Cell 8:1121–1135

Matsumoto, A., Nakajima, T. and Matsuda, K. 1990. A kinetic study between the interaction of glycogen and *Neurospora crassa* branching enzyme. Journal of Biochemistry 107(1):123–126.

Miura, H. and Sugawara, A. 1996. Dosage effects of three Wx genes on amylose synthesis in wheat endosperm. Theoretical and Applied Genetics 93:1066–1070.

Miura, H., Araki, E., and Tarui, S. 1999. Amylose synthesis capacity of the three Wx genes of wheat cv. Chinese Spring. Euphytica 108:91–95.

Morrison, W. R. 1988. Lipids in cereal starches: a review. Journal of Cereal Science 8:1–15.

Morrison, W. R. and Laignelet, B. 1983. An improved colorimetric procedrue for determining apparent and total amylose in cereal and other starches. J. Cereal Sci. 1:9–20.

Mu, C., Harn, C., Ko, Y. T., Singletary, G. W., Keeling, P. L. and Wasserman, B. P. 1994. Association of a 76 kDa polypeptide with soluble starch synthase I activity in maize (cvB73) endosperm. The Plant Journal 6:151–159

Mu-Forster, C., Huang, R., Powers, J. R., Harriman, R. W., Knight, M., Singletary, G. W., Keeling, P. L. and Wasserman, B. P. 1996. Physical association of starch biosythetic enzymes with starch granules of maize endosperm: Granule-associated forms of starch synthase I and starch branching enzyme II. Plant Physiology 111:821–829.

Myers, A. M., Morell, M. K., James, M. G. and Ball, S. G. 2000. Recent progress toward understanding biosynthesis of the amylopectin crystal. Plant Physiology 122:989–997.

Nakajima, R., Imanaka, T. and Aiba, S. 1986. Comparison of amino acid sequences of eleven different a-amyloses. Applied Microbiology and Biotechnology 23:355–360

Nanmori, T., Nagai, M., Shimizu, Y., Shinke, R. and Mikami, B. 1993. Cloning of the -amylose gene from *Bacillus cereus* and characteristics of the primary structure of the enzyme. Applied & Environmental Microbiology 59(2):623–627

Neuffler, M. G., Coe, E. H., and Wessler, S. R. 1997. Mutants of Maize. Cold Spring Harbor Laboratory Press, Plainview.

Neuffer, M. G. 1971. Chemical mutagens and in vitro germination of pollen. Maize Genetics Cooperation Newsletter 45:146–149.

Nichols, D. J., Keeling, P. L., Spalding, M., and Guan, H. 2000. Involvement of conserved aspartate and glutamate residues in the catalysis and substrate binding of maize starch synthase. Biochemistry 39:7820–7825.

Oda, S., Kiribuchi, C., and Seko, H. 1992. A bread wheat mutant with low amylose content induced by ethyl methanesulphonate. Japanese Journal of Breeding 42:151–154.

Okagaki, R. J., Neuffer, M. G., and Wessler, S. R. 1991. A deletion common to two independently derived waxy mutations in maize. Genetics 128:425–431.

Pollock, C. and Preiss, J. 1980. The citrate-stimulated starch synthase of starchy maize kernels: purification and properties. Archives of Biochemistry and Biophysics 204:578–588.

Reddy, K. R., Ali, S. Z. and Bhattacharya, K. R. 1993. The fine structure of rice starch amylopectin and its relation to the texture of cooked rice. Carbohydrate Polymers 22:267–275

Reddy, I. and Seib, P. A. 2000. Modified waxy wheat starch compared to modified waxy corn starch. Journal of Cereal Science 31:25–39.

Reyes, A. C., Albano, E. L., Briones, V. P., and Juliano, B. O. 1965. Varietal differences in physicochemical properties of rice starch and its fractions. Journal of Agricultural and Food Chemistry 13:438–442.

Ring, S. G. 1985. Some studies on starch gelation. Starch/Stärke 37:80–83.

Salehuzzaman, S. N. I. M., Vincken, J.-P., van der Wal, M., Straatman-Engelen, I., Jacobsen, E., and Visser, R. G. F. 1999. Expression of a cassava granule-bound starch synthase gene in the amylose-free potato only partially restores amylose content. Plant, Cell and Environment 22:1311–1318.

Sanchez, P. C., Juliano, B. O., Laude, V. T., and Perez, C. M. 1988. Nonwaxy rice for tapuy (rice wine) production. Cereal Chemistry 65:240–243.

Sano, Y. 1984. Differential regulation of waxy gene expression in rice endosperm. Theoretical and Applied Genetics 68:467–473.

Sano, Y., Katsumata, M., and Okuno, K. 1986. Genetic studies of speciation in cultivated rice. 5. Inter- and intraspecific differentiation in the waxy gene expression of rice. Euphytica 35:1–9.

Sasaki, T., Yasui, T., and Matsuki, J. 2000. Effect of amylose content on gelatinization, retrogradation, and pasting properties of starches from waxy and nonwaxy wheat and their F1 seeds. Cereal Chemistry 77:58–63

Shannon, J. C. and Garwood D. L. 1984. Ch. 3, Genetics and Physiology of starch development, in Starch: Chemistry and Technology; R. L. Whistler, J. N. BeMiller, and E. F. Paschall, eds. Academic Press, Orlando.

Shimada, H., Tada, Y., Kawasaki, T., and Fujimura, T. 1993. Antisense regulation of the rice waxy gene expression using a PCR-amplified fragement of the rice genome reduces the amylose content in grain starch. Theoretical and Applied Genetics 86:665–672.

Shure, M., Wessler, S. and Fedoroff, N. 1983. Molecular identification and isolation of the waxy locus in maize. Cell 35:225–233.

Siggens, K. 1987. Molecular cloning and characterization of the B-amylose gene from *Bacillus circulans*. Molecular Microbiology 1:86–91.

Singh, S. K., Johnson, L. A., Pollak, L. M., Fox, S. R., and Bailey, T. B. 1997. Comparison of laboratory and pilot-plant corn wet-milling procedures. Cereal Chem. 74:40–48.

Smith, A. M., Denyer, K. and Martin, C. 1997. The synthesis of the starch granule. Annual Review of Plant Physiology and Plant Molecular Biology 48:67–87.

Sprague, G. F. and Jenkins, M. T. 1948. The development of waxy corn for industrial use. Iowa State College Journal of Science 22:205–213.

Sprague, G. F., Brimhall, B., and Hixon, R. M. 1943. Some effects of the waxy gene in corn on the properties of the endosperm starch. Journal of the American Society of Agronomy 35:817–822.

Takahashi, S. and Seib, P. A. 1988. Paste and gel properties of prime corn and wheat starches with and without native lipids. Cereal Chemistry 65:474–483.

Takeda, Y., Guan, H. and Preiss, J. 1993. Branching of amylose by the branching isoenzymes of maize endosperm. Carbohydrate Research 240:253–263.

Takeda, Y., Hizukuri, S., and Juliano, B. O. 1986. Purification and structure of amylose from rice starch. Carbohydrate Research 148:299–308.

Takeda, Y., Hizukuri, S., Takeda, C., and Suzuki, A. 1987. Structures of branched molecules of amyloses of various origins, and molar fractions of branched and unbranched molecules. Carbohydate Research 165:139–145.

Takeda, Y. and Preiss, J. 1993. Structures of B90 (sugary) and W64A (normal) maize starches. Carbohydrate Research 240:265–275.

Takeda, Y., Shirasaka, K., and Hizukuri, S. 1984. Examination of the purity and structure of amylose by gel-permeation chromatography. Carbohydrate Research 132:83–92.

Takeda, C., Takeda, Y., and Hizukuri, S. 1989. Structure of amylomaize amylose. Cereal Chemistry 66:22–25

Takeo, K. and Nakamura, S. 1972. Dissociation constants of glucan phosphorylases of rabbit tissues studied by polyacrylamide gel disc electrophoresis. Archives of Biochemistry and Biophysics 153:1–7.

Tester, R. F. and Morrison, W. R. 1990. Swelling and gelatinization of cereal starches. I. Effects of amylopectin, amylose, and lipids. Cereal Chemistry 67:551–557

Tester, R. F. and Morrison, W. R. 1992. Swelling and gelatinization of cereal starches. III. Some properties of waxy and normal nonwaxy barley starches. Cereal Chemistry 69:654–658.

Tsai, C. Y. 1974. The function of the waxy locus in starch synthesis in maize endosperm. Biochemical Genetics 11:83–96.

Tyynela, J. and Schulman, A. H. 1994. An analysis of soluble starch synthase isozymes from the developing grains of normal and shx cv Bomi barley (*Hordeum vulgare*). Physiologica Plantarum 89:835–841.

Villareal, C. P., and Juliano, B. O. 1989. Comparative levels of waxy gene product of endosperm starch granules of different rice ecotypes. Starch 41:369–371.

Van der Leij, F. R., Visser, R. G. F., Oosterhaven, K., van der Kop, D. A. M., Jacobsen, E., and Feenstra, W. J. 1991. Complementation of the amylose-free starch mutant of potato (*Solanum tuberosum*) by the gene encoding granule-bound starch synthase.

Visser, R. G. F., Hergersberg, M., van der Leij, F. R., Jacobsen, E., Witholt, B., and Feenstra, W. J. 1989. Molecular cloning and partial characterization of the gene for granule-bound starch synthase from a wildtype and an amylose-free potato (*Solanum tuberosum* L.). Plant Science 64(2):185–192.

Visser, R. G. F., Somhorst, I., Kuipers, G. J., Ruys, N. J., Feenstra, W. J., and Jacobsen, E. 1991. Inhibition of the expression of the gene for granule-bound starch synthase in potato by antisense constructs. Molecular and General Genetics 225(2):289–296.

Wang, Y.-J., and Wang, L. 2002. Structures of four waxy rice starches in relation to thermal, pasting, and textural properties. Cereal Chemistry 79:252–256.

Wang, Y. J., White, P., Pollak, L. and Jane, J. 1993. Characterization of starch structures of 17 maize endosperm mutant genotypes with oh43 inbred line background. Cereal Chemistry 70:171–179.

Wang, Z.-Y., Zheng, F.-Q., Shen, G.-Z., Gao, J.-P., Snustad, D. P., Li, M.-G., Zhang, J.-L., and Hong, M.-M. 1995. The amylose content in rice endosperm is related to the post-transcriptional regulation of the waxy gene. The Plant Journal 7:613–622

Whistler, R. L. and BeMiller, J. N. 1997. Carbohydrate chemistry for Food Scientists, Eagan Press, St. Paul.

Whistler, R. L. and Daniel, J. R. 1985. Ch. 3, Carbohydrates, in Food Chemistry, O. R. Fennema, ed., Marcel Dekker, Inc., New York.

Yamin, F. F., Lee, M., Pollak, L. M., and White, P. J. 1999. Thermal properties of starch in corn variants isolated after chemical mutableness of inbred line B73. Cereal Chemistry 76:175–181.

Yanagisawa, T., Kiribuchi-Otobe, C., and Yoshida, H. 2001. An alanine to threonine change in the Wx-D1 protein reduces GBSS I activity in waxy mutant wheat. Euphytica 121:209–214.

Yeh, J. Y., Garwood, D. L., Shannon, J. C. 1981. Characterization of starch from maize endosperm mutants. Starch/Stärke 33(7):222–230

Yuan, R. C. and Thompson, D. B. 1998. Rheological and thermal properties of aged starch pastes from three waxy maize genotypes. Cereal Chemistry 75:117–123.

Zheng, G. H., Han, H. L., and Bhatty, R. S. 1999. Functional properties of cross-linked and hydroxypropylated waxy hull-less barley starches. Cereal Chemistry 76:182–188.

All references cited herein are incorporated in their enrirety by reference.

We claim:

1. A genetically altered maize plant which produces a waxy E starch having a reduced amylose content, wherein: (i) said starch has an EM greater than the EM of a waxy starch produced from a waxy maize plant and less than the EM of a starch from a wild type maize plant, (ii) said reduced amylose starch has an AP ratio within 0.5 of the AP ratio of starch of said wild type maize plant, and (iii) said reduced amylose starch is indistinguishable from starch from said wild type plant when stained with iodine.

2. The genetically altered maize plant of claim 1, having reduced GBSS activity; wherein the reduced GBSS activity is the result of at least one of a genetic mutation or a genetic transformation.

3. A method of producing a waxy E starch having a reduced amylose content from a mutant maize plant, wherein (i) said starch has an EM greater than the EM of a waxy starch produced from a waxy maize plant and less than the EM of a starch from a wild type maize plant, (ii) said reduced amylose starch has an AP ratio within 0.5 of the AP ratio of starch of said wild type maize plant, and (iii) said reduced amylose starch is indistinguishable from starch from said wild type plant when stained with iodine; the method comprising the steps of; collecting pollen from a maize plant to be mutated, applying EMS to said pollen, thereby forming treated pollen, pollinating the maize plant to be mutated with said treated pollen; harvesting M1 propagative structures produced from the pollinated plant, planting said M1 propagative structures, harvesting M2 propagative structures from said planted M1 propagative structures, and selecting or screening for said starch from said M2 propagative structures.

4. A method of producing a waxy E starch having a reduced amylose content from a mutant maize plant, wherein: (i) said starch has an EM greater than the EM of a waxy starch produced from a waxy maize plant and less than the EM of a starch from a wild type maize plant, (ii) said reduced amylose starch has an AP ratio within 0.5 of the AP ratio of starch of said wild type maize plant, and (iii) said reduced amylose starch is indistinguishable from starch from wild type plant when stained with iodine; the method comprising the steps of inducing a mutation in a DNA locus affecting starch synthesis in a starch storage organ of the plant to be mutated, selecting propagative structures from said mutant, growing plants from said propagative structures, and selecting or screening starch storing organs for said starch.

5. A method of producing a plant waxy-E starch having a reduced amylose content from a genetically altered hybrid maize plant comprising a mutated GBSS, wherein:
 (i) said starch has an EM greater than the EM of a waxy starch produced from a hybrid waxy maize plant and less than the EM of a starch from a hybrid wild type maize plant,
 (ii) said reduced amylose starch has an AP ratio within 0.5 of the AP ratio of starch of said wild type maize plant, and
 (iii) said reduced amylose starch is indistinguishable from starch from said hybrid wild type plant when stained with iodine;
 the said method comprising the step of incorporating said mutated GBSS into at least one parent of said genetically altered hybrid plant, and the step of selecting or screening starch organs of said hybrid and of said at least one parent for said reduced amylose starch; wherein said hybrid maize plant comprises said mutated GBSS and produces said reduced amylose starch.

6. An isolated nucleic acid molecule encoding a polypeptide having the granule bound starch synthase activity of a polypeptide having the amino acid sequence set forth in SEQ ID NO:4.

7. An isolated nucleic acid molecule encoding a polypeptide comprising the amino acid sequence as set forth in SEQ ID NO:4.

8. An isolated nucleic acid molecule comprising the sequence as set forth in SEQ ID NO:2.

9. The genetically altered maize plant of claim 1, wherein the starch of said plant has an EM at least twice the EM of waxy starch produced from a waxy maize plant.

10. The genetically altered maize plant of claim 1, wherein the starch of said plant has an EM of at least 10 Pascals.

* * * * *